United States Patent
Takemura et al.

[11] Patent Number: 6,121,285
[45] Date of Patent: Sep. 19, 2000

[54] SUBSTITUTED AMINOCYCLOALKYLPYRROLIDINE DERIVATIVES AND CIS-SUBSTITUTED AMINOCYCLOALKYLPYRROLIDINE DERIVATIVES

[75] Inventors: Makoto Takemura; Youichi Kimura; Hisashi Takahashi; Kenichi Kimura; Satoru Miyauchi; Hitoshi Ohki; Kazuyuki Sugita; Rie Miyauchi, all of Tokyo, Japan

[73] Assignee: Daiichi Pharmaceutical Co., Ltd., Tokyo, Japan

[21] Appl. No.: 09/082,155

[22] Filed: May 21, 1998

Related U.S. Application Data

[63] Continuation-in-part of application No. PCT/JP96/03440, Nov. 22, 1996.

[30] Foreign Application Priority Data

| Nov. 22, 1995 | [JP] | Japan | 7-304129 |
| Jul. 23, 1996 | [JP] | Japan | 8-192637 |
| May 21, 1997 | [JP] | Japan | 9-131413 |
| May 29, 1997 | [JP] | Japan | 9-140643 |

[51] Int. Cl.[7] .................. C07D 471/02; C07D 215/16
[52] U.S. Cl. .................. 514/312; 514/303; 514/305; 514/299; 546/119; 546/121; 546/123; 546/153; 546/156
[58] Field of Search .................. 546/119, 121, 546/123, 153, 156; 514/303, 305, 312, 299

[56] References Cited

U.S. PATENT DOCUMENTS

| 5,098,912 | 3/1992 | Hayakawa | 514/312 |
| 5,416,222 | 5/1995 | Hayakawa | 548/560 |
| 5,547,962 | 8/1996 | Ito et al. | 514/312 |
| 5,587,386 | 12/1996 | Hayakawa | 514/312 |
| 5,696,132 | 12/1997 | Hayakawa | 514/300 |

FOREIGN PATENT DOCUMENTS

| 62-234082 | 10/1987 | Japan . |
| 5-163244 | 6/1993 | Japan . |
| 7-23369 | 3/1995 | Japan . |
| 7-300416 | 11/1995 | Japan . |
| 96/23782 | 8/1996 | WIPO . |

OTHER PUBLICATIONS chemical Abstracts 125:247632, abstract of WO 9623782, 1996.
chemical abstracts 126:117990, abstract of WO 9639407, 1996.
Chemical Abstracts 123:313930, abstract of WO 9510519, 1995.

(List continued on next page.)

*Primary Examiner*—D Margaret Mach
*Attorney, Agent, or Firm*—Sughrue, Mion, Zinn, Macpeak & Seas, PLLC

[57] ABSTRACT

An antimicrobial drug having excellent antimicrobial activity and high safety is disclosed, which comprises as an active ingredient, a quinolone-derivative having a substituted aminocycloalkylpyrrolidine as a substituent and which is further substituted with various substituents, represented by formula (I), its salts and hydrates thereof:

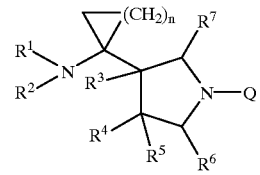

(I)

wherein Q is represented by formula (II) or (IV).

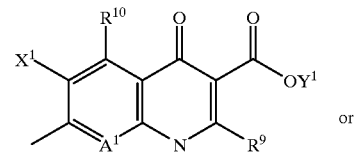

(II)

or

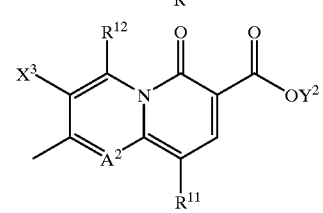

(IV)

Also disclosed is a quinolone derivative where $R^4$ and the substituent on the pyrrolidine ring of the following formula:

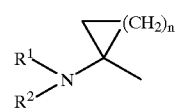

are located at the cis-configuration; and Q is represented by the formula:

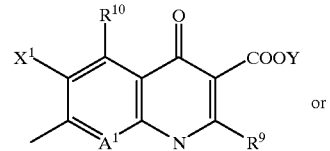

or

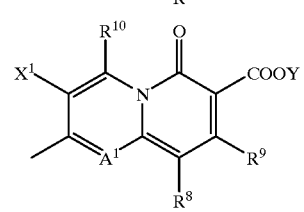

47 Claims, No Drawings

OTHER PUBLICATIONS

Chemical Abstract 123:9413, 1994.
chemical Abstract 106:138267, 1987.
Chemical Abstracts 110:8191, abstract of JP 63166876, 1988.
Chem. Pharm. Bull., 42(7), (1994), p. 1442–1454, Kimura, Youichi et al.

SUBSTITUTED AMINOCYCLOALKYLPYRROLIDINE DERIVATIVES AND CIS-SUBSTITUTED AMINOCYCLOALKYLPYRROLIDINE DERIVATIVES

CROSS REFERENCE TO RELATED APPLICATIONS

This is a continuation-in-part of PCT/JP96/03440 filed Nov. 22, 1996.

FIELD OF THE INVENTION

This invention relates to antibacterial and antimicrobial compounds useful for pharmaceutical preparations, veterinary drugs, drugs for fisheries use and antibacterial and antimicrobial preservatives. This invention also relates to antibacterial and antimicrobial drugs and antibacterial and antimicrobial preparations containing these compounds.

BACKGROUND OF THE INVENTION

Since the discovery of norfloxacin, attempts have been made to improve the antimicrobial activity and pharmacokinetics of synthetic quinolone antimicrobial agents. As a result, a number of compounds are clinically available today as chemotherapeutic drugs efficacious in treating systemic infectious diseases.

In recent years, however, bacteria hyposensitive to these drugs have been increasing in the field of clinical medicine. Moreover, some bacteria tolerant to drugs other than these synthetic quinolone antimicrobial agents have also become hyposensitive thereto. *Staphylococcus aureus* (MRSA) is an example of such bacteria having no sensitivity to β-lactam antibiotics. Therefore, there is an urgent need to develop highly efficacious drugs in the field of clinical medicine.

In addition, it is reported that these antimicrobial agents sometimes induce convulsions when administered together with nonsteroidal anti-inflammatory drugs and exhibit other side effects such as phototoxicity. Thus, there is also a need to develop safer quinolone drugs.

SUMMARY OF THE INVENTION

In view of the above, the present inventors have conducted extensive studies with the aim of providing compounds which satisfy the aforementioned requirements.

As a result, the present inventors have discovered that substituted aminomethylpyrrolidine derivatives represented by the following formulae (I) and (XI), their salts and hydrates thereof have a broad antibacterial spectrum, exhibit potent antibacterial activity against quinolone-resistant bacteria including Gram positive bacteria, particularly MRSA, and also have favorable pharmacokinetics and high safety. The present invention has been accomplished on the basis of these findings.

Accordingly, a first aspect of the present invention relates to a compound represented by the following formula (I), its salts and hydrates thereof:

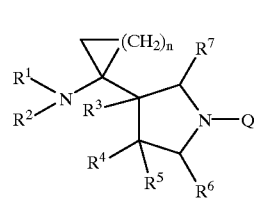

{wherein $R^1$ represents a hydrogen atom or an alkyl group having 1 to 6 carbon atoms;
$R^2$ represents a hydrogen atom or an alkyl group having 1 to 6 carbon atoms,
wherein the alkyl group represented by $R^2$ may have at least one substituent selected from the group consisting of a hydroxyl group, a halogen atom, an alkylthio group having 1 to 6 carbon atoms and an alkoxyl group having 1 to 6 carbon atoms;
$R^3$ represents a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms,
wherein the alkyl group represented by $R^3$ may have at least one substituent selected from the group consisting of a hydroxyl group, a halogen atom and an alkoxyl group having 1 to 6 carbon atoms;
$R^4$ and $R^5$ each independently represents a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms,
wherein the alkyl group represented by $R^4$ and $R^5$ may have at least one substituent selected from the group consisting of a hydroxyl group, a halogen atom and an alkoxyl group having 1 to 6 carbon atoms, and
$R^4$ and $R^5$ may be combined to form a hydroxyimino group, a poly-methylene chain having 3 to 6 carbon atoms (so as to form a spiro cyclic structure together with the pyrrolidine ring) or an alkyloxyimino group having 1 to 6 carbon atoms;
$R^6$ and $R^7$ each independently represents a hydrogen atom or an alkyl group having 1 to 6 carbon atoms;
n is an integer of 1 to 3; and
Q is a partial structure represented by the following formula (II):

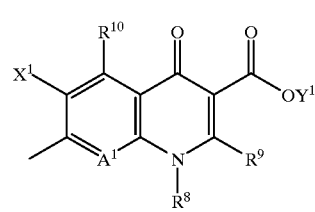

[wherein $R^8$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have one or more substituents, an aryl group which may have one or more substituents, a heteroaryl group which may have one or more substituents, an alkoxyl group having 1 to 6 carbon atoms or an alkylamino group having 1 to 6 carbon atoms;

$R^9$ represents a hydrogen atom or an alkylthio group having 1 to 6 carbon atoms, wherein $R^8$ and $R^9$ may be combined to form a cyclic structure including a part of the mother nucleus, and the ring may contain a sulfur atom as a ring constituting atom and may further have an alkyl group having 1 to 6 carbon atoms as a substituent;

$X^1$ represents a halogen atom or a hydrogen atom;

$R^{10}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group represented by $R^{10}$ may have at least one substituent selected from the group consisting of a formyl group, an alkyl group having 1 to 6 carbon atoms and an acyl group having 2 to 5 carbon atoms;

$A^1$ represents a nitrogen atom, or a partial structure represented by the following formula (III):

(III)

(wherein $X^2$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group represented by $X^2$ may have at least one substituent selected from the group consisting of a formyl group, an alkyl group having 1 to 6 carbon atoms and an acyl group having 2 to 5 carbon atoms, and $X^2$ and $R^8$ may be combined to form a cyclic structure including a part of the mother nucleus, and the ring may contain an oxygen atom, a nitrogen atom or a sulfur atom as a ring constituting atom and may further have an alkyl group having 1 to 6 carbon atoms as a substituent); and $Y^1$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group] or Q is a partial structure represented by the following formula (IV):

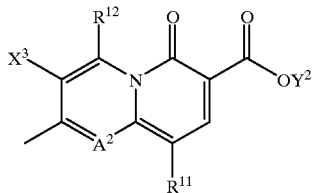

(IV)

[wherein $R^{11}$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have one or more substituents, an aryl group which may have one or more substituents, a heteroaryl group which may have one or more substituents, an alkoxyl group having 1 to 6 carbon atoms or an alkylamino group having 1 to 6 carbon atoms;

$R^{12}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group represented by $R^{12}$ may have at least one substituent selected from the group consisting of a formyl group, an alkyl group having 1 to 6 carbon atoms and an acyl group having 2 to 5 carbon atoms;

$X^3$ represents a halogen atom or a hydrogen atom;

$A^2$ represents a nitrogen atom or a partial structure represented by the following formula (V):

(V)

(wherein $X^4$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group-represented by $X^4$ may have at least one substituent selected from the group consisting of a formyl group, an alkyl group having 1 to 6 carbon atoms and an acyl group having 2 to 5 carbon atoms, and $X^4$ and $R^{11}$ may be combined to form a cyclic structure including a part of the mother nucleus, and the ring may contain an oxygen atom, a nitrogen atom or a sulfur atom as a ring constituting atom and may further have an alkyl group having 1 to 6 carbon atoms as a substituent); and $Y^2$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group]}.

The above first aspect of the present invention also relates to:

the aforementioned compound, its salts and hydrates thereof, wherein Q in formula (I) has a structure represented by formula (II);

the aforementioned compound, its salts and hydrates thereof, wherein $R^8$ is a halogenocyclopropyl group;

the aforementioned compound, its salts and hydrates thereof, wherein the halogenocyclopropyl group in formula (I) is a 1,2-cis-2-halogenocyclopropyl group;

the aforementioned compound, its salts and hydrates thereof, wherein the halogenocyclopropyl group in formula (I) is a stereochemically pure substituent;

the aforementioned compound, its salts and hydrates thereof, wherein the halogenocyclopropyl group in formula (I) is a (1R,2S)-2-halogenocyclopropyl group;

the aforementioned compound, its salts and hydrates thereof, wherein the halogen atom of the halogenocyclopropyl group in formula (I) is a fluorine atom;

the aforementioned compound, its salts and hydrates thereof, wherein the compound of formula (I) is a stereochemically pure compound;

a pharmaceutical preparation which comprises the compound of formula (I) or its salt or a hydrate thereof as an active ingredient; and an antibacterial drug or antibacterial preparation which comprises the compound of formula (I) or its salt or a hydrate thereof as an active ingredient.

A second aspect of the present invention relates to a compound represented by the following formula (XI), its salts and hydrates thereof:

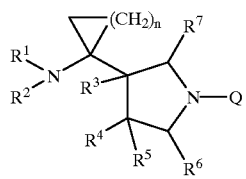

(XI)

wherein $R^1$ represents a hydrogen atom or an alkyl group having 1 to 6 carbon atoms;

$R^2$ represents a hydrogen atom or an alkyl group having 1 to 6 carbon atoms, provided that the alkyl group may have one or more substituents selected from the group consisting of a hydroxyl group, a halogen atoms and an alkoxyl group having 1 to 6 carbon atoms;

$R^3$ and $R^5$ each represents a hydrogen atom;

$R^4$ represents a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, provided that the alkyl group may have one or more substituents selected from the group consisting of a hydroxyl group, a halogen atom and an alkoxyl group having 1 to 6 carbon atoms; and $R^4$ and the substituent on the pyrrolidine ring of the following formula:

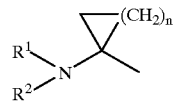

are located in the cis-configuration;

$R^6$ and $R^7$ each independently represents a hydrogen atom or an alkyl group having 1 to 6 carbon atoms;

n is an integer of from 1 to 3; and

Q represents a partial structure represented by the following formula:

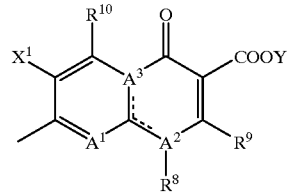

wherein $R^8$ represents an alkyl group having 1 to 6 carbon atoms, an alkenyl group having 2 to 6 carbon atoms, a halogenoalkyl group having 1 to 6 carbon atoms, a substituted or unsubstituted cyclic alkyl group having 3 to 6 carbon atoms; a substituted or unsubstituted aryl group, a substituted or unsubstituted heteroaryl group, an alkoxyl group having 1 to 6 carbon atoms or an alkylamino group having 1 to 6 carbon atoms;

$R^9$ represents a hydrogen atom or an alkylthio group having 1 to 6 carbon atoms;

$R^9$ and $R^8$ may form together with a part of the mother nucleus a cyclic structure optionally containing a sulfur atom as a constituent atom thereof and optionally having an alkyl group having 1 to 6 carbon atoms as a substituent;

$R^{10}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, provided that the amino-group may have one or more substituents selected from the group consisting of a formyl group, an alkyl group having 1 to 6 carbon atoms and an acyl group having 2 to 5 carbon atoms;

$X^1$ represents a halogen atom or a hydrogen be atom;

$A^1$ represents a nitrogen atom or a partial structure represented by the following formula (XII):

(XII)

wherein $X^2$ represents a hydrogen atom, an amino group, a halogen atom, a cyano group, a halogenomethyl group, a halogenomethoxy group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, provided that the amino group may have one or more substituents selected from the group consisting of a formyl group, an alkyl group having 1 to 6 carbon atoms and an acyl group having 2 to 5 carbon atoms; and X² and R⁸ may form together with a part of the mother nucleus a cyclic structure optionally containing an oxygen atom, a nitrogen atom or a sulfur atom as a constituent atom thereof and optionally having an alkyl group having 1 to 6 carbon atoms as a substituent;

A² and A³ each represents a nitrogen atom or a carbon atom, provided that A², A³ and the carbon atom to which they are bonded may form together with the bonds among them, expressed in dotted lines, a partial structure represented by the following formula:

>C=C(A¹=)—N(R⁸)—

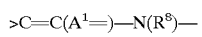

or

>N—C(A¹=)=C(R⁸)—;

and

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkyl group having 1 to 6 carbon atoms and a phenyl group.

The above second aspect of the present invention also relates to:

the compound of formula (XI), wherein Q has a structure represented by the following formula, its salts and hydrates thereof:

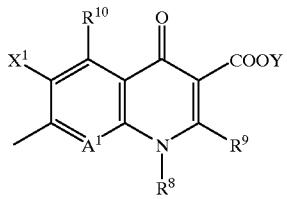

or the following formula:

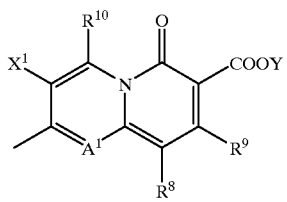

wherein R⁸, R⁹, R¹⁰, A¹, X¹ and Y are each as defined above;

the compound of formula (XI), wherein Q has a structure represented by the following formula, its salts and hydrates thereof:

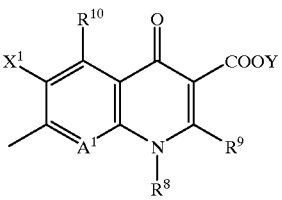

wherein R⁸, R⁹, R¹⁰, A¹, X¹ and Y are each as defined above;

the compound of formula (XI), wherein Q is a 6-carboxy-9-fluoro-2,3-dihydro-3-(S)-methyl-7-oxo-7H-pyrido[1,2,3-de][1,4]benzoxazin-10-yl group (following formula), its salts and hydrates thereof:

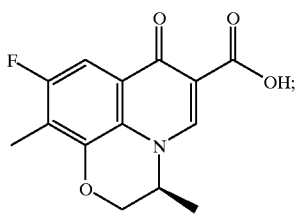

the compound of formula (XI), wherein Q is an 8-amino-6-carboxy-9-fluoro-2,3-dihydro-3-(S)-methyl-7-oxo-7H-pyrido[1,2,3-de][1,4]benzoxazin-10-yl group (following formula), its salts and hydrates thereof:

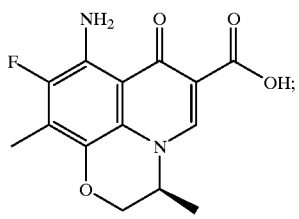

the compound of formula (XI), wherein Q is a 5-amino-3-carboxy-6-fluoro-1-[2-(S)-fluoro-1-(R)-cyclopropyl]-1,4-dihydro-8-methoxy-4-oxoquinolin-7-yl group (following formula), its salts and hydrates thereof:

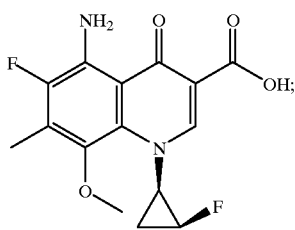

the compound of formula (XI), wherein Q is a 5-amino-3-carboxy-6-fluoro-1-[2-(S)-fluoro-1-(R)-cyclopropyl]-1,4-dihydro-8-methyl-4-oxoquinolin-7-yl group (following formula), its salts and hydrates thereof:

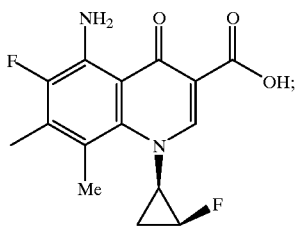

the compound of formula (XI), wherein Q is a 3-carboxy-6-fluoro-1-[2-(S)-fluoro-1-(R)-cyclopropyl]-1,4-dihydro-8-methoxy-4-oxoquinolin-7-yl group (following formula), its salts and hydrates thereof:

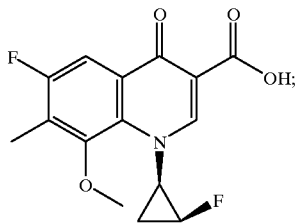

the compound of formula (XI), wherein the substituent $R^4$ is a halogen atom, its salts and hydrates thereof;

the compound of formula (XI), wherein the substituent $R^4$ is a fluorine atom, its salts and hydrates thereof;

the compound of formula (XI), wherein n is 1 or 2, its salts and hydrates thereof;

the compound of formula (XI), wherein n is 1, its salts and hydrates thereof;

the compound of formula (XI), wherein the substituent $R^4$ is a fluorine atom and n is 1 or 2, its salts and hydrates thereof;

the compound of formula (XI), wherein the substituent $R^4$ is a fluorine atom and n is 1, its salts and hydrates thereof;

the compound of formula (XI), wherein the substituent $R^8$ is a halogenocyclopropyl group, its salts and hydrates thereof;

the compound of formula (XI), wherein the substituent $R^8$ is a 1,2-cis-2-halogenocyclopropyl group, its salts and hydrates thereof;

the compound of formula (XI), wherein the substituent $R^8$ is stereochemically pure, its salts and hydrates thereof;

the compound of formula (XI), wherein the substituent $R^8$ is a (1R,2S)-2-halogenocyclopropyl group, its salts and hydrates thereof;

the compound of formula (XI), wherein the substituent $R^8$ is a (1R,2S)-2-fluorocyclopropyl group, its salts and hydrates thereof;

a stereochemically pure compound represented by formula (XI), its salts and hydrates thereof;

the compound of formula (XI), wherein the substituent $X^1$ is a halogen atom, its salts and hydrates thereof;

the compound of formula (XI), wherein $X^1$ is a fluorine atom, its salts and hydrates thereof;

10-[4-(R)-(1-aminocyclopropyl)-3-(S)-fluoro-1-pyrrolidinyl]-9-fluoro-2,3-dihydro-3-(S)-methyl-7-oxo-7H-pyrido[1,2,3-de][1,4]benzoxazine-6-carboxylic acid, its salts and hydrates thereof;

8-amino-10-[4-(R)-(1-aminocyclopropyl)-3-(S)-fluoro-1-pyrrolidinyl]-9-fluoro-2,3-dihydro-3-(S)-methyl-7-oxo-7H-pyrido[1,2,3-de][1,4]benzoxazine-6-carboxylic acid, its salts and hydrates thereof;

5-amino-7-[4-(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methyl-4-oxoquinoline-3-carboxylic acid, its salts and hydrates thereof;

5-amino-7-[4-(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methoxy-4-oxoquinoline-3-carboxylic acid, its salts and hydrates thereof;

7-[4-(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methoxy-4-oxoquinoline-3-carboxylic acid, its salts and hydrates thereof;

a drug containing as an active ingredient a compound represented by formula (XI), its salts and hydrates thereof, and hydrates of the salts of the compound of formula (XI);

an antimicrobial agent containing as an active ingredient a compound represented by formula (XI), its salts and hydrates thereof, and hydrates of the salts of the compound of formula (XI); etc.

The second aspect of the present invention further relates to a compound represented by the following formula (XVI), its salts and hydrates thereof:

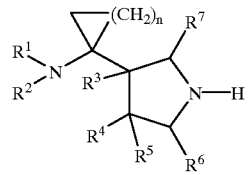

(XVI)

wherein $R^1$ represents a hydrogen atom or an alkyl group having 1 to 6 carbon atoms;

$R^2$ represents a hydrogen atom or an alkyl group having 1 to 6 carbon atoms, provided that the alkyl group may have one or more substituents selected from the group consisting of a hydroxyl group, a halogen atom and an alkoxyl group having 1 to 6 carbon atoms;

$R^3$ and $R^5$ each represents a hydrogen atom;

$R^4$ represents a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, provided that the alkyl group may have one or more substituents selected from the group consisting of a hydroxyl group, a halogen atom and an alkoxyl group having 1 to 6 carbon atoms; and $R^4$ and the substituent on the pyrrolidine ring of the following formula:

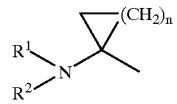

are located in the cis-configuration;

$R^6$ and $R^7$ each independently represents a hydrogen atom or an alkyl group having 1 to 6 carbon atoms; and n is an integer of from 1 to 3.

The second aspect of the present invention furthermore relates to the compound of formula (XVI), wherein the substituent $R^4$ is a halogen-atom, its salts and hydrates thereof;

the compound of formula (XVI), wherein the substituent $R^4$ is a fluorine atom, its salts and hydrates thereof;

the compound of formula (XVI), wherein n is 1 or 2, its salts and hydrates thereof;

the compound of formula (XVI), wherein n is 1, its salts and hydrates thereof;

the compound of formula (XVI), wherein the substituent $R^4$ is a fluorine atom and n is 1 or 2, its salts and hydrates thereof;

the compound of formula (XVI), wherein the substituent $R^4$ is a fluorine atom and n is 1, its salts and hydrates thereof;

4-(R)-(1-aminocyclopropyl)-3-(S)-fluoro-1-pyrrolidine, its salts and hydrates thereof; etc.

Other objects and advantages of the present invention will become apparent in view of the following detailed description and examples.

DETAILED DESCRIPTION OF THE INVENTION

The first aspect of the present invention is described in further detail below.

Substituents of the compound in accordance with the first aspect of the present invention represented by formula (I) are described as follows.

The substituent $R^1$ represents a hydrogen atom or an alkyl group having 1 to 6 carbon atoms, and the alkyl group may be either a straight- or branched-chain having 1 to 6 carbon atoms. Preferably, the alkyl group is a methyl, ethyl, n-propyl or isopropyl group.

The substituent $R^2$ represents a hydrogen atom or an alkyl group having 1 to 6 carbon atoms, and the alkyl group may have at least one substituent selected from the group consisting of a hydroxyl group, a halogen atom, an alkylthio group having 1 to 6 carbon atoms and an alkoxyl group having 1 to 6 carbon atoms.

The alkyl group may be either a straight- or branched-chain having 1 to 6 carbon atoms and is preferably a methyl, ethyl, n-propyl or isopropyl group.

When the alkyl group has a hydroxyl group as a substituent, the alkyl group may be either a straight- or branched-chain having 1 to 6 carbon atoms, and the hydroxyl group may most preferably be substituted on the terminal carbon atom of the alkyl group. Preferred examples of the alkyl group having a hydroxyl group are those which have up to 3 carbon atoms, such as hydroxymethyl, 2-hydroxyethyl, 2-hydroxypropyl, 3-hydroxypropyl and the like.

When the alkyl group has one or more halogen atoms as substituents, the alkyl group may be either a straight- or branched-chain having 1 to 6 carbon atoms, and a fluorine atom is desirable as the halogen atom.

When the alkyl group has an alkylthio group as a substituent, the alkyl group may be either a straight- or branched-chain having 1 to 6 carbon atoms, and the alkylthio group may also be either a straight- or branched chain having 1 to 6 carbon atoms. Preferred examples of the alkyl group having an alkylthio group include an alkylthiomethyl group, an alkylthioethyl group and an alkylthiopropyl group, and the alkylthio group may preferably have up to 3 carbon atoms. Most preferred examples include methylthiomethyl, ethylthiomethyl and methylthioethyl groups.

When the alkyl group has an alkoxyl group as a substituent, the alkyl group may be either a straight- or branched-chain having 1 to 6 carbon atoms, and the alkoxyl group may also be either a straight- or branched chain having 1 to 6 carbon atoms. Preferred examples of the alkyl group having an alkoxyl group include an alkoxymethyl group, an alkoxyethyl group and an alkoxypropyl group, and the alkoxyl group may preferably have up to 3 carbon atoms. Most preferred examples include methoxymethyl, ethoxymethyl and methoxyethyl groups.

The substituent $R^3$ represents a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, and the alkyl group may have at least one substituent selected from the group consisting of a hydroxyl group, a halogen atom and an alkoxyl group having 1 to 6 carbon atoms.

As the halogen atom, a fluorine or chlorine atom is preferable.

The alkyl group may be either a straight- or branched-chain having 1 to 6 carbon atoms, and a methyl, ethyl, n-propyl or isopropyl group is preferred.

The alkoxyl group may be either a straight- or branched-chain having 1 to 6 carbon atoms, and a methoxyl or ethoxyl group is preferred.

The alkylthio group may be either a straight- or branched-chain having 1 to 6 carbon atoms, and a methylthio or ethylthio group is preferred.

The alkyl group of 1 to 6 carbon atoms having a hydroxyl group may be either a straight- or branched-chain, and the hydroxyl group may most preferably be substituted on the terminal carbon atom of the alkyl group. Preferred examples of the alkyl group of 1 to 6 carbon atoms substituted with a hydroxyl group include hydroxymethyl, 2-hydroxyethyl and 3-hydroxypropyl groups.

As the halogen atom of the alkyl group having a halogen atom, a fluorine or chlorine atom is preferred, and a fluorine atom is particularly preferred. The alkyl group may be either a straight- or branched-chain.

In the alkyl group of 1 to 6 carbon atoms having an alkoxyl group, each alkyl moiety may be either a straight- or branched-chain, and an alkoxymethyl group or an alkoxyethyl group is preferred. The most preferred examples thereof include methoxymethyl, ethoxymethyl and 2-methoxyethyl groups.

The substituents $R^4$ and $R^5$ each independently represents a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, and the alkyl moiety of these groups may have at least one substituent selected from the group consisting of a hydroxyl group, a halogen atom and an alkoxyl group having 1 to 6 carbon atoms.

In addition, $R^4$ and $R^5$ may be combined together to form a hydroxyimino group, a methylene chain having 3 to 6 carbon atoms (so as to form a spiro cyclic structure together with the pyrrolidine ring) or an alkyloxyimino group having 1 to 6 carbon atoms.

As the halogen atom, a fluorine or chlorine atom is desirable.

The alkyl group may be either a straight- or branched-chain having 1 to 6 carbon atoms, and a methyl, ethyl, n-propyl or isopropyl group is preferred.

The alkoxyl group may be either a straight- or branched-chain having 1 to 6 carbon atoms, and a methoxyl or ethoxyl group is preferred.

The alkylthio group may be either a straight- or branched-chain having 1 to 6 carbon atoms, and a methylthio or ethylthio group is preferred.

The alkyl group of 1 to 6 carbon atoms having a hydroxyl group may be either a straight- or branched-chain, and the hydroxyl group may most preferably be substituted on the terminal carbon atom of the alkyl group. Preferred examples of the alkyl group of 1 to 6 carbon atoms substituted with a hydroxyl group include hydroxymethyl, 2-hydroxyethyl and 3-hydroxypropyl groups.

As the halogen atom of the alkyl group having a halogen atom, a fluorine or chlorine atom is preferred, and a fluorine atom is particularly preferred. The alkyl group may be either a straight- or branched-chain.

In the alkyl group of 1 to 6 carbon atoms having an alkoxyl group, each alkyl moiety may be either a straight- or branched-chain, and an alkoxymethyl group or an alkoxyethyl group is preferred. The most preferred examples thereof include methoxymethyl, ethoxymethyl and 2-methoxyethyl groups.

When the substituents $R^4$ and $R^5$ are combined to form a methylene chain, a three- to six-membered ring is newly formed, thereby forming a spiro cyclic structure together with the pyrrolidine ring. As the newly formed ring, a cyclopropyl or cyclobutyl ring having a size of 2 or 3 carbon atoms as the methylene chain is desirable.

Also, when $R^4$ and $R^5$ are combined to form an alkyloxyimino group, =N—O—Alkyl, the alkyl group may be either a straight- or branched-chain. As the alkyloxyimino group, a methoxyimino or ethoxyimino group is preferred.

The substituents $R^6$ and $R^7$ each independently represents a hydrogen atom or an alkyl group having 1 to 6 carbon atoms, and the alkyl group may be either a straight- or branched-chain having 1 to 6 carbon atoms and is preferably a methyl, ethyl, n-propyl or isopropyl group.

The character n is an integer of 1 to 3, and the corresponding ring may be a cyclopropane to cyclobutane ring. The compound of the first aspect of the present invention is characterized in that this moiety is a cyclic structure. As n, 1 is particularly preferred.

Q is a partial structure of a fused heterocycle represented by the following formula (II) or (IV).

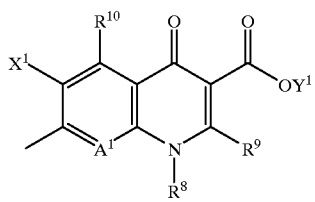

(II)

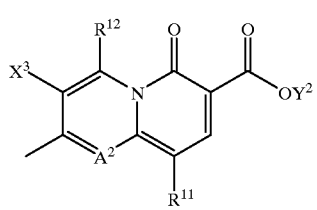

(IV)

The substituents $R^8$ and $R^{11}$ each independently represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have one or more substituents, an aryl group which may have one or more substituents, a heteroaryl group which may have one or more substituents, an alkoxyl group having 1 to 6 carbon atoms or an alkylamino group having 1 to 6 carbon atoms.

As the alkyl group having 1 to 6 carbon atoms, an ethyl group is particularly preferred. As the alkenyl group having 2 to 6 carbon atoms, a vinyl or 1-isopropenyl group is preferable. As the halogenoalkyl group having 1 to 6 carbon atoms, a 2-fluoroethyl group is preferable. As the cyclic alkyl group having 3 to 6 carbon atoms which may have one or more substituents, a cyclopropyl group and a 2-halogenocyclopropyl group are preferred, and a fluorine atom is particularly preferable as the halogen atom of the 2-halogenocyclopropyl group.

Examples of the aryl group which may have one or more substituents include phenyl and the like groups which may have 1 to 3 substituents selected from the group consisting, for example, of fluorine, chlorine, bromine and the like halogen atoms, a lower alkyl group having 1 to 6 carbon atoms, a hydroxyl group, an amino group, a nitro group and a lower alkoxyl group having 1 to 6 carbon atoms, and preferred examples thereof include phenyl, 2-fluorophenyl, 4-fluorophenyl, 2,4-difluorophenyl, 2-fluoro-4-hydroxyphenyl and the like groups.

The heteroaryl group is a substituent derived from an aromatic heterocyclic compound containing at least one hetero atom selected from nitrogen, oxygen and sulfur atoms. Examples thereof include pyridyl, pyrimidyl and the like. As the substituent on these rings, an alkyl group, a halogen atom and the like are preferable. As the alkoxyl group having 1 to 6 carbon atoms, a methoxyl group is preferable. As the alkylamino group having 1 to 6 carbon atoms, a methylamino group is preferable.

As the substituents $R^8$ and $R^{11}$, cyclic alkyl groups or halogenocycloalkyl groups are preferred. Of these groups, a cyclopropyl group or a 2-halogenocyclopropyl group is particularly preferred, and a fluorine atom is preferable as the halogen atom.

The substituent $R^9$ represents a hydrogen atom or an alkylthio group having 1 to 6 carbon atoms, or $R^8$ and $R^9$ may be combined to form a cyclic structure including a part of the mother nucleus (i.e., including the nitrogen atom to which $R^8$ is attached and the carbon atom to which $R^9$ is attached). The thus formed ring may contain a sulfur atom as a ring constituting atom and may further have an alkyl group having 1 to 6 carbon atoms as a substituent. The thus formed ring may have a ring size of from a four-membered to a six-membered ring which may be saturated, partially saturated or unsaturated.

The substituents $X^1$ and $X^3$ each independently represents a halogen atom or a hydrogen atom, and a fluorine atom is preferable in the case of a halogen atom. Of these, a fluorine or hydrogen atom is preferable as the substituent.

The substituents $R^{10}$ and $R^{12}$ each independently represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, wherein the amino group may have at least one substituent selected from the group consisting of a formyl group, an alkyl group having 1 to 6 carbon atoms and an acyl group having 2 to 5 carbon atoms.

The alkyl group may be either a straight- or branched-chain having 1 to 6 carbon atoms and is preferably a methyl, ethyl, n-propyl or isopropyl group. The alkenyl group may be either a straight- or branched-chain having 2 to 6 carbon atoms and is preferably a vinyl group. The alkynyl group may be either a straight- or branched-chain having 2 to 6 carbon atoms and is preferably an ethynyl group. As the halogen of the halogenomethyl group, fluorine is particularly preferred, and its number may be 1 to 3. The alkoxyl group may have 1 to 6 carbon atoms and is preferably methoxyl group.

As the substituents $R^{10}$ and $R^{12}$, an alkyl group or an amino group is preferred, and a methyl group or an unsubstituted amino group is particularly preferred.

When the substituent $R^{10}$ or $R^{12}$ is an amino group, a hydroxyl group or a thiol group, these groups may be protected by commonly used protective groups.

Illustrative examples of such protective groups include alkoxycarbonyl groups such as tert-butoxycarbonyl, 2,2,2-trichloroethoxycarbonyl and the like, aralkyloxycarbonyl groups such as benzyloxycarbonyl, p-methoxybenzyloxycarbonyl, p-nitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tert-butyl, benzyl, p-nitrobenzyl, p-methoxybenzyl, triphenylmethyl and the like, ethers such as methoxymethyl, tert-butoxymethyl, tetrahydropyranyl, 2,2,2-trichloroethoxymethyl and the like, and silyl groups such as trimethylsilyl, isopropyldimethylsilyl, tert-butyldimethylsilyl, tribenzylsilyl, tert-butyldiphenylsilyl and the like. Compounds having substituents which are protected by these protective groups are preferable particularly as production intermediates.

When $A^1$ is a partial structure represented by formula (III):

(III)

$X^2$ is a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms. The amino group may have at least one substituent selected from the group consisting of a formyl group, an alkyl group having 1 to 6 carbon atoms and an acyl group having 2 to 5 carbon atoms.

The alkyl group may be either a straight- or branched-chain having 1 to 6 carbon atoms and is preferably a methyl or ethyl group. The alkenyl group may be either a straight- or branched-chain having 2 to 6 carbon atoms and is preferably a vinyl group. The alkynyl group may be either a straight- or branched-chain having 2 to 6 carbon atoms and is preferably an ethynyl group. As the halogen of the halogenomethyl group, fluorine is particularly preferred, and the number of fluorine atoms may be 1 to 3. The alkoxyl group may have 1 to 6 carbon atoms and is preferably a methoxyl group. As the halogen of the halogenomethoxyl group, fluorine is particularly preferred, and the number of fluorine atoms may be 1 to 3.

Of these substituents, an alkyl group or an alkoxyl group is preferred. Most preferred is a methyl or methoxyl group.

In addition, $X^2$ and $R^8$ may be combined to form a cyclic structure (the ring may have a ring size of from a four-membered to a seven-membered ring which may be saturated, partially saturated or unsaturated) including a part of the mother nucleus (i.e., including the nitrogen atom to which $R^8$ is attached and the carbon atom to which $X^2$ is attached). The thus formed ring may contain an oxygen, nitrogen or sulfur atom as a ring constituting atom and may further have an alkyl group having 1 to 6 carbon atoms as a substituent.

When $A^2$ is a partial structure represented by formula (V):

(V)

$X^4$ is a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms. The amino group may have at least one substituent selected from the group consisting of a formyl group, an alkyl group having 1 to 6 carbon atoms and an acyl group having 2 to 5 carbon atoms.

The alkyl group may be either a straight- or branched-chain having 1 to 6 carbon atoms and is preferably a methyl or ethyl group. The alkenyl group may be either a straight- or branched-chain having 2 to 6 carbon atoms and is preferably a vinyl group. The alkynyl group may be either a straight- or branched-chain having 2 to 6 carbon atoms and is preferably an ethynyl group. As the halogen of the halogenomethyl group, fluorine is particularly preferred, and the number of fluorine atoms may be 1 to 3. The alkoxyl group may have 1 to 6 carbon atoms and is preferably a methoxyl group. As the halogen of the halogenomethoxyl group, fluorine is particularly preferred, and the number of fluorine atoms may be 1 to 3.

In addition, $X^4$ and $R^{11}$ may be combined to form a cyclic structure (the ring may have a ring size of from a four-membered to a seven-membered ring which may be saturated, partially saturated or unsaturated) including a part of the mother nucleus (i.e., including the nitrogen atom to which $R^{11}$ is attached and the carbon atom to which $X^4$ is attached). The thus formed ring may contain an oxygen, nitrogen or sulfur atom as a constituent ring member, and may further have an alkyl group having 1 to 6 carbon atoms as a substituent.

When $A^1$ is a partial structure represented by formula (III):

(III)

a preferred combination of $R^{10}$ and $X^2$ is where $R^{10}$ is an amino group, a hydrogen atom, a hydroxyl group or an alkyl group having 1 to 6 carbon atoms and $X^2$ is an alkyl group having 1 to 6 carbon atoms, an alkoxyl group having 1 to 6 carbon atoms, a halogen atom, a halogenomethoxyl group or a hydrogen atom.

In a more preferred combination, $R^{10}$ is an amino group, a hydrogen atom, a hydroxyl group or a methyl group and $X^2$ is a methyl group, a methoxyl group, a fluorine atom, a chlorine atom, a difluoromethoxyl group or a hydrogen atom.

In a most preferred combination, $R^{10}$ is an amino group, a hydrogen atom, a hydroxyl group or a methyl group and $X^2$ is a methyl group or a methoxyl group.

For these combinations of $R^{10}$ and $X^2$, $X^1$ is preferably a fluorine atom.

When the substituents $X^1$ and $X^2$ each independently represents a halogen atom, a fluorine atom is particularly preferred as $X^1$ and a fluorine or chlorine atom is desirable as $X^2$.

When $A^2$ is a partial structure represented by formula (V):

(V)

a preferred combination of $R^{12}$ and $X^4$ is where $R^{12}$ is an amino group, a hydrogen atom, a hydroxyl group or an alkyl group having 1 to 6 carbon atoms and $X^4$ is an alkyl group having 1 to 6 carbon atoms, an alkoxyl group having 1 to 6 carbon atoms, a halogen atom, a halogenomethoxyl group or a hydrogen atom.

In a more preferred combination, $R^{12}$ is an amino group, a hydrogen atom, a hydroxyl group or a methyl group and $X^4$ is a methyl group, a methoxyl group, a fluorine atom, a chlorine atom, a difluoromethoxyl group or a hydrogen atom.

In a most preferred combination, $R^{12}$ is an amino group, a hydrogen atom, a hydroxyl group or a methyl group and $X^4$ is a methyl group or a methoxyl group.

When the substituents $X^3$ and $X^4$ each independently represents a halogen atom, a fluorine atom is particularly preferred as $X^3$ and a fluorine or chlorine atom is desirable as $X^4$.

Next, the halogenocyclopropyl group represented by $R^8$ is described below.

Examples of the halogen atom include a fluorine atom and a chlorine atom, and a fluorine atom is particularly preferred.

With regard to the stereochemical environment of this moiety, it is particularly preferred that the halogen atom and the pyridonecarboxylic acid moiety take a cis-configuration with respect to the cyclopropane ring.

Enantiomerical isomers can exist solely due to this cis-2-halogenocyclopropyl moiety of $R^8$, and strong antibacterial activity and high safety have been confirmed in both of these isomers.

The compound of the first aspect of the present invention represented by formula (I) can be produced by various methods, for example, by a preferred method in which a compound represented by formula (VI):

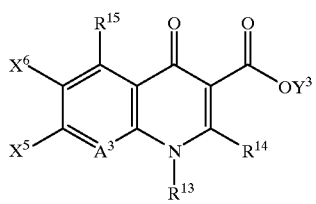

(VI)

[wherein $X^5$ is a substituent which serves as a leaving group, such as a fluorine atom, a chlorine atom, a bromine atom, a substituted or unsubstituted phenylsulfonyl group or a substituted or unsubstituted alkylsulfonyl group having 1 to 3 carbon atoms;

$Y^3$ is the $Y^1$ as defined in formula (II) or a group represented by formula (VII):

(VII)

(wherein each of $Y^{31}$ and $Y^{32}$ is a fluorine atom or an alkylcarbonyloxy group having 2 to 5 carbon atoms), and $R^{13}, R^{14}, R^{15}, A^3$ and $X^6$ are the same groups corresponding to $R^8, R^9, R^{10}, A^1$ and $X^1$ as defined in formula (II)] or a compound represented by formula (VIII):

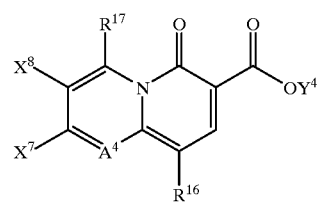

(VIII)

[wherein $X^7$ is a substituent which serves as a leaving group, such as a fluorine atom, a chlorine atom, a bromine atom, a substituted or unsubstituted phenylsulfonyl group or a substituted or unsubstituted alkylsulfonyl group having 1 to 3 carbon atoms, and $R^{16}, R^{17}, A^4, X^8$ and $Y^4$ are the same groups corresponding to $R^{11}, R^{12}, A^2, X^3$ and $Y^2$ as defined in formula (IV)] is allowed to react with a compound represented by formula (IX):

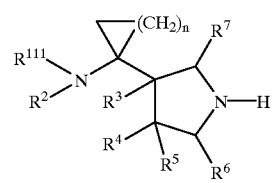

(IX)

[wherein $R^{111}$ is the $R^1$ defined in formula (I) or a protective group of the amino group and $R^2, R^3, R^4, R^5, R^6, R^7$ and n are as defined in formula (I)] or with an acid addition salt thereof.

The reaction can be carried out with or without a solvent. Examples of the solvent for use in the reaction include those which are inert under the reaction conditions, such as dimethyl sulfoxide, pyridine, acetonitrile, ethanol, chloroform, dimethylformamide, dimethylacetamide, N-methylpyrrolidone, tetrahydrofuran, water, 3-methoxybutanol and mixtures thereof.

It is preferable to carry out the reaction in the presence of an inorganic base, an organic base or the like acid receptor, such as an alkali metal or alkaline earth metal carbonate or bicarbonate, or triethylamine, pyridine, 1,8-diazabicycloundecene or the like.

The reaction temperature may be generally within the range of from room temperature to 200° C., but preferably within the range of approximately from 25 to 150° C. The reaction time may be 15 minutes to 48 hours, and the reaction is completed generally within 30 minutes to 2 hours.

Illustrative examples of the amino group-protecting group are those which are generally used for this purpose, which include alkoxycarbonyl groups such as tert-butoxycarbonyl, 2,2,2-trichloroethoxycarbonyl and the like, aralkyloxycarbonyl groups such as benzyloxycarbonyl, p-methoxybenzyloxycarbonyl, p-nitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tert-butyl, benzyl, p-nitrobenzyl, p-methoxybenzyl, triphenylmethyl and the like, ethers such as methoxymethyl, tert-butoxymethyl, tetrahydropyranyl, 2,2,2-trichloroethoxymethyl and the like, and silyl groups such as trimethylsilyl, isopropyldimethylsilyl, tert-butyldimethylsilyl, tribenzylsilyl, tert-butyldiphenylsilyl and the like.

When $Y^3$ and $Y^4$ are each an alkyl group having 1 to 6 carbon atoms, an alkoxymethyl group having 2 to 7 carbon atoms or a phenylalkyl group which is composed of an alkylene group having 1 to 6 carbon atoms and phenyl group, conversion into the corresponding carboxylic acid can be effected by treatment under acidic or basic conditions generally used for the hydrolysis of carboxylic acid esters.

When $Y^3$ has a structure represented by formula (VII):

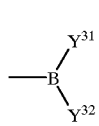

(VII)

conversion into the corresponding carboxylic acid can be effected by carrying out the reaction of the compound (VI) with the compound (IX) and then treating under acidic or basic conditions.

In addition, when deprotection is required, the compound of interest represented by formula (I) can be obtained by removing protective groups under an appropriate procedure known in the art corresponding to the protective groups which are used.

The second aspect of the present invention is described in detail below.

The substituents of the compounds of the second aspect of the present invention represented by formula (XI) are described below as follows.

The substituent $R^1$ represents a hydrogen atom or an alkyl group having 1 to 6 carbon atoms. This alkyl group may be either a liner or branched one having 1 to 6 carbon atoms. Preferable examples thereof include methyl, ethyl, n-propyl and isopropyl groups.

$R^2$ represents a hydrogen atom or an alkyl group having 1 to 6 carbon atoms. This alkyl group may have one or more substituents selected from the group consisting of a hydroxyl group, a halogen atom, an alkylthio group having 1 to 6 carbon atoms and an alkoxyl group having 1 to 6 carbon atoms.

This alkyl group may be either a liner or branched group having 1 to 6 carbon atoms. Preferable examples thereof include methyl, ethyl, n-propyl and isopropyl groups.

When this alkyl group is substituted by a hydroxyl group, the alkyl group may be either a linear or branched one having 1 to 6 carbon atoms and the hydroxyl group is preferably attached to the terminal carbon atom of the alkyl group. Preferable examples of the alkyl group having a hydroxyl group include hydroxymethyl, 2-hydroxyethyl, 2-hydroxypropyl and 3-hydroxypropyl groups.

When this alkyl group is substituted by a halogen atom, the alkyl group may be either a linear or branched one having 1 to 6 carbon atoms and a fluorine atom is preferable as the halogen atom.

When this alkyl group is substituted by an alkylthio group, the alkyl group may be either a linear or branched one having 1 to 6 carbon atoms. Also, the alkylthio group may be either a linear or branched one having 1 to 6 carbon atoms. Examples of the alkyl group having an alkylthio group include alkylthiomethyl, alkykthioethyl and alkylthiopropyl groups. The alkylthio group preferably has up to 3 carbon atoms. Namely, more preferred examples thereof include methylthiomethyl, ethylthiomethyl and methylthioethyl groups.

When this alkyl group is substituted by an alkoxyl group, the alkyl group may be either a linear or branched one having 1 to 6 carbon atoms. Also, the alkoxyl group may be either a linear or branched one having 1 to 6 carbon atoms. Examples of the alkyl group having an alkoxyl group include alkoxymethyl, alkoxethyl and alkoxypropyl groups. The alkoxyl group preferably has up to 3 carbon atoms. Namely, more preferred examples thereof include methoxymethyl, ethoxymethyl and methoxyethyl groups.

The substituents $R^3$ and $R^5$ each represents a hydrogen atom. These hydrogen atoms are located in the cis-configuration with regard to the pyrrolidine ring.

The substituent $R^4$ represents a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms. This alkyl group may have one or more substituents selected from the group consisting of a hydroxyl group, a halogen atom and an alkoxy group having 1 to 6 carbon atoms.

Preferable examples of the halogen atom are fluorine and chlorine atoms.

Although the alkyl group may be either a linear or branched one having 1 to 6 carbon atoms, preferable examples thereof include methyl, ethyl, n-propyl and iso-propyl groups.

Although the alkoxyl group may be either a linear or branched one having 1 to 6 carbon atoms, preferable examples thereof include methoxyl and ethoxyl groups.

Although the alkylthio group may be either a linear or branched one having 1 to 6 carbon atoms, preferable examples thereof include methylthio and ethylthio groups.

When this alkyl group is substituted by a hydroxyl group, the alkyl group may be either a linear or branched one having 1 to 6 carbon atoms, and the hydroxyl group is preferably attached to the terminal carbon atom of the alkyl group. Preferable examples of the hydroxylated alkyl group having 1 to 6 carbon atoms include hydroxymethyl, 2-hydroxyethyl and 3-hydroxypropyl groups.

When this alkyl group is substituted by a halogen atom, preferable examples of the halogen atom include fluorine and chlorine atoms, and a fluorine atom is more preferable. The alkyl group may be either a linear or branched one having 1 to 6 carbon atoms.

When this alkyl group having 1 to 6 carbon atoms is substituted by an alkoxyl group, each alkyl moiety may be either a linear or branched one having 1 to 6 carbon atoms. Preferable examples thereof include alkoxymethyl or alkoxethyl groups and methoxymethyl, ethoxymethyl and 2-methoxyethyl groups are yet more preferable.

The substituent $R^4$ and the substituent on the pyrrolidine ring of the following formula:

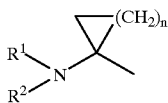

are located in the cis-configuration, which is one of the characteristics of the second aspect of the present invention.

The substituents $R^6$ and $R^7$ each independently represents a hydrogen atom or an alkyl group having 1 to 6 carbon atoms. Although the alkyl group may be either a linear or branched one having 1 to 6 carbon atoms, preferable examples thereof include methyl, ethyl, n-propyl and isopropyl groups.

n is an integer of from 1 to 3. Namely, the ring may range from a cyclopropane ring to a cyclopentane ring. In the compounds of the second aspect of the present invention, this moiety has a cyclic structure, which is another characteristic of the second aspect of the present invention. It is particularly preferable that n is 1.

Q is a partial structure of a fused heterocycle represented by the following formula:

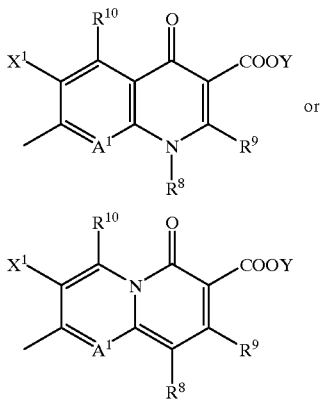

The substituent $R^8$ represents an alkyl group having 1 to 6 carbon atoms, an alkenyl group having 2 to 6 carbon atoms, a halogenoalkyl group having 1 to 6 carbon atoms, a substituted or unsubstituted cyclic alkyl group having 3 to 6 carbon atoms; a substituted or unsubstituted aryl group, a substituted or unsubstituted heteroaryl group, an alkoxyl group having 1 to 6 carbon atoms or an alkylamino group having 1 to 6 carbon atoms.

An ethyl group is particularly preferable as the alkyl group having 1 to 6 carbon atoms. A vinyl or 1-isopropenyl group is preferable as the alkenyl group having 2 to 6 carbon atoms. A 2-fluoroethyl group is preferable as the halogenoalkyl group having 1 to 6 carbon atoms. A cyclopropyl and 2-halogenocyclopropyl groups are preferable as the substituted or unsubstituted cyclic alkyl group having 3 to 6 carbon atoms. As the halogen atom in the 2-halogenocyclopropyl group, a fluorine atom is preferable in particular.

Examples of the substituted or unsubstituted aryl group include a phenyl group, etc., optionally having 1 to 3 substituents selected from the group consisting of a halogen atom (e.g., fluorine, chlorine or bromine), a lower alkyl group having 1 to 6 carbon atoms, a hydroxyl group, an amino group, a nitro group, a lower alkoxyl group having 1 to 6 carbon atoms, etc. Preferable examples thereof include phenyl, 2-fluorophenyl, 4-fluorophenyl, 2,4-difluorophenyl and 2-fluoro-4-hydroxyphenyl groups.

A heteroaryl group is a substituent derived from an aromatic heterocyclic compound containing at least one heteroatom selected from among nitrogen, oxygen and sulfur atoms. Examples thereof include pyridyl and pyrimidyl groups. Preferable examples of the substituents on these rings include an alkyl group and a halogen atom. A methoxyl group is preferable as the alkoxyl group having 1 to 6 carbon atoms, while a methylamino group is preferable as the alkylamino group having 1 to 6 carbon atoms.

Preferable examples of the substituent $R^8$ include a cyclic alkyl group and a halogenocycloalkyl group. Among these substituents, a cyclopropyl group or a 2-halogenocyclopropyl group is preferable therefor. As the halogen atom, a fluorine atom is preferable.

The substituent $R^9$ represents a hydrogen atom or an alkylthio group having 1 to 6 carbon atoms. Alternatively, $R^9$ and $R^8$ may form together with a part of the mother nucleus (containing the nitrogen atom to which $R^8$ is bonded and the carbon atom to which $R^9$ is bonded) a cyclic structure. The ring thus formed may contain a sulfur atom as a constituent atom thereof and have an alkyl group having 1 to 6 carbon atoms as a substituent. The ring thus formed is a 4- to 6-membered one which is either saturated, partly saturated or unsaturated.

The substituent $X^1$ represents a halogen atom or a hydrogen atom. When it is a halogen atom, a fluorine atom is preferable therefor. Among all, a fluorine or hydrogen atom is preferable as this substituent.

The substituent $R^{10}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms. The amino group may have one or more substituents selected from the group consisting of a formyl group, an alkyl group having 1 to 6 carbon atoms and an acyl group having 2 to 5 carbon atoms.

Although the alkyl group may be either a linear or branched one having 1 to 6 carbon atoms, preferable examples thereof include methyl, ethyl, n-propyl and isopropyl groups. The alkenyl group is a linear or branched one having 2 to 6 carbon atoms and a vinyl group is preferable therefor. Although the alkynyl group may be either a linear or branched one having 2 to 6 carbon atoms, an ethynyl group is preferable therefor. One to three fluorine atoms are particularly preferable as the halogen in the haolenomethyl group. Although the alkoxyl group may be one having 1 to 6 carbon atoms, a methoxymethyl group is preferable therefor.

Preferable examples of the substituent $R^{10}$ include alkyl and amino groups. Among all, a methyl group and an unsubstituted amino group are particularly preferable therefor.

When the substituent $R^{10}$ is an amino, a hydroxyl group or a thiol group, it may be protected by protective groups usually employed in the art.

Examples of such protective groups include alkoxycarbonyl groups (e.g., tert-butoxycarbonyl and 2,2,2-trichloroethoxycarbonyl), aralkyloxycarbonyl groups (e.g., benzyloxcarbonyl, p-methoxybenzyloxycarbonyl and p-nitrobenzyloxycarbonyl), acyl groups (e.g., acetyl, methoxyacetyl, trifluoroacetyl, chloroacetyl, pivaloyl, formyl and benzoyl), alkyl or aralkyl groups (e.g., tert-butyl, benzyl, p-nitrobenzyl, p-methoxybenzyl and triphenylmethyl), ethers (e.g., methoxymethyl, tert-butoxymethyl, tetrahydropyranyl and 2,2,2-trichloroethoxymethyl) and substituted silyl groups (e.g., trimethylsilyl, isopropyldimethylsilyl, tert-butyldimethylsilyl, tribenzylsily, and tert-butyldiphenylsilyl). Compounds carrying substituents protected by these groups are preferable particularly as intermediates in production processes.

When $A^1$ represents a partial structure represented by the following formula (XII):

(XII)

$X^2$ represents a hydrogen atom, an amino group, a halogen atom, a cyano group, a halogenomethyl group, a halogenomethoxy group, an alkyl group having 1 to 6 carbon atoms, an alkenyl group having 2 to 6 carbon atoms, an alkynyl group having 2 to 6 carbon atoms or an alkoxyl group having 1 to 6 carbon atoms. The amino group may have one or more substituents selected from the group consisting of a formyl group, an alkyl group having 1 to 6 carbon atoms and an acyl group having 2 to 5 carbon atoms.

Although the alkyl group may be either a linear or branched one having 1 to 6 carbon atoms, methyl and ethyl groups are preferable therefor. Although the alkenyl group may be either a linear or branched one having 2 to 6 carbon atoms, a vinyl group is preferable therefor. Although the alkynyl group may be either a linear or branched one having 2 to 6 carbon atoms, an ethynyl group is preferable therefor. One to three fluorine atoms are particularly preferable as the halogen in the halogenomethyl group. Although the alkoxyl group may be one having 1 to 6 carbon atoms, a methoxyl group is preferable therefor. One to three fluorine atoms are particularly preferable as the halogen in the halogenomethoxyl group.

Among these substituents, an alkyl or alkoxyl group is preferable, and methyl and methoxyl groups are yet more preferable.

$X^2$ and $R^8$ may form together with a part of the mother nucleus (containing the nitrogen atom to which $R^8$ is bonded and the carbon atoms to which $X^2$ is bonded) a cyclic structure which is a 4- to 7-membered ring which may be saturated, partly saturated or unsaturated. This ring may contain an oxygen atom, a nitrogen atom or a sulfur atom as a constitutent atom thereof, and optionally has an alkyl group having 1 to 6 carbon atoms as a substituent.

An example of the fused ring system thus formed is 2,3-dihydro-7-oxo-7H-pyrido[1,2,3-de][1,4]benzoxazin-6-carboxylic acid structure, and the 3(S)-methyl compound is particularly preferable.

When $A^1$ is a partial structure represented by the following formula:

, examples of preferable combinations of $R^{10}$ with $X^2$ include those wherein $R^{10}$ is an amino group, a hydrogen atom, a hydroxyl group or an alkyl group having 1 to 6 carbon atoms and $X^2$ is an alkyl group having 1 to 6 carbon atoms, an alkoxyl group having 1 to 6 carbon atoms, a halogen atom, a halogenomethoxyl group or a hydrogen atom.

Examples of yet more preferable combinations thereof are those wherein $R^{10}$ is an amino group, a hydrogen atom, a hydroxyl group or a methyl group and $X^2$ is a methyl group, a methoxyl group, a fluorine atom, a chlorine atom, a difluoromethoxyl group or a hydrogen atom.

Examples of particularly preferable combinations thereof are those wherein $R^{10}$ is an amino group, a hydrogen atom, a hydroxyl group or a methyl group and $X^2$ is a methyl group or a methoxyl group.

Preferable examples of $R^{10}$ and $X^2$ are given above. On the other hand, a fluorine atom is preferable as $X^1$.

When the substituents $X^1$ and $X^2$ are each a halogen atom, it is particularly preferable that $X^1$ is a fluorine atom and $X^2$ is a fluorine or chlorine atom.

Next, the halogenocyclopropyl group represented by $R^8$ is explained below.

Examples of the halogen atom as the substituent include fluorine and chlorine atoms, and a fluorine atom is particularly preferable therefor.

With respect to the stereochemical environment in this moiety, it is particularly preferable that the halogen atom and the pyridonecarboxylate moiety are located at the cis-configuration with respect to the cyclopropane ring.

There are so-called antipodes with respect to the cis-2-halogenocyclopropyl moiety of $R^8$. These isomers each exhibit potent antimicrobial activity and high safety.

The compounds of the second aspect of the present invention exhibit excellent characteristics due to the substituent represented by the following formula (XIII) located on the pyrrolidine ring:

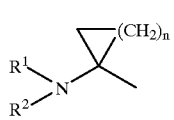

(XIII)

The compounds of the second aspect of the present invention are further characterized in that this substituent and the substituent $R^4$ are located in the cis-configuration. As a matter of course, the substituents $R^3$ and $R^5$ are also located in the cis-configuration. It has been confirmed that the compounds of the second aspect of the present invention have excellent safety characteristics because these substituents are located in the cis-configuration. That is to say, favorable properties such as a decrease in acute toxicity and a negative micronuclear test are thus achieved. Especially, it has been clarified that the compounds of the present invention, which are characterized in that the substituent of the formula (XIII) and the substituent $R^4$ are located in the cis-configuration, are superior in a decrease in the acute toxicity as compared with those compounds having the substituent of the formula (XIII) and the substituent $R^4$ in the trans-configuration.

The excellent safety characteristics of the compounds of the second aspect of the present invention are apparent when the cyclic moiety in the substituent represented by the formula (XIII) is a 3-membered ring. Also, these characteristics are apparent when the substituent $R^4$ is a fluorine atom. Preferable examples of the compounds according to the second aspect of the present invention include those compounds wherein n is 1 and the substituent $R^4$ is a fluorine atom.

In the compounds represented by the formula (XI) of the second aspect of the present invention, the substituent $R^4$ and the substituent having a cyclic structure are located at the cis-configuration. More particularly, the following two isomers occur with respect to this moiety:

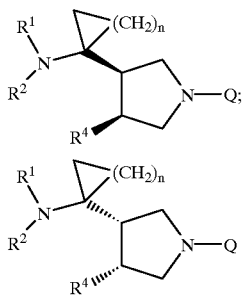

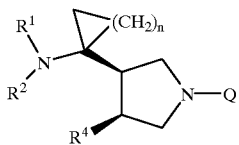

The present inventors consider that the isomer represented by the following formula is preferred to the other one:

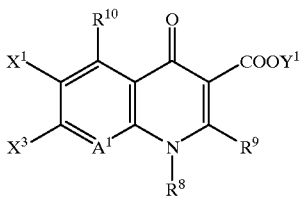

The compounds represented by the formula (XI) of the second aspect of the present invention can be produced by various methods. A preferable example thereof comprises reacting a compound represented by the following formula (XIV):

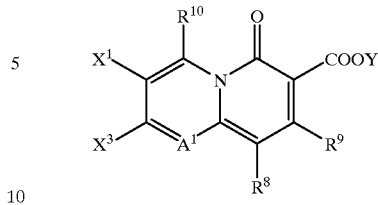

(XIV)

wherein $X^3$ represents a group serving as a leaving group such as a fluorine atom, a chlorine atom, a bromine atom, a substituted or unsubstituted phenylsulfonyl group or a substituted or unsubstituted alkylsulfonyl group having 1 to 3 carbon atoms;

$Y^1$ means Y as defined in the above formula (XI) or a boron-containing group represented by the following formula:

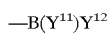
—B(Y$^{11}$)Y$^{12}$ wherein $Y^{11}$ and $Y^{12}$ each represents a fluorine atom or an alkylcarbonyloxy group having 2 to 4 carbon atoms; and $R^8, R^9, R^{10}, A^1$ and $X^1$ are as defined in the above formula (XI);

or a compound represented by the following formula:

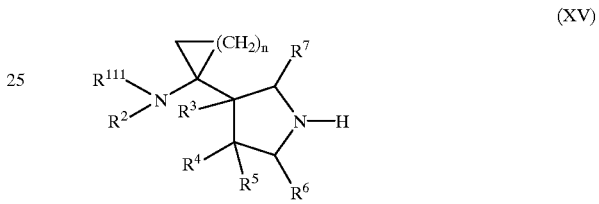

wherein $X^3$ represents a group serving as a leaving group such as a fluorine atom, a chlorine atom, a bromine atom, a substituted or unsabstuted phenylsulfonyl group or a substituted or unsubstituted alkylsulfonyl group having 1 to 3 carbon atoms; and $R^8, R^9, R^{10}, A^1, X^1$ and Y are as defined in the above formula (XI);

with a compound represented by the following formula (XV) or its acid addition salt:

(XV)

wherein $R^{111}$ has the same meaning as that of $R^1$ as defined in the above formula (XI) or represents a protective group for amino group; and $R^2, R^3, R^4, R^5, R^6, R^7$ and n are as defined in the above formula (XI);

provided that the substituent $R^4$ and the substituent containing the cyclic structure-bonded to the carbon atom adjacent to the carbon atom to which the substituent $R^4$ is bonded are located in the cis-configuration.

Examples of the acid addition salt include inorganic acid salts and organic acid salts. More particularly, inorganic acid salts (e.g., hydrochloride, sulfate, nitrate, hydrobromide, hydroiodide and phosphate) and organic acid salts (e.g., sulfonates such as methanesulfonate, benzenesulfonate and toluenesulfonate, and carboxylates such as acetate, citrate, maleate, fumarate and lactate) are exemplified.

The reaction may be performed with the use of a solvent or without using any solvent. Any solvent may be employed in the reaction, so long as it remains inert under the reaction conditions. For example, useful solvents include dimethyl sulfoxide, pyridine, acetonitrile, ethanol, chloroform, dimethylformamide, dimethylacetamide, N-methylpyrrolidone, tetrahydrofuran, water, 3-methoxybutanol and mixtures thereof.

The reaction is preferably performed in the presence of an acid acceptor such as an inorganic base or organic acid base (e.g., alkali metal or alkaline earth metal carbonate or hydrogencarbonate, triethylamine, pyridine or 1,8-diazabicyclundecene).

The reaction temperature usually ranges from room temperature to 200° C., preferably from about 25° C. to 150° C. The reaction is continued for 15 minutes to 48 hours. Usually, it may be completed within about 30 minutes to 15 hours.

The protective group for amino group may be one that is generally employed in the art. Examples thereof include optionally substituted alkoxycarbonyl groups (e.g., tert-butoxycarbonyl and 2,2,2-trichloroethoxycarbonyl), optionally substituted aralkyloxycarbonyl groups (e.g., benzyloxycarbonyl, p-methoxybenzyloxycarbony and p-nitrobenzyloxycarbonyl), optionally substituted acyl groups (e.g., acetyl, methoxyacetyl, trifluoroacetyl, chloroacetyl, pivaloyl, formyl and benzoyl), optionally substituted alkyl groups and optionally substituted aralkyl groups (e.g., tert-butyl, benzyl, p-nitrobenzyl, p-methoxybenzyl and triphenylmethyl), ethers (e.g., metoxymethyl, tert-butoxymethyl, tetrahydropyranyl and 2,2,2-trichloroethoxymethyl) and substituted silyl groups (e.g., trimethylsilyl, isopropyldimethylsilyl, tert-butyldimethylsilyl, tribenzylsilyl and tert-butyldiphenylsilyl).

When Y and $Y^1$ each represents an alkyl group having 1 to 6 carbon atoms, an alkoxymethyl group having 2 to 7 carbon atoms or a phenylalkyl group composed of an alkylene group having 1 to 6 carbon atoms with a phenyl group, the compound can be converted into the corresponding carboxylic acid by treating under acidic or basic conditions generally employed in the hydrolysis of carboxylates.

When $Y^1$ is a structure represented by the following formula:

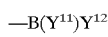

the compound of formula (XV) is reacted with the compound of formula (XIV) and then treated under acidic or basic conditions to thereby convert the reaction product into the corresponding carboxylic acid.

When deprotection is needed, the protective group is removed using an appropriate procedure known in the art for the protective group used to thereby give the target compound of the formula (XI).

The compound represented by the formula (XV) can be formed by removing Q' from a compound represented by the following formula:

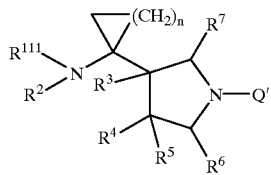

wherein $R^{111}$ represents a hydrogen atom, an alkyl group having 1 to 6 carbon atoms or a protective group for amino group;

$R^2$ represents a hydrogen atom or an alkyl group having 1 to 6 carbon atoms, provided that the alkyl group may have one or more substituents selected from the group consisting of a hydroxyl group-a halogen atom and an alkoxy group having 1 to 6 carbon atoms;

$R^3$ and $R^5$ each represents a hydrogen atom;

$R^4$ represents a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, provided that the alkyl group may have one or more substituents selected from the group consisting of a hydroxyl group, a halogen atom and an alkoxy group having 1 to 6 carbon atoms; and $R^4$ and the substituent on the pyrrolidine ring of the following formula:

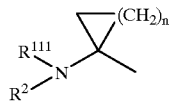

are located in the cis-configuration (as a matter of course, the substituents $R^3$ and $R^5$ are also located at the cis-configuration);

$R^6$ and $R^7$ each independently represents a hydrogen atom or an alkyl group having 1 to 6 carbon atoms;

n is an integer of from 1 to 3; and

Q' represents an amino-protective group selected from the group consisting of optionally substituted alkoxycarbonyl groups, optionally substituted aralkyloxycarbonyl groups, optionally substituted acyl groups, optionally substituted alkyl groups, optionally substituted aralkyl groups and substituted silyl groups.

This compound having Q' moiety may occur as a salt or hydrate thereof or as a hydrate of the salt. Examples of the acid addition salts include inorganic acid salts and organic acid salts. More particularly, inorganic acid salts (e.g., hydrochloride, sulfate, nitrate, hydrobromide, hydroiodide and phosphate) and organic acid salts (e.g., sulfonates such as methanesulfonate, benzenesulfonate and toluenesulfonate, and carboxylates such as acetate, citrate, maleate, fumarate and lactate) are exemplified.

When $R^{111}$ and Q' are both protective groups for amino group, they may be either the same or different from each other. To produce the compound of formula (XI), it is advantageous that these amino-protective groups are those which are removed under different reaction conditions.

Examples of the protective groups for $R^{111}$ and Q' include optionally substituted alkoxycarbonyl groups, optionally substituted aralkyloxycarbonyl groups, optionally substituted acyl groups, optionally substituted alkyl groups, optionally substituted aralkyl groups and substituted silyl groups.

Particular examples thereof include optionally substituted alkoxycarbonyl groups (e.g., tert-butoxycarbonyl and 2,2,2-trichloroethoxycarbonyl), optionally substituted aralkyloxycarbonyl groups (e.g., benzyloxycarbonyl, p-methoxybenzyloxycarbony and p-nitrobenzyloxycarbonyl), optionally substituted acyl groups (e.g., acetyl, methoxyacetyl, trifluoroacetyl, chloroacetyl, pivaloyl, formyl and benzoyl), optionally substituted alkyl groups and optionally substituted aralkyl groups (e.g., tert-butyl, benzyl, p-nitrobenzyl, p-methoxybenzyl and triphenylmethyl), ethers (e.g., metoxymethyl, tert-butoxymethyl, tetrahydropyranyl and 2,2,2-trichloroethoxymethyl) and substituted silyl groups (e.g., trimethylsilyl, isopropyldimethylsilyl, tert-butyldimethylsilyl, tribenzylsilyl and tert-butyldiphenylsilyl).

The compound of the formula (XV) can be produced as a cis-compound by forming a compound (pyrroline derivative) wherein the carbon atom to which the substituent $R^4$ is bonded and the adjacent carbon atom is bonded via a double bond followed by catalytic reduction. Alternatively, the cis-compound can be produced by once forming a compound wherein the substituent $R^4$ and the substituent moiety having the cyclic structure are located at the trans-configuration and then inverting the configuration of the substituent $R^4$.

When the compound represented by formula (I) or formula (XI) according to the first and second aspects of the present invention has a structure allowing for the existence of diastereomers, it is preferable that a compound comprised of a single diastereomer is administered to human beings or animals. The term "comprised of a single diastereomer" as used herein means not only one being completely free from other diastereomers, but also one having a certain degree of chemically purity. That is to say, it may contain other diastereomers so long as neither the physical constants nor the physiological activities thereof are affected thereby.

Also, the term "stereochemically pure" as used herein means a compound consisting of one of the isomers, when the compound has two or more isomers due to one or more asymmetric carbon atoms contained therein. The term "pure" of this case can be understood in the same manner as the abovementioned case.

The pyridonecarboxylic acid derivatives of the first and second aspect of the present invention may be in a free state. Alternatively, they may be converted into acid addition salts or carboxylates thereof. Examples of the acid addition salts include inorganic acid salts (e.g., hydrochloride, sulfate, nitrate, hydrobromide, hydroiodide and phosphate) and organic acid salts (e.g., acetate, methanesulfonate, benzenesulfonate, toluenesulfonate, citrate, maleate, fumarate and lactate).

Examples of the carboxylates include alkali metal salts (e.g., lithium salt, sodium salt and potassium salt), alkaline earth metal salts (e.g., magnesium salt and calcium salt), ammonium salt, triethylamine salt, N-methylglucamine salt and tris-(hydroxymethyl)aminomethane salt. Either inorganic salts or organic salts are usable therefor.

These free pyridonecarboxylic acid derivatives or their acid addition salts or-carboxylates may occur as hydrates thereof.

On the other hand, quinolone derivatives wherein the carboxylate moiety is an ester are useful as intermediates for synthesis or as prodrugs. For example, alkyl esters, benzyl esters, alkoxyalkyl esters, phenylalkyl esters and phenyl esters are useful as synthetic intermediates.

The esters usable as prodrugs are those which are easily cleaved in vivo to thereby form free carboxylates. Examples thereof include acetoxymethyl ester, pivaloyloxymethyl ester, ethoxycarbonyl ester, choline ester, dimethylaminoethyl ester, 5-indanyl ester and oxoalkyl esters such as phthalidinyl ester, 5-alkyl-2-oxo-1,3-dioxol-4-ylmethyl ether and 3-acetoxy-2-oxobutyl ester and the like.

Because the compounds of the first and second aspects of the present invention possess strong antibacterial and antimicrobial activities, they find versatile use in applications such as pharmaceutical preparations for humans, animals and fish, or as agricultural chemicals and food preservatives.

When the compounds of the first and second aspects of the present invention are used as pharmaceutical preparations for humans, the dose may be within the range of from 50 mg to 1 g, preferably from 100 mg to 300 mg, per day per adult.

When used in animals, its dose varies depending on the object of administration (healing or prevention for example), species and size of each animal to be treated, species of the infected pathogenic bacterium and degree of the infection, but its daily dose may be within the range of generally from 1 mg to 200 mg, preferably from 5 mg to 100 mg, per 1 kg body weight.

The daily dose may be administered once a day or by dividing it into 2 to 4 doses. If necessary, the daily dose may be increased by exceeding the above range.

Because the compounds of the first and second aspects of the present invention are active upon a broad range of microorganisms which cause various infectious diseases, they are effective in treating, preventing or alleviating diseases caused by these pathogens.

Examples of bacteria or bacteria-like microorganisms to be treated by the compounds of the first and second aspects of the present invention include the genus Staphylococcus, *Streptococcus pyogenes,* hemolytic streptococci, enterococcus, pneumococcus, the genus Peptostreptococcus, *Neisseria gonorrhoeae, Escherichia coli,* the genus Citrobacter, the genus Shigella, *Klebsiella pneumoniae,* the genus Enterobacter, the genus Serratia, the genus Proteus, *Pseudomonas aeruginosa, Haemophilus influenzae,* the genus Acinetobacter, the genus Campylobacter, *Chlamydia trachomatis* and the like.

Examples of diseases induced by these pathogens include folliculitis, furuncle, carbuncle, erysipelas, phlegmon, lymphangitis (lymphadenitis), felon, subcutaneous abscess, hidradenitis, acne conglobata, infectious atheroma, perirectal asscess, mastitis, superficial secondary infections such as of injury, burn injury, operative wound and the like, pharyngitis, laryngitis, acute bronchitis, tonsilitis, chronic bronchitis, bronchiectasis, diffuse bronchiolitis, secondary infection of chronic respiratory disease, pneumonia, pyelonephritis, cystitis, prostatitis, epididymitis, gonococcal urethritis, nonspecific urethritis, cholecystitis, cholangitis, bacillary dystentery, enteritis, uterine adnexitis, intrauterine infection, bartholinitis, blepharitis, hordeolum, dacryocystitis, tarsadenitis, corneal ulcer, otitis media, sinusitis, periodontitis, pericoronitis, jaw inflammation, peritonitis, endocarditis, sepsis, meningitis, skin infection and the like.

The compounds of the first and second aspects of the present invention are also effective against various microorganisms which cause infectious diseases of animals, such as the genera Escherichia, Salmonella, Pasteurella, Haemophilus, Bordetella, Staphylococcus, Mycoplasma and the like. Illustrative examples of such diseases include colibacillosis, pullorum, avian paratyphoid, avian cholera, infectious coryza, staphylococcosis, Mycoplasma infection and the like in the case of birds, colibacillosis, salmonellosis, pasteurellosis, Haemophilus infection, atrophic rhinitis, exudative epidermitis, Mycoplasma infection and the like in the case of pigs, colibacillosis, salmonellosis, hemorrhagic sepsis, Mycoplasma infection, bovine pleuropneumonia, mastitis and the like in the case of cattle, colisepsis, Salmonella infection, hemorrhagic sepsis, uterine empyema, cystitis and the like in the case of dogs, and exudative pleurisy, cystitis, chronic rhinitis, Haemophilus infection, kitten diarrhea, Mycoplasma infection and the like in the case of cats.

The antibacterial or antimicrobial preparations which contain a compound of the first and second aspects of the present invention can be prepared by selecting an appropriate dosage form corresponding to each administration method, and by making use of various commonly used medicine preparation methods. Examples of the dosage form of the antibacterial or antimicrobial preparations which contain a compound of the first and second aspects of the present invention as its principal agent include oral preparations such as tablets, powders, granules, capsules, solutions, syrups, elixirs, oily or aqueous suspensions and the-like.

When used in the form of an injection, stabilizing agents, antiseptics, solubilizing agents and the like may be used in the preparations, and the solution which may contain these auxiliary agents may be packed in containers and freeze-dried to make it into a solid preparation which is re-dissolved prior to use. Also, one dose may be packed in one container or multiple doses may be put in the same container.

Examples of external preparations include solutions, suspensions, emulsions, ointments, gels, creams, lotions, sprays and the like.

Solid preparations can be prepared by mixing the active compound with pharmaceutically acceptable additive agents optionally selected from fillers and extenders, binders, disintegrators, solubilizing agents, moistening agents, lubricating agents and the like.

Examples of liquid preparations include solutions, suspensions, emulsions and the like which may contain suspending agents, emulsifying agents and the like additives.

Administration of the compound of the first and second aspects of the present invention to animals may be effected by a method in which the compound is orally administered directly or after mixing it with feed, a method in which the compound is made into a solution and then orally administered directly or by adding the solution to drinking water or feed, or a method in which the compound is administered by injection.

With regard to pharmaceutical preparations of the compound of the first and second aspects of the present invention for use in their administration to animals, the compound may be optionally made into powders, fine subtilaes, soluble powders, syrups, solutions or injections making use of the techniques conventionally used in this field.

The following shows formulation examples of the pharmaceutical preparations.

| Formulation Example 1 [capsules]: | |
|---|---|
| Compound of Inventive Example 3 | 100.0 mg |
| Corn starch | 23.0 mg |
| CMC calcium | 22.5 mg |
| Hydroxymethylcellulose | 3.0 mg |
| Magnesium stearate | 1.5 mg |
| Total | 150.0 mg |
| Formulation Example 2 [solutions]: | |
| Compound of Inventive Example 5 | 1–10 g |
| Acetic acid or sodium hydroxide | 0.5–2 g |
| Ethyl paraoxybenzoate | 0.1 g |
| Purified water | 88.9–98.4 g |
| Total | 100 g |
| Formulation Example 3 [powders for mixing with feed]: | |
| Compound of Inventive Example 7 | 1–10 g |
| Corn starch | 98.5–89.5 g |
| Soft silicic anhydride | 0.5 g |
| Total | 100 g |
| Formulation Example 4 [capsules]: | |
| Compound of Inventive Example 16 | 100.0 mg |
| Corn starch | 23.0 mg |
| CMC calcium | 22.5 mg |
| Hydroxymethylcellulose | 3.0 mg |
| Magnesium stearate | 1.5 mg |
| Total | 150.0 mg |
| Formulation Example 5 [solutions]: | |
| Compound of Inventive Example 18 | 1–10 g |
| Acetic acid or sodium hydroxide | 0.5–2 g |
| Ethyl parahydoxybenzoate | 0.1 g |
| Purified water | 87.9–98.4 g |
| Total | 100 g |

| -continued | |
|---|---|
| Formulation Example 6 [powders for mixing with feed]: | |
| Compound of Inventive Example 20 | 1–10 g |
| Corn starch | 98.5–89.5 g |
| Soft silicic anhydride | 0.5 g |
| Total | 100 g |

EXAMPLES

Examples of the first and second aspects of the present invention are given below by way of illustration and not by way of limitation. In-this regard, the antibacterial and antimicrobial activities of the compounds of interest were measured in accordance with the standard method specified by the Japan Society of Chemotherapy. The results are shown in Tables 1 to 5 as a minimum inhibitory concentration (MIC,$\mu$g/ml). Unless otherwise indicated, all percents (%) are by weight.

The following are working examples in accordance with the first aspect of this invention.

Reference Example 1-1

(E)-Ethyl 3-(1-tert-butoxycarbonylaminocyclopropyl)propenoate

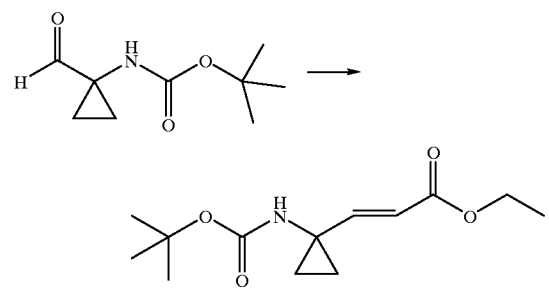

1-Tert-butoxycarbonylaminocyclopropane carbaldehyde (10.99 g, 59.3 mmol) and (carbethoxymethylene) triphenylphosphorane (27.6 g, 75.2 mmol) were dissolved in dichloromethane (300 ml) and heated under reflux for 4 hours. After evaporating the solvent, the resulting residue was applied to a silica gel chromatography column and eluted with an eluant of n-hexane:ethyl acetate=9:1, to thereby obtain 9.23 g (61%) of the title compound.

$^1$H-NMR (400 MHz, CDCl$_3$) δ: 6.48 (1 H, d, J=15.62 Hz), 5.84 (1 H, d, J=15.62 Hz), 5.00 (1 H, brs), 4.18 (2 H, q, J=7.33 Hz), 1.45 (9 H, s), 1.28 (3 H, t, J=7.33 Hz), 1.28 (2 H, brs), 1.16 (2 H, brs).

Reference Example 1-2

Ethyl trans-1-benzyl-4-(1-tert-butoxycarbonylaminocycloprotyl)pyrrolidine-3-carboxylate

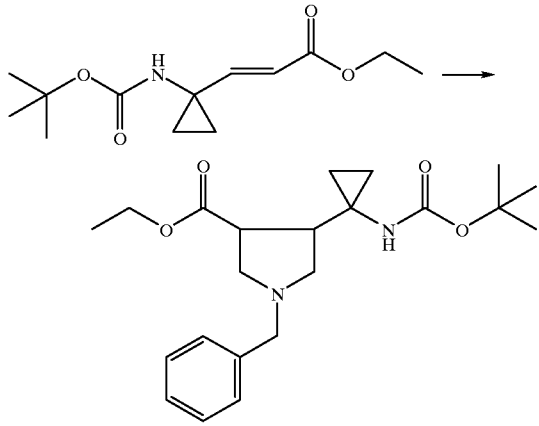

(E)-Ethyl 3-(1-tert-butoxycarbonylaminocyclopropyl) propenoate (2.91 g, 11.38 mmol) and N-benzyl-N-(n-butoxymethyl) trimethylsilylmethylamine (7.43 g, 26.59 mmol) were dissolved in dichloromethane (40 ml) and, under a nitrogen atmosphere, the solution was mixed with a 1 M dichloromethane solution of trifluoroacetic acid (2.66 ml, 2.66 mmol) and stirred at room temperature for 3 hours. After completing the reaction, the reaction solution was washed with a saturated sodium bicarbonate aqueous solution and a saturated sodium chloride aqueous solution in that order and dried over anhydrous sodium sulfate. After evaporating the solvent, the resulting residue was applied to a silica gel chromatography column and eluted with an eluant of n-hexane:ethyl acetate=2:1, and the resulting oily material was crystallized from chloroform-n-hexane to obtain 3.06 g (69%) of the title compound as white needle crystals.

$^1$H-NMR (400 MHz, CDCl$_3$) δ: 7.34–7.21 (5 H, m), 5.14 (1 H, brs), 4.13 (2 H, q, J=7.33 Hz), 3.60 and 3.56 (2 H, ABd, J=13.19 Hz), 3.21–3.11 (1 H, m), 2.87–2.76 (1 H, m), 2.75–2.64 (1 H, m), 2.55–2.45 (1 H, m), 2.43–2.33 (1 H, m), 1.43 (9 H, s), 1.25 (2 H, t, J=7.33 Hz), 0.98–0.88 (1 H, m), 0.86–0.73 (2 H, m), 0.72–0.63 (1 H, m).

Reference Example 1-3

Trans-1-benzyl-4-(1-tert-butoxycarbonylaminocyclopropyl)-3-hydroxymethyloyrrolidine

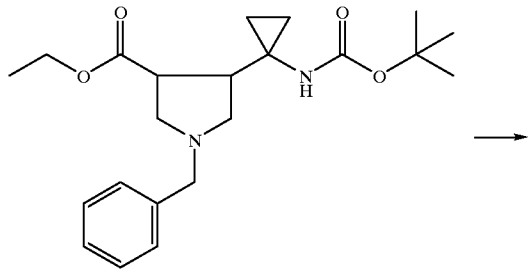

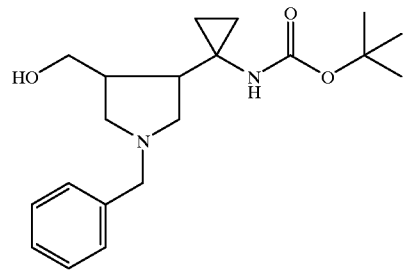

Under a nitrogen atmosphere, lithium aluminum hydride (381 mg, 9.54 mmol) was suspended in anhydrous tetrahydrofuran (30 ml) to which, while cooling in an ice bath, was subsequently added dropwise an anhydrous tetrahydrofuran (10 ml) solution of ethyl trans-1-benzyl-4-(1-tert-butoxycarbonylaminocyclopropyl)pyrrolidine-3-carboxylate (1.24 g, 3.18 mmol) over a period of 15 minutes. After 4 hours of stirring at the same temperature, ice-cooled water was gradually added to the reaction solution. The reaction suspension was subjected to celite filtration (chloroform washing) to separate the organic layer. The aqueous layer was extracted with chloroform (50 ml×2), and the organic layers were combined and dried over anhydrous sodium sulfate. By evaporating the solvent, 1.12 g (>99%) of the title compound was obtained.

$^1$H-NMR (400 MHz, CDCl$_3$) δ: 7.34–7.23 (5 H, m), 5.01 (1 H, brs), 3.61 (2 H, brs), 3.59 (2 H, s), 2.95–2.87 (1 H, m), 2.63–2.49 (2 H, m), 2.37–2.27 (1 H, m), 1.98–1.88 (1 H, m), 1.43 (9 H, s), 1.25 (2 H, t, J=7.33 Hz), 0.94–0.84 (1 H, m), 0.84–0.70 (2 H, m), 0.70–0.62 (1 H, m).

Example 1

5-Amino-7-[trans-4-(1-aminocycloproryl)-3-hydroxymethyl-1-pyrrolidinyl]-1-cyclopropyl-6-fluoro-1,4-dihydro-8-methyl-4-oxoquinoline-3-carboxylic acid

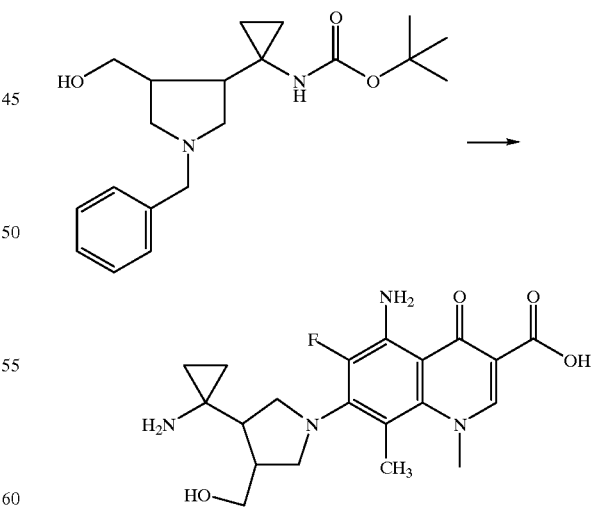

Trans-1-benzyl-4-(1-tert-butoxycarbonylaminocyclopropyl)-3-hydroxymethylpyrrolidine (1.10 g, 3.18 mmol) was dissolved in ethanol (50 ml), and the solution was mixed with palladium hydroxide (500 mg) and stirred for 1.5 hours at room temperature under a hydrogen atmosphere. The reaction suspension was subjected to celite filtration (ethanol washing) and the solvent was evaporated. The resulting residue and 5-amino-1-cyclopropyl-6,7-difluoro-1,4-dihydro-8-methyl-4-oxoquinoline-3-carboxylic acid (471 mg, 1.60 mmol) were dissolved in dimethyl sulfoxide (20 ml) and, under a nitrogen atmosphere, the solution was mixed with triethylamine (5 ml) and stirred at 150° C. for 19 hours. After evaporating the solvent, the resulting residue was mixed with 10% citric acid aqueous solution (50 ml) and extracted with chloroform (50 ml×2), and the extract was dried over anhydrous sodium sulfate. After evaporating the solvent, the resulting residue was mixed with concentrated hydrochloric acid (5 ml) and stirred for 1 hour. This was mixed with water (50 ml) and washed with chloroform (50 ml×2). The aqueous layer was adjusted to pH 12.00 with a sodium hydroxide aqueous solution and washed with chloroform (50 ml×2). Finally, the aqueous layer was adjusted to pH 7.40 with 1 N hydrochloric acid and extracted with chloroform (300 ml×5). The extract was dried over anhydrous sodium sulfate, the solvent was evaporated and then the resulting residue was recrystallized from ethanol to obtain 165 mg (38%) of the title compound.

Melting point: 179–182° C.

$^1$H-NMR (400 MHZ, CDCl$_3$) δ: 8.40 (1 H, s), 4.06–3.97 (1 H, m), 3.85–3.79 (1 H, m), 3.68–3.48 (4 H, m), 3.47–3.39 (1 H, m), 2.50–2.40 (1 H, m), 2.42 (3 H, s), 1.79–1.70 (1 H, m), 1.17–1.03 (2 H, m), 0.82–0.67 (2 H, m), 0.67–0.46 (4 H, m).

Elemental analysis data; for $C_{22}H_{27}FN_4O_4$ calcd.; C, 61.38; H, 6.32; N, 13.01 found; C, 61.15; H, 6.31; N, 12.78

Reference Example 2-1

Ethyl 3-(1-tert-butoxycarbonylaminocyclopropyl) propiolate

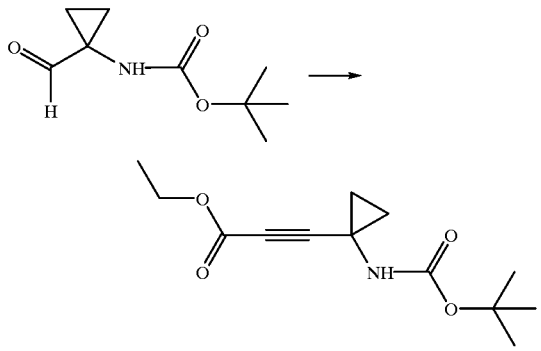

Under a nitrogen atmosphere, chloromethyltrimethylphosphonium chloride (5.156 g, 14.85 mmol) was suspended in anhydrous tetrahydrofuran (30 ml) to which, after cooling to −55° C., was subsequently added dropwise a 1.68 M n-butyl lithium n-hexane solution (8.87 ml, 14.90 mmol) over a period of 5 minutes. The reaction suspension was stirred for 30 minutes in an ice bath and for 3 hours at room temperature and then cooled to −55° C. To the reaction suspension was added dropwise an anhydrous tetrahydrofuran (10 ml) solution of 1-tert-butoxycarbonylaminocyclopropane carbaldehyde (2.498 g, 13.50 mmol) over a period of 10 minutes, subsequently stirring the mixture for 1 hour at −50° C. and then for 30 minutes in an ice bath. The reaction suspension was cooled to −78° C., an n-hexane solution of 1.68 M an n-butyl lithium (17.68 ml, 29.70 mmol) was added dropwise thereto over a period of 10 minutes and then the mixture was stirred at −78° C. for 20 minutes. Ethyl chloroformate (1.61 ml, 16.88 mmol) was added dropwise to the reaction suspension which was subsequently stirred for 1.5 hours at −78° C. and then for 1 hour in an ice bath. While cooling in an ice bath, the reaction suspension was mixed with saturated brine (30 ml), the organic layer was separated and the aqueous layer was extracted with diethyl ether (30 ml×2). The organic layers were combined, washed with saturated brine (30 ml) and dried over anhydrous magnesium sulfate. After filtration, the filtrate was concentrated under reduced pressure, and the resulting residue was applied to a flash silica gel chromatography column and eluted with an eluant of n-hexane:ethyl acetate=5:1, to-thereby obtain 2.178 g (63.9%) of the title compound as a colorless oil.

$^1$H-NMR (400 MHz, CDCl$_3$) δ: 5.04 (brs, 1 H), 4.27 (q, J=7.16 Hz, 2 H), 1.44 (s, 9 H), 1.28 (t, J=7.16 Hz, 3 H), 1.15 (m, 2 H), 1.06 (m, 2 H).

Reference Example 2-2

Ethyl 1-benzyl-4-(1-tert-butoxycarbonylaminocyclopropyl)-3-pyrroline-3-carboxylate

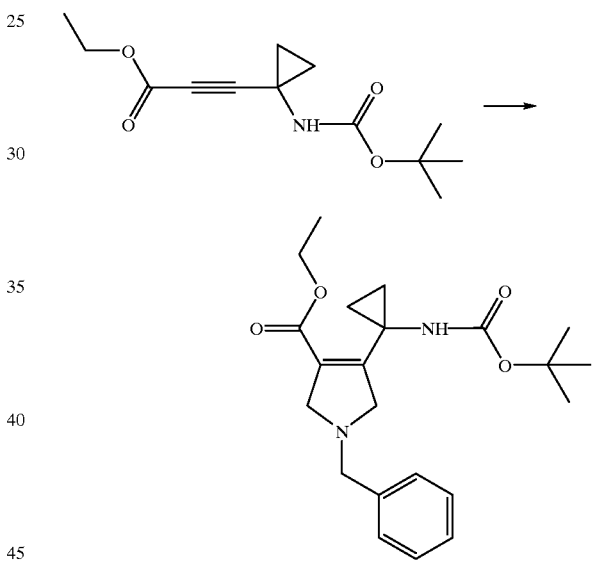

N-Benzyl-N-(n-butoxymethyl)trimethylsilylmethylamine (2.006 g, 7.176 mmol) and ethyl 3-(1-tert-butoxycarbonylaminocyclopropyl)propiolate (1.136 g, 4.485 mmol) were dissolved in dry dichloromethane (9 ml) and, while stirring at room temperature, the solution was mixed with dichloromethane solution of 1.0 M trifluoroacetic acid (0.72 ml, 0.72 mmol). After 3 hours of stirring, the reaction solution was mixed with a saturated sodium bicarbonate aqueous solution (20 ml) and extracted with dichloromethane (20 ml×3). The organic layers were combined, washed with saturated brine (30 ml) and then dried over anhydrous magnesium sulfate. After filtration, the filtrate was concentrated under reduced pressure, and the resulting residue was applied to a flash silica gel chromatography column and eluted with chloroform, to thereby obtain 1.449 g (83.6%) of the title compound as a colorless oil.

$^1$H-NMR (400 MHz, CDCl$_3$) δ: 7.40–7.11 (m, 5 H), 5.17 (brs, 1 H), 4.12 (q, J=6.83 Hz, 2 H), 3.85 (m, 2 H), 3.72 (m, 2 H), 3.67 (s, 2 H), 1.44 (s, 9 H), 1.24 (t, J=6.83 Hz, 3 H), 1.14 (m, 2 H), 1.01 (m, 2 H).

Reference Example 2-3

Ethyl cis-1-benzyl-4-(1-tert-butoxycarbonylaminocycloproryl)pyrrolidine-3-carboxylate

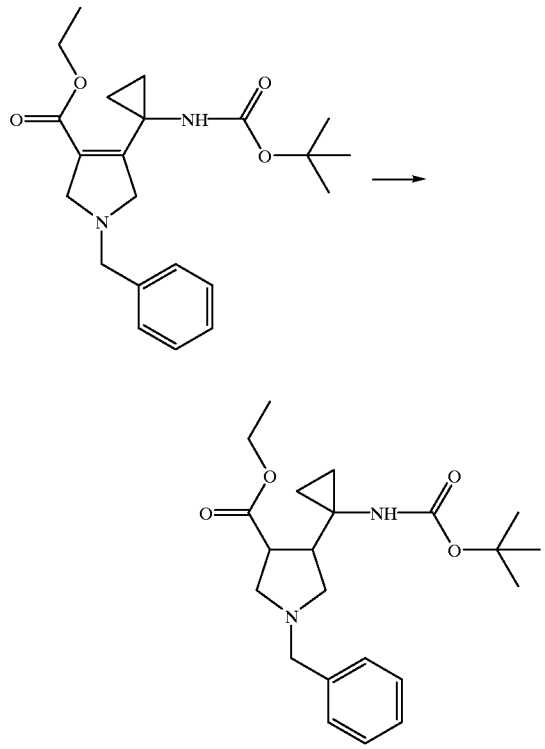

Under a stream of nitrogen, bis(bicyclo[2.2.1]hepta-2,5-diene)rhodium(I)perchlorate (54.5 mg, 0.14 mmol) and 1,2-bis(diphenylphpsphino)ethane (67.4 mg, 0.17 mmol) were dissolved in dried and degassed methanol (25 ml) and stirred at room temperature for 10 minutes. The thus prepared catalyst solution was mixed with dried and degassed methanol (15 ml) in which ethyl 1-benzyl-4-(1-tert-butoxycarbonylaminocyclopropyl)-3-pyrroline-3-carboxylate (1.090 g, 2.820 mmol) had been dissolved, and the reaction solution was stirred at room temperature for 2.5 hours under a hydrogen atmosphere (1 kg/cm²). The reaction solution was mixed with activated carbon (1 g), and the mixture was stirred at room temperature for 30 minutes and then filtered through celite (methanol washing). After concentrating the filtrate under reduced pressure, the resulting residue was applied to a flash silica gel chromatography column and eluted with an eluant of n-hexane:ethyl acetate=5:1, to thereby obtain 1.071 g (97.8%) of the title compound as colorless crystals.

$^1$H-NMR (400 MHz, CDCl$_3$) δ: 7.40–7.19 (m, 5 H), 5.07 (brs, 1 H), 4.13 (q, J=7.33 Hz, 2 H), 3.63 (s, 2 H), 2.87 (m, 1 H), 2.67 (m, 1 H), 2.54 (m, 1 H), 2.35 (m, 1 H), 2.15 (m, 1 H), 1.79 (m, 1 H), 1.46 (s, 9 H), 1.23 (t, J=7.33 Hz, 3 H), 0.85 (m, 2 H), 0.69 (m, 2 H).

Reference Example 2-4

Cis-1-benzyl-4-(1-tert-butoxycarbonylaminocycloproiyl)-3-hydroxymethylpyrrolidine

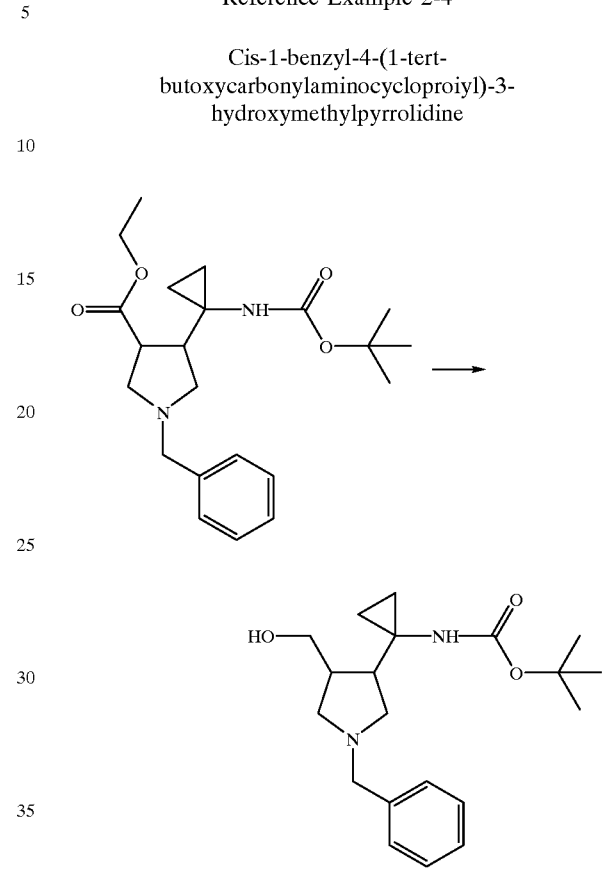

Under a nitrogen atmosphere, lithium aluminum hydride (195.6 mg, 5.153 mmol) was suspended in anhydrous tetrahydrofuran (40 ml) to which, while stirring at −15° C., was subsequently added dropwise an anhydrous tetrahydrofuran (10 ml) solution of ethyl cis-1-benzyl-4-(1-tert-butoxycarbonylaminocyclopropyl)pyrrolidine-3-carboxylate (1.001 g, 2.577 mmol) over a period of 15 minutes. The reaction suspension was stirred for 3.5 hours in an ice bath, gradually mixed with cold water (5 ml) and then stirred for an additional 15 minutes at room temperature. The reaction suspension was filtered through celite (diethyl ether washing), and the resulting filtrate was concentrated under reduced pressure and dried, to thereby obtain 833.9 mg (93.4%) of the title compound as a colorless oil.

$^1$H-NMR (400 MHz, CDCl$_3$) δ: 7.39–7.00 (m, 5 H), 5.10 (brs, 1 H), 3.69 (m, 2 H), 3.58 (s, 2 H), 2.99 (m, 1 H), 2.61 (m, 1 H), 2.51 (m, 1 H), 2.27 (m, 1 H), 2.00 (m, 1 H), 1.94 (brs, 1 H), 1.74 (m, 1 H), 1.42 (s, 9 H), 0.90 (m, 1 H), 0.74–0.61 (m, 3 H).

Reference Example 2-5

Cis-4-(1-tert-butoxycarbonylaminocyclopropyl)-3-hydroxymethylpyrrolidine

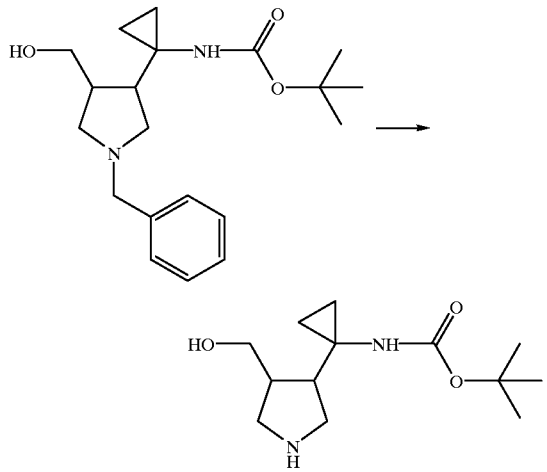

Cis-1-benzyl-4-(1-tert-butoxycarbonylaminocyclopropyl)-3-hydroxymethylpyrrolidine (820.1 mg, 2.376 mmol) was dissolved in methanol (50 ml), and the solution was mixed with a 5% palladium-carbon catalyst (water content, 55.6%; 750 mg) and stirred for one day under a hydrogen pressure of 4.5 kg/cm². After removing the catalyst by celite filtration (methanol washing), the resulting filtrate was concentrated under reduced pressure to obtain 578.8 mg (91%) of the title compound as a white amorphous substance.

¹H-NMR (400 MHz, CDCl₃) δ: 5.05 (brs, 1 H), 3.72 (m, 2 H), 3.15 (m, 2 H), 2.82 (m, 2 H), 2.29 (m, 1 H), 1.94 (br, 2 H), 1.76 (m, 1 H), 1.42 (s, 9 H), 0.92 (m, 2 H), 0.82 (m, 1 H), 0.61 (m, 1 H).

Example 2

5-Amino-7-[cis-4-(1-aminocyclopropyl)-3-hydroxymethyl-1-pyrrolidinyl]-1-cyclopropyl-6-fluoro-1,4-dihydro-8-methyl-4-oxoquinoline-3-carboxylic acid

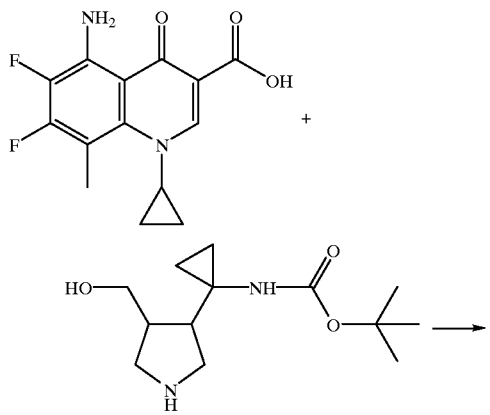

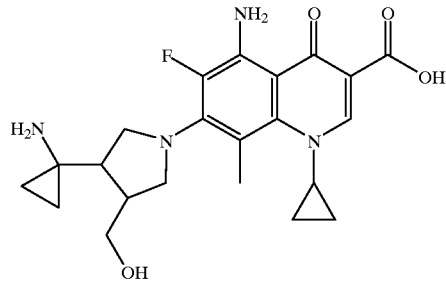

Cis-4-(1-tert-butoxycarbonylaminocyclopropyl)-3-hydroxymentylpyrrolidine (550.1 mg, 2.146 mmol) was dissolved in dimethyl sulfoxide (15 ml), and the solution was mixed with triethylamine (3.5 ml) and 5-amino-1-cyclopropyl-6,8-difluoro-1,4-dihydro-8-methyl-4-oxoquinoline-3-carboxylic acid (300.2 mg, 1.020 mmol) and stirred for 22 hours in an oil bath of 150° C. under a nitrogen atmosphere. After cooling, dimethyl sulfoxide was evaporated under reduced pressure, the resulting residue was dissolved in chloroform (100 ml) and washed with 10% citric acid aqueous solution (100 ml) and saturated brine (50 ml) in that order, and then the organic layer was dried over anhydrous magnesium sulfate. After filtration, the filtrate was concentrated under reduced pressure, concentrated hydrochloric acid (10 ml) was added dropwise to the resulting residue which was cooled in an ice bath, and then the mixture was stirred for 1 hour. The aqueous reaction solution was washed with dichloromethane (20 ml×4), and the aqueous layer was adjusted to pH 12 with 15% sodium hydroxide aqueous solution and washed with dichloromethane (20 ml×2). The aqueous solution was adjusted to pH 7.2 with 1 N hydrochloric acid and extracted with chloroform (100 ml×4). The organic layers were combined, dried over anhydrous magnesium sulfate and filtered, and the resulting filtrate was concentrated under reduced pressure. The thus obtained crude product was purified by recrystallizing from 2-propanol-diisopropyl ether, and the thus formed crystals were dried at 70° C. for 18 hours under reduced pressure to obtain 112.4 mg (25.6%) of the title compound as yellow crystals.

Melting point: 158.8–159.9° C. (decomposition)

¹H-NMR (400 MHz, 0.1 N NaOD) δ: 8.39 (s, 1 H), 3.99 (m, 1 H), 3.80 (dd, J=11.23, 5.37 Hz, 1 H), 3.62 (m, 2 H), 3.51 (d, J=7.32, 2 H), 3.41 (t, J=7.81 Hz, 1 H), 2.45 (m, 1 H), 2.37 (s, 3 H), 1.71 (q, J=7.81, 1 H), 1.18 (m, 2 H), 0.74 (m, 1 H), 0.70 (m, 1 H), 0.55 (m, 4 H).

Elemental analysis data; for C₂₂H₂₇FN₄O₄ calcd.; C, 61.38; H, 6.32; N, 13.02 found; C, 61.25; H, 6.32; N, 12.74

Reference Example 3-1

(3R,4S)-4-(1-Ethoxycarbonylcyclopropyl)-3-methyl-1-[(S)-1-phenylethyl]-2-pyrrolidone

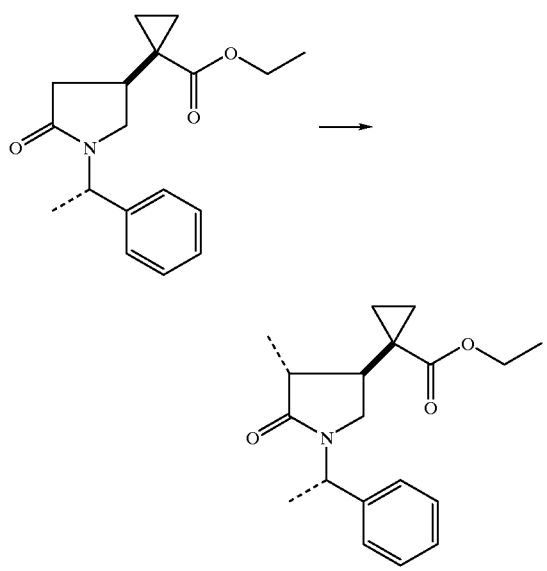

The following reaction was carried out under a nitrogen atmosphere. At −78° C., n-butyl lithium (5.39 ml, 1.68 N, n-hexane solution, 9.06 mmol) was added dropwise to a tetrahydrofuran solution (40 ml) of diisopropylethylamine (1.37 ml, 9.75 mmol), and the mixture was warmed to 0° C. and stirred for 30 minutes. At −78° C., to this was further added dropwise a tetrahydrofuran solution (20 ml) of (4S)-4-(1-ethoxycarbonylcyclopropyl)-1-[(S)-1-phenylethyl]-2-pyrrolidone (2.10 g, 6.97 mmol). After an additional 15 minutes of stirring, methyl iodide (2.17 ml, 34.8 mmol) was added dropwise thereto, and the mixture was stirred for 30 minutes while warming to 0° C. After completing the reaction, this was cooled in an ice bath and mixed with a saturated ammonium chloride aqueous solution (150 ml) and then tetrahydrofuran was evaporated. The resulting residue was extracted with chloroform (150 ml×3), and the organic layer was dried over anhydrous sodium sulfate. After evaporating the solvent, the resulting residue was purified by a silica gel column chromatography (silica gel, 160 ml; ethyl acetate:hexane=2:3), to thereby obtain 1.90 g (87%) of the title compound.

$^1$H-NMR (400 MHz, CDCl$_3$) δ: 0.67–0.75 (2 H, m), 1.06 (3 H, t, J=7.33 Hz), 1.14–1.19 (2 H, m), 1.24 (3 H, d, J=7.33 Hz), 1.52 (3 H, d, J=7.33 Hz), 1.98 (1 H, q, J=9.03 Hz), 2.40 (1 H, dq, J=9.03, 7.33 Hz), 2.84 (1 H, t, J=9.03 Hz), 3.39 (1 H, t, J=9.03 Hz), 3.95–4.06 (2 H, m), 5.53 (1 H, q, J=7.33 Hz), 7.28–7.35 (5 H, m).

Reference Example 3-2

(3R,4S)-4-(1-Ethoxycarbonylcyclopropyl)-3-methyl-1-[(S)-1-phenylethyl]-2-pyrrolidinethione

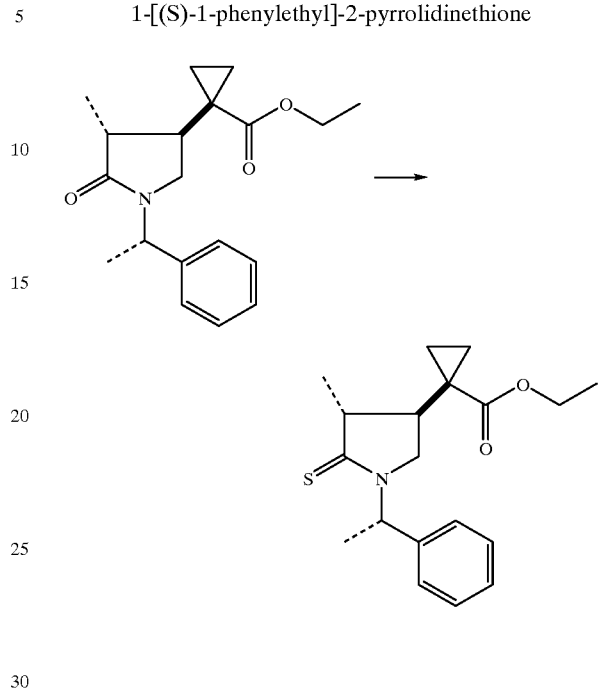

(3R,4S)-4-(1-Ethoxycarbonylcyclopropyl)-3-methyl-1-[(S)-1-phenylethyl]-2-pyrrolidone (1.85 g, 5.87 mmol) was dissolved in benzene (100 ml), and the solution was mixed with Lawesson's reagent (1.31 g, 3.24 mmol) and heated under reflux for 20 minutes. After completing the reaction, the solvent was evaporated and the resulting residue was purified by silica gel column chromatography (silica gel, 160 ml; ethyl acetate:hexane=1:4), to thereby obtain 1.80 g (92%) of the title compound.

$^1$H-NMR (400 MHz, CDCl$_3$) δ: 0.63–0.69 (2 H, m), 1.11 (3 H, t, J=7.08 Hz), 1.15–1.18 (2 H, m), 1.41 (3 H, d, J=7.32 Hz), 1.58 (3 H, d, J=6.84 Hz), 2.02–2.08 (1 H, m), 2.73–2.80 (1 H, m), 3.11 (1 H, dd, J=7.81, 11.23 Hz), 3.65 (1 H, dd, J=8.79, 11.23 Hz), 3.95–4.06 (2 H, m), 6.44 (1 H, q, J=6.84 Hz), 7.28–7.39 (5 H, m).

Reference Example 3-3

(3S,4R)-3-(1-Ethoxycarbonylcyclopropyl)-4-methyl-1-[(S)-1-phenylethyl]pyrrolidine

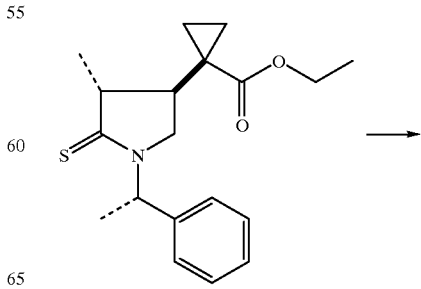

-continued

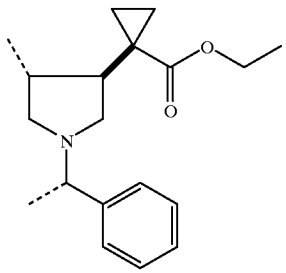

(3S,4R)-3-(1-Ethoxycarbonylcyclopropyl)-4-methyl-1-[(S)-1-phenylethyl]-2-pyrrolidinethion (1.80 g, 5.43 mmol) was dissolved in ethanol (100 ml), and the solution was mixed with Raney nickel (10 ml) and heated under reflux for 1.5 hours. After completing the reaction, the reaction solution was filtered through celite and the filtrate was concentrated under reduced pressure. The resulting residue was dissolved in chloroform (100 ml), washed with 10% ammonia water (100 ml), water (100 ml) and saturated brine (100 ml) in that order and then dried over anhydrous sodium sulfate. After evaporating the solvent, the resulting residue was purified by silica gel column chromatography (silica gel, 160 ml; ethyl acetate:hexane=1:1), to thereby obtain 558 mg (34%) of the title compound.

$^1$H-NMR (400 MHz, CDCl$_3$) δ: 0.75–0.83 (2 H, m), 1.02 (3 H, d, J=6.84 Hz), 1.11–1.14 (2 H, m), 1.21 (3 H, t, J=7.08 Hz), 1.30 (3 H, d, J=6.59 Hz), 1.70–1.78 (1 H, m), 2.04–2.15 (1 H, m), 2.19 (1 H, dd, J=6.35, 9.03 Hz), 2.42 (1 H, dd, J=9.03, 6.83 Hz), 2.58 (1 H, t, J=8.55 Hz), 2.67 (1 H, t, J=8.55 Hz), 3.13 (1 H, q, J=6.59 Hz), 4.05–4.11 (2 H, m), 7.21–7.33 (5 H, m).

Reference Example 3-4

(3S,4R)-1-Benxyloxycarbonyl-3-(1-ethoxycarbonylcyclopropl)-4-methylpyrrolidine

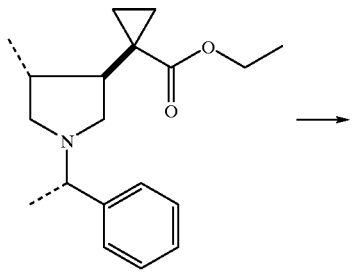

(3S,4R)-3-(1-Ethoxycarbonylcyclopropyl)-4-methyl-1-[(S)-1-phenylethyl]-2-pyrrolidine (1.24 g, 4.13 mmol) was dissolved in dichloromethane (40 ml) to which was subsequently added dropwise benzyl chloroformate (0.766 ml, 5.37 mmol). After completing the dropwise addition, the reaction solution was heated under reflux for 1.5 hours. After completing the reaction, the solvent was evaporated and the resulting residue was purified by silica gel column chromatography (silica gel, 100 ml; ethyl acetate:hexane=1:4), to thereby obtain 1.17 g (88%) of the title compound.

$^1$H-NMR (400 MHz, CDCl$_3$) δ: 0.69–0.77 (2 H, m), 1.04 (3 H, dd, J=6.83, 7.81 Hz), 1.20–1.26 (5 H, m), 1.75–1.87 (1 H, m), 2.27–2.37 (1 H, m), 2.91 (1 H, dt, J=2.93, 10.25 Hz), 3.32 (1 H, dd, J=10.74, 21.49 Hz), 3.59–3.75 (2 H, m), 4.07–4.13 (2 H, m), 5.12 (2 H, s), 7.21–7.33 (5 H, m).

Reference Example 3-5

1-[(3S,4R)-1-Benzyloxycarbonyl-4-methyl-3-Pyrrolidinyl]cyclopropanecarboxylic acid

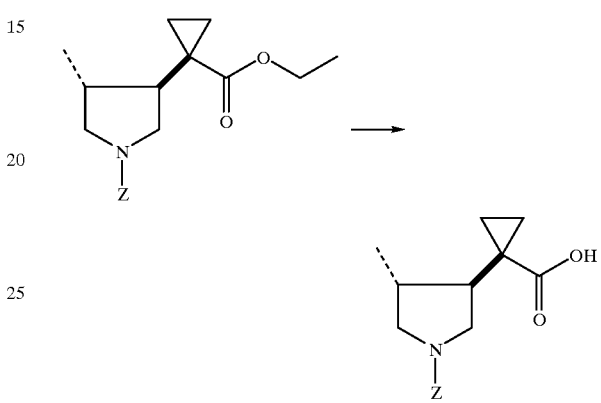

(3S,4R)-1-Benzyloxycarbonyl-3-(1-ethoxycarbonylcyclopropyl)-4-methylpyrrolidine (1.17 g, 3.66 mmol) was dissolved in ethanol (100 ml), and the solution was mixed with a 1 N sodium hydroxide aqueous solution (11 ml) and heated under reflux for 8 hours. After completing the reaction, the solvent was evaporated and the resulting residue was mixed with a 0.5 N hydrochloric acid aqueous solution (30 ml). This was extracted with ethyl acetate (50 ml×3), and the organic layer was washed with water (50 ml) and saturated sodium chloride aqueous solution (50 ml) in that order. This was dried over anhydrous sodium sulfate and then the solvent was evaporated to obtain 1.20 g of the title compound quantitatively.

$^1$H-NMR (400 MHz, CDCl$_3$) δ: 0.77–0.85 (2 H, m), 1.05 (3 H, t, J=6.84 Hz), 1.25–1.35 (2 H, m), 1.69 (1 H, q, J=9.57 Hz), 2.34–2.46 (1 H, m), 2.90 (1 H, dd, J=6.35, 9.57 Hz), 3.39 (1 H, t, J=10.26 Hz), 3.59–3.75 (2 H, m), 5.12 (2 H, s), 7.30–7.38 (5 H, m).

Reference Example 3-6

(3R, 4R)-1-Benzyloxycarbonyl-3-(1-tert-butoxycarbonylaminocyclopropyl)-4-methylpyrrolidine

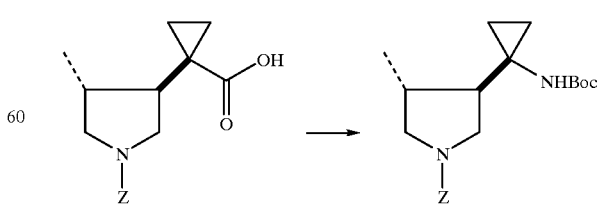

1-[(3S,4R)-1-Benzyloxycarbonyl-4-methyl-3-pyrrolidinyl]cyclopropanecarboxylic acid (1.20 g, 3.66 mmol) was dissolved in tert-butyl alcohol (50 ml), and the solution was mixed with diphenylphosphoryl azide (0.946 ml, 4.39 mmol) and triethylamine (1.02 ml, 7.32 mmol) and heated under reflux for 19 hours. After completing the reaction, the solvent was evaporated and the resulting residue was purified by silica gel column chromatography (silica gel, 120 ml; ethyl acetate:hexane=1:2), to thereby obtain 0.793 g (58%) of the title compound.

$^1$H-NMR (400 MHz, CDCl$_3$) δ: 0.52–0.60 (1 H, m), 0.70–0.82 (2 H, m), 0.90–1.01 (1 H, m), 1.15 (3 H, d, J=5.37 Hz), 1.41 (9 H, s), 1.43–1.50 (1 H, m), 2.08–2.17 (1 H, m), 2.91 (1 H, dt, J=5.86, 10.26 Hz), 3.28 (1 H, t, J=10.26 Hz), 3.57–3.73 (2 H, m), 4.80 (1 H, d, J=7.82 Hz), 5.12 (2 H, s), 7.29–7.37 (5 H, m).

Example 3

5-Amino-7-[(3R,4R)-3-(1-aminocyclopropyl)-4-methyl-1-pyrrolidinyl]-6-fluoro-1-[(1R,2S)-2-fluorocyclopropyl]-1,4-dihydro-8-methyl-4-oxoquinoline-3-carboxylic acid

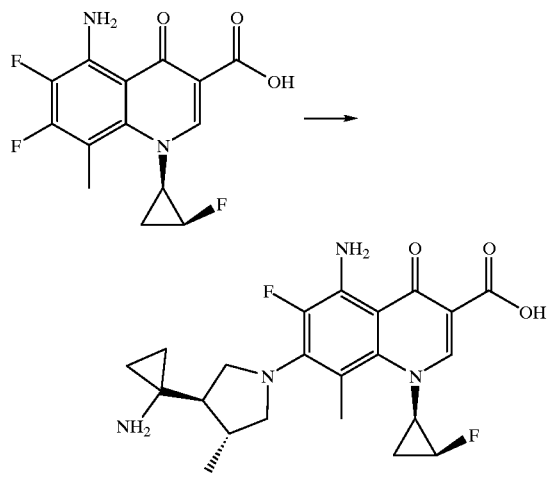

(3R,4R)-1-Benzyloxycarbonyl-3-(1-tert-butoxycarbonylaminocyclopropyl)-4-methylpyrrolidine (793 mg, 2.12 mmol) was dissolved in ethanol (50 ml), and the solution was mixed with 5% palladium-carbon (790 mg) to carry out hydrogenation under a pressure of 5 atmospheres. After completing the reaction, the 5% palladium carbon was removed by filtration and ethanol was evaporated. The thus obtained residue was dissolved in dimethyl sulfoxide (8 ml), and the solution was mixed with triethylamine (2 ml) and 5-amino-6,7-difluoro-1-[(1R,2S)-2-fluorocyclopropyl]-1,4-dihydro-8-methyl-4-oxoquinoline-3-carboxylic acid (330 mg, 1.06 mmol) and stirred at 150° C. for 18 hours. After completing the reaction, dimethyl sulfoxide was evaporated, and the thus obtained residue was mixed with chloroform (100 ml) and washed with 10% citric acid (100 ml) and saturated brine (100 ml) in that order. The organic layer was dried over anhydrous sodium sulfate and then the solvent was evaporated. To the thus obtained residue, which was cooled in an ice bath, was added dropwise concentrated hydrochloric acid (10 ml), followed by 1 hour of stirring at room temperature. After completing the reaction, the reaction solution was washed with dichloromethane (20 ml). The aqueous layer was adjusted to pH 12 with a sodium hydroxide aqueous solution and then to pH 7.4 with hydrochloric acid, subsequently carrying out extraction with chloroform (100 ml×4). The organic layers were combined and dried over anhydrous sodium sulfate and then the solvent was evaporated. The thus obtained residue was subjected to silica gel thin layer chromatography and developed with the bottom layer of a mixture solvent of chloroform:methanol=3:1, and then the resulting silica gel was scratched off and extracted with the same solvent system. The solvent was evaporated and the thus obtained residue was dissolved in a 1 N hydrochloric acid aqueous solution (6 ml) and stirred at room temperature for 10 minutes. After evaporating the solvent, the resulting crude product was recrystallized from isopropyl alcohol to obtain 20.1 mg (4%) of the title compound.

Melting point: 203–205° C. (decomposition)

$[α]_D^{24}$=−162.93 (c=0.205, 0.1 N sodium hydroxide aqueous solution)

$^1$H-NMR (400 MHz, 0.1 N NaOD) δ: 0.35–0.41 (1 H, m), 0.48–0.60 (3 H, m), 1.10–1.15 (1 H, m), 1.12 (3 H, d, J=6.35 Hz), 1.40–1.55 (2 H, m), 2.26 (3 H, s), 2.18–2.24 (1 H, m), 3.30 (1 H, t, J=8.55 Hz), 3.29–3.51 (2 H, m), 3.76–3.78 (1 H, m), 3.89–3.94 (1 H, m), 4.96 (1 H, dm, J=65.91 Hz), 8.25 (1 H, d, J=2.93 Hz).

Elemental analysis data; for $C_{22}H_{26}F_2N_4O_3 \cdot HCl \cdot 1.25H_2O$: calcd.; C, 53.77; H, 6.05; N, 11.40 found; C, 53.68; H, 6.05; N, 11.12

Reference Example 4-1

4-(S)-(1-Ethoxycarbonylcyclopropyl)-3-(R)-hydroxy-1-[1-(S)-phenylethyl]-2-pyrrolidone

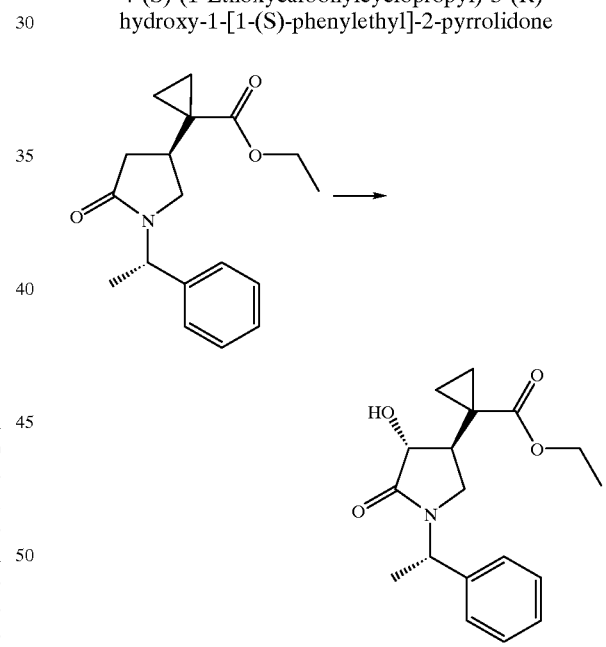

Under a nitrogen atmosphere, diisopropylamine (3.93 ml, 28.0 mmol) was dissolved in anhydrous tetrahydrofuran (200 ml) to which, after cooling to −78° C., was subsequently added dropwise an n-hexane solution of 1.69 M n-butyl lithium (15.9 ml, 26.9 mmol) over a period of 10 minutes. After 20 minutes of stirring at 0° C. and subsequent cooling to −78° C., to the resulting reaction solution was added dropwise anhydrous tetrahydrofuran solution (40 ml) of 4-(S)-(1-ethoxycarbonylcyclopropyl)-1-[1-(S)-phenylethyl]-2-pyrrolidone (6.74 g, 22.4 mmol) over a period of 15 minutes. The reaction solution was stirred at −78° C. for 10 minutes and then the reaction vessel was charged with dried oxygen at the same temperature. The reaction solution was stirred at −78° C. for 20 minutes and then mixed-with a saturated ammonium chloride aqueous solution (200 ml). This was warmed up to room temperature and the organic layer was separated. The aqueous layer was extracted with diethyl ether (200 ml×2), and the organic layers were combined and dried over anhydrous magnesium sulfate. After filtration, the filtrate was concentrated under reduced pressure, and the resulting residue was subjected to flash silica gel chromatography and eluted with an eluant of n-hexane:ethyl acetate=2:1, to thereby obtain 5.21 g (73%) of the title compound as a colorless oil.

$^1$H-NMR (400 MHz, CDCl$_3$) δ: 0.86–0.96 (2 H, m), 1.13 (3 H, t, J=7.08 Hz), 1.18–1.30 (2 H, m), 1.56 (3 H, d, J=6.92 Hz), 2.38 (1 H, dd, J=18.06, 9.28 Hz), 2.81 (1 H, t, J=9.28 Hz), 3.50 (2 H, t, J=9.28 Hz), 3.99–4.07 (2 H, m), 4.11 (1 H, d, J=9.28 Hz), 5.48 (1 H, q, J=6.92 Hz), 7.26–7.36 (5 H, m).

Reference Example 4-2

3-(R)-Tert-butyldimethylsilyloxy-4-(S)-(1-ethoxycarbonylcyclopropyl)-1-[1-(S)-1-phenylethyl]-2-pyrrolidone

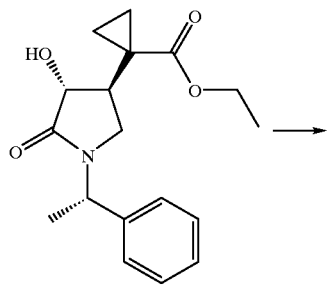

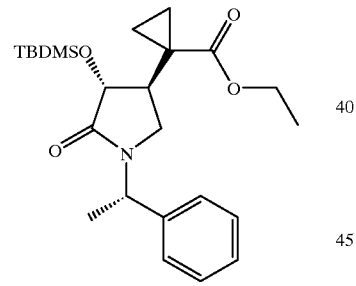

4-(S)-(1-Ethoxycarbonylcyclopropyl)-3-(R)-hydroxy-1-[1-(S)-phenylethyl]-2-pyrrolidone (7.26 g, 22.87 mmol) was dissolved in anhydrous dimethylformamide (75 ml), and the solution was mixed with imidazole (3.90 g, 57.3 mmol) and stirred at room temperature for 10 minutes. This was mixed with tert-butylchlorodimethylsilane (4.32 g, 28.7 mmol) and stirred for 4 hours. After concentrating the mixture under reduced pressure, the thus obtained residue was dissolved in ethyl acetate (300 ml), washed with water (150 ml), saturated sodium bicarbonate aqueous solution (150×5) and saturated brine (150 ml) in that order and then dried over anhydrous sodium sulfate. After filtration, the filtrate was concentrated under reduced pressure and the resulting residue was subjected to flash silica gel chromatography and eluted with an eluant of n-hexane:ethyl acetate=6:1, to thereby obtain 8.74 g (88%) of the title compound as a colorless oil.

$^1$H-NMR (400 MHz, CDCl$_3$) δ: 0.043 (3 H, s), 0.122 (3 H, s), 0.54–0.63 (1 H, m), 0.79 (9 H, s), 0.95 (3 H, t, J=7.08 Hz), 1.03–1.15 (3 H, m), 1.38 (3 H, d, J=6.98 Hz), 1.61–1.90 (1 H, m), 2.83 (1 H, t, J=9.28 Hz), 3.13 (1 H, t, J=9.28 Hz), 3.81–3.90 (2 H, m), 4.48 (1 H, d, J=9.28 Hz), 5.36 (1 H, q, J=6.96 Hz), 7.14–7.19 (5 H, m).

Reference Example 4-3

3-(R)-Tert-butyldimethylsilyloxy-4-(S)-(1-ethoxycarbonylcyclopropyl)-1-[1-(S)-phenylethyl]-2-pyrrolidinethione

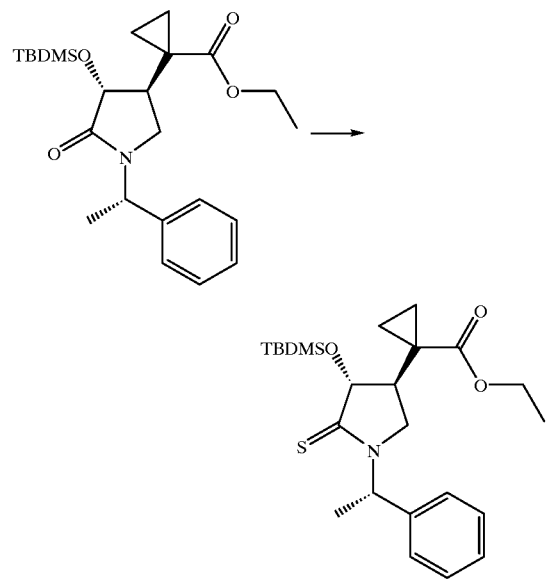

3-(R)-Tert-butyldimethylsilyloxy-4-(S)-(1-ethoxycarbonylcyclopropyl)-1-[1-(S)-phenylethyl]-2-pyrrolidone was dissolved in dry benzene (200 ml), and the solution was mixed with Lawesson's reagent (4.49 g, 11.1 mmol) and heated under reflux for 3 hours. After cooling, benzene was evaporated under reduced pressure, and the resulting residue was subjected to flash silica gel chromatography and eluted with an eluant of n-hexane:ethyl acetate=4:1, to thereby obtain 7.96 g (88%) of the title compound as a light yellow oil.

$^1$H-NMR (400 MHz, CDCl$_3$) δ: 0.176 (3 H, s), 0.327 (3 H, s), 0.63–0.68 (1 H, m), 0.92–0.95 (1 H, m), 0.95 (9 H, s), 1.11 (3 H, t, J=7.08 Hz), 1.15–1.20 (1 H, m), 1.29–1.34 (1 H, m), 1.58 (3 H, d, J=6.84 Hz), 1.68–1.79 (1 H, m), 3.27 (1 H, t, J=10.74 Hz), 3.44 (1 H, dd, J=10.74, 8.79 Hz), 3.99–4.01 (2 H, m), 4.93 (1 H, d, J=8.30 Hz), 6.38 (1 H, q, J=6.84 Hz), 7.44–7.46 (5 H, m).

Reference Example 4-4

3-(S)-Tert-butyldimethylsilyloxy-4-(R)-(1-ethoxycarbonylcyclopropyl)-1-[1-(S)-phenylethyl]pyrrolidine

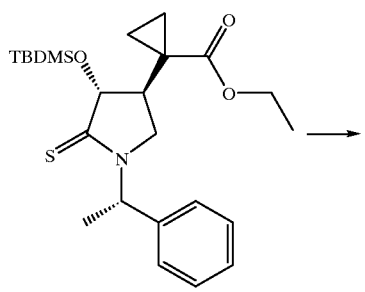

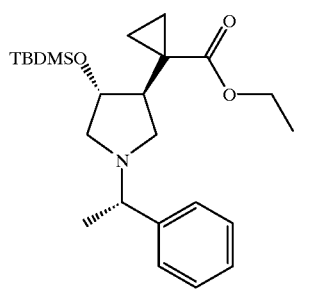

3-(R)-Tert-butyldimethylsilyloxy-4-(S)-(1-ethoxycarbonylcyclopropyl)-1-[1-(S)-phenylethyl]-2-pyrrolidinethione (7.96 g, 17.–74 mmol) was dissolved in anhydrous ethanol (490 ml), and the solution was mixed with Raney nickel (25 ml) and heated under reflux for 40 minutes. After removing the catalyst by celite filtration (ethanol washing), the resulting filtrate was concentrated under reduced pressure. The thus obtained residue was dissolved in chloroform (400 ml), washed with 10% ammonia water (300 ml), water (300 ml) and saturated brine (300 ml) in that order and then dried over anhydrous sodium sulfate. After filtration, the filtrate was concentrated under reduced pressure and the resulting residue was subjected to flash silica gel chromatography and eluted with an eluant of n-hexane:ethyl acetate=6:1, to thereby obtain 5.48 g (74%) of the title compound as a colorless oil.

$^1$H-NMR (400 MHz, CDCl$_3$) δ: 0.023 (3 H, s), 0.038 (3 H, s), 0.61–0.64 (1 H, m), 0.83–0.85 (1 H, m), 0.84 (9 H, s), 1.11–1.13 (2 H, m), 1.17 (3 H, t, J=7.33 Hz), 1.29 (3 H, d, J=6.83 Hz), 1.74–1.79 (1 H, m), 2.35 (1 H, t, J=9.27 Hz), 2.62–2.67 (1 H, m), 2.74–2.77 (1 H, m), 3.16 (1 H, q, J=6.51 Hz), 4.00–4.06 (2 H, m), 4.33–4.37 (1 H, m), 7.23–7.30 (5 H, m).

Reference Example 4-5

1-Benzyloxycarbonyl-3-(S)-tert-butyldimethylsilyloxy-4-(R)-(1-ethoxycarbonylcyclopropyl)pyrrolidine

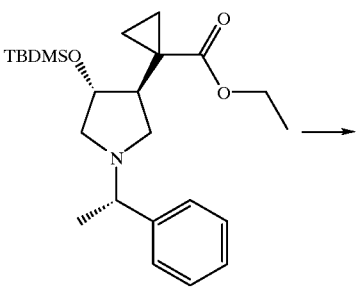

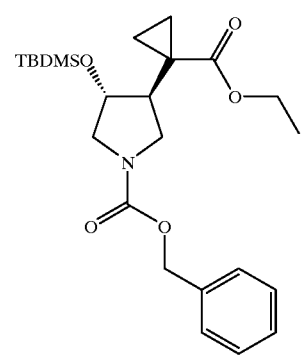

3-(S)-Tert-butyldimethylsilyloxy-4-(R)-(1-ethoxycarbonylcyclopropyl)-1-[1-(S)-phenylethyl]pyrrolidine (5.48 g, 13.15 mmol) was dissolved in dry dichloromethane (120 ml), and benzyl chloroformate (3.76 ml, 26.3 mmol) was added dropwise to the thus prepared solution which was cooled in an ice bath. After heating the reaction solution under reflux for 2 hours, dichloromethane was evaporated under reduced pressure. Thereafter, the resulting residue was subjected to flash silica gel chromatography and eluted with an eluant of n-hexane:ethyl acetate=5:1, to thereby obtain 4.52 g (77%) of the title compound as a colorless oil.

$^1$H-NMR (400 MHz, CDCl$_3$) δ: 0.049 (6 H, s), 0.66–0.71 (1 H, m), 0.87 (9 H, s), 0.93–0.97 (1 H, m), 1.04–1.08 (1 H, m), 1.22 (3 H, t, J=3.42 Hz), 1.36–1.39 (1 H, m), 1.77–1.87 (1 H, m), 3.08 (1 H, t, J=8.29 Hz), 3.43 (1 H, q, J=10.42 Hz), 3.60–3.82 (2 H, m), 4.08–4.16 (2 H, m), 4.54–4.63 (1 H, m), 5.10–5.18 (2 H, m), 7.29–7.35 (5 H, m).

Reference Example 4-6

1-Benzyloxycarbonyl-3-(S)-hydroxy-4-(R)-(1-ethoxycarbonylcyclopropyl)pyrrolidine

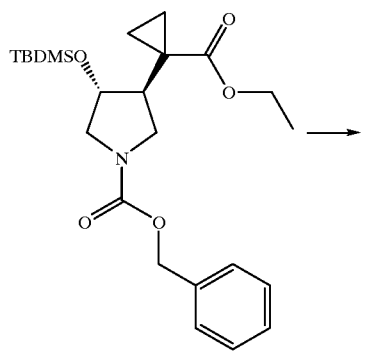

1-Benzyloxycarbonyl-3-(S)-tert-butyldimethylsilyloxy-4-(R)-(1-ethoxycarbonylcyclopropyl)pyrrolidine (1.79 g, 4.00 mmol) was dissolved in tetrahydrofuran (40 ml) to which, cooled in an ice bath, was subsequently added dropwise a tetrahydrofuran solution of 1.0 M tetrabutylammonium fluoride (5.33 ml, 5.33 mmol). The reaction solution was stirred at room temperature for 30 minutes and then tetrahydrofuran was evaporated under reduced pressure. Thereafter, the resulting residue was subjected to flash silica gel chromatography and eluted with an eluant of n-hexane:ethyl acetate=1:1, to thereby obtain 1.04 g (76%) of the title compound as a colorless oil.

$^1$H-NMR (400 MHz, CDCl$_3$) δ: 0.80–0.89 (2 H, m), 1.21–1.28 (5 H, m), 2.57–2.73 (1 H, m), 2.85–2.98 (1 H, m), 3.23–3.33 (2 H, m), 3.62–3.67 (1 H, m), 3.82–3.99 (1 H, m), 4.10–4.25 (3 H, m), 5.12 (2 H, s), 7.28–7.39 (5 H, m).

Reference Example 4-7

1-[1-Benzyloxycarbonyl-4-(R)-methoxy-3-(S)-pyrrolidinyl]cyclopropanecarboxylic acid

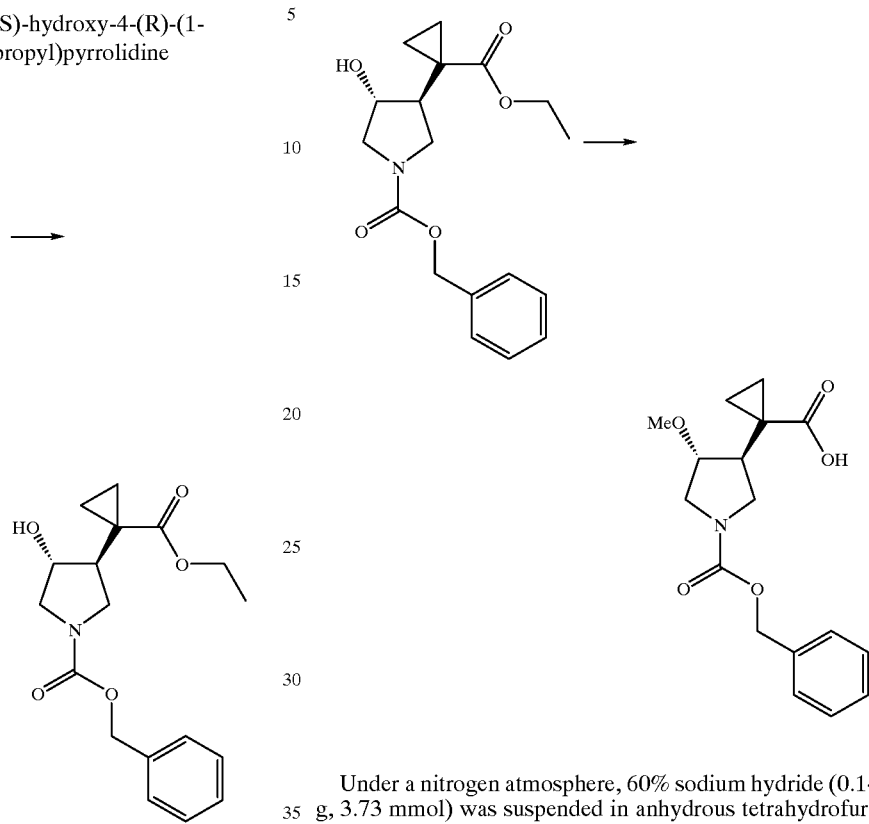

Under a nitrogen atmosphere, 60% sodium hydride (0.149 g, 3.73 mmol) was suspended in anhydrous tetrahydrofuran (20 ml) to which, after cooling to 0° C., was subsequently added dropwise a dry tetrahydrofuran (20 ml) solution of 1-benzyloxycarbonyl-3-(S)-hydroxy-4-(R)-(1-ethoxycarbonylcyclopropyl)pyrrolidine (0.98 g, 2.92 mmol) over a period of 5 minutes. After 15 minutes of stirring in an ice bath, dimethyl sulfate (0.441 ml, 4.66 mmol) was added dropwise to the reaction solution which was cooled in the ice bath. The reaction solution was stirred at room temperature for 4 hours and then mixed with water (0.5 ml), followed by evaporating tetrahydrofuran under reduced pressure. The thus obtained residue was dissolved in ethanol (40 ml), and a 1 M sodium hydroxide aqueous solution (8.76 ml) was added dropwise to the resulting solution at room temperature. The reaction solution was heated under reflux for 2 hours and then ethanol was evaporated under reduced pressure. The resulting residue was cooled in an ice bath, acidified by adding dropwise a 1 M hydrochloric acid aqueous solution (15 ml) and then extracted with ethyl acetate (50 ml×3). All of the organic layers were combined, washed with a 1 N hydrochloric acid aqueous solution (50 ml) and saturated brine (50 ml) and then dried over anhydrous sodium sulfate. After filtration, the filtrate was concentrated under reduced pressure to obtain 0.935 g (quantitative) of the title compound as a colorless amorphous substance.

¹H-NMR (400 MHz, CDCl₃) δ: 0.84–0.89 (1 H, m), 0.89–1.01 (1 H, m), 1.25–1.35 (2 H, m), 2.33–2.40 (1 H, m), 3.22–3.30 (2 H, m), 3.35 (3 H, s), 3.74–3.91 (3 H, m), 5.12 (2 H, s), 7.32–7.38 (5 H, m).

Reference Example 4-8

1-Benzyloxycarbonyl-4-(R)-(1-tert-butoxycarbonylaminocyclopropyl)-3-(R)-methoxypyrrolidine

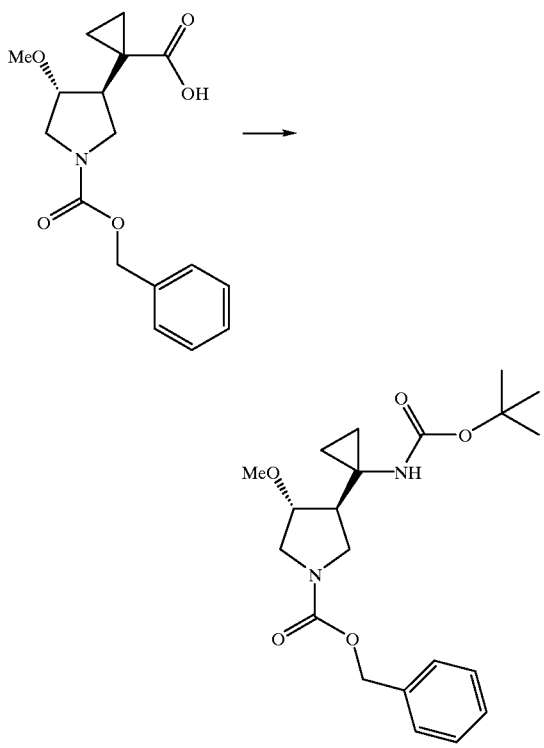

1-[1-Benzyloxycarbonyl-4-(R)-methoxy-3-(S)-pyrrolidinyl]cyclopropanecarboxylic acid (713 mg, 2.22 mmol) was dissolved in tert-butyl alcohol (20 ml), and the solution was mixed with diphenylphosphoryl azide (623 μl, 2.89 mmol) and triethylamine (775 μl, 5.56 mmol), stirred at room temperature for 20 minutes and then heated under reflux for 19 hours. The reaction solution was cooled and then concentrated under reduced pressure, and the resulting residue was subjected to flash silica gel chromatography and eluted with an eluant of n-hexane:ethyl acetate=3:2, to thereby obtain the title compound (431 mg, 50%) as a colorless oil.

¹H-NMR (400 MHz, CDCl₃) δ: 0.65–0.97 (4 H, m), 1.39, 1.41 (total 9 H, each s), 2.03–2.07 (1 H, m), 3.32, 3.34 (total 3 H, each s), 3.28–3.46 (2 H, m), 3.95–4.06 (1 H, m), 5.13 (2 H, s), 7.29–7.38 (5 H, m).

Example 4

5-Amino-7-[4-(R)-(1-aminocyclopropyl)-3-(R)-methoxy-1-pyrrolidinyl]-6-fluoro-1-[2-(S)-fluoro-1-(R)-cyclopropyl]-1,4-dihydro-8-methyl-4-oxoquinoline-3-carboxylic acid

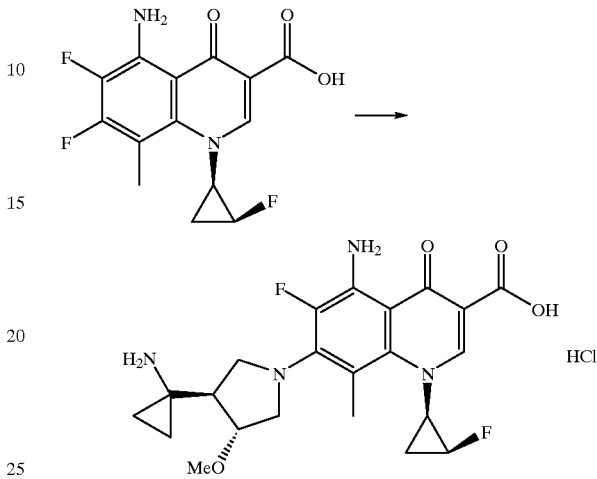

1-Benzyloxycarbonyl-4-(R)-(1-tert-butoxycarbonylaminocyclopropyl)-3-(R)-methoxypyrrolidine (550 mg, 1.41 mmol) was dissolved in ethanol (40 ml), and the solution was mixed with a 5% palladium-carbon catalyst (water content, 55.6%; 550 mg) and stirred for 4 hours under a pressured hydrogen atmosphere (4.5 kg/cm²). The catalyst was removed by celite filtration (methanol washing), and the filtrate was concentrated under reduced pressure. The thus obtained residue was dissolved in dimethyl sulfoxide (5 ml), and the solution was mixed with 5-amino-6,7-difluoro-1-[2-(S)-fluoro-1-(R)-cyclopropyl]-1,4-dihydro-8-methyl-4-oxoquinoline-3-carboxylic acid (249.8 mg, 0.80 mmol) and triethylamine (3 ml) and stirred for 2 days in an oil bath of 120° C. under a nitrogen atmosphere. After cooling, dimethyl sulfoxide was evaporated under reduced pressure, the thus obtained residue was dissolved in chloroform (100 ml) and washed with a 10% citric acid aqueous solution (50 ml×2) and saturated brine (100 ml) in that order and then the organic layer was dried over anhydrous magnesium sulfate. After filtration, the filtrate was concentrated under reduced pressure. To the thus obtained residue, which was cooled in an ice bath, was added dropwise concentrated hydrochloric acid (10 ml), followed by 1 hour of stirring at room temperature. After adding water (20 ml) to the reaction solution, the aqueous solution was washed with dichloromethane (50 ml×3), adjusted to pH 11 with sodium hydroxide aqueous solution and then washed with dichloromethane (50 ml×2). This was adjusted to pH 7.4 with concentrated hydrochloric acid and extracted with chloroform (150 ml×3). The organic layers were combined, dried over anhydrous sodium sulfate and then filtered, and the filtrate was concentrated under reduced pressure. The thus obtained residue was subjected to preparative silica gel thin layer chromatography (development with the bottom layer of a mixture of chloroform:methanol:water=7:3:1), and the resulting crude product was purified by recrystallizing from ethanol-diisopropyl ether and then dried under a reduced pressure to obtain 57 mg (16%) of the title compound as a yellow powder.

Melting point: 202.4–204.3° C.

$[\alpha]_D^{24} = -154.03°$ (c=0.335, 0.1 N NaOH)

IR (KBr disk): 3464, 3344, 2892, 2832, 1722, 1628, 1584, 1504, 1428, 1342, 1292, 1228 cm$^{-1}$ $^1$H-NMR (400 MHz, 0.1 N NaOD) δ: 0.60–0.65 (4 H, m), 1.14–1.24 (1 H, m), 1.49–1.59 (1 H, m), 2.07–2.13 (1 H, m), 2.37 (3 H, s), 3.41–3.66 (4 H, m), 3.44 (3 H, s), 3.96–4.09 (2 H, m), 4.95 (1 H, dm, J=64.94 Hz), 8.31 (1 H, d, J=2.44 Hz).

Elemental analysis data; for $C_{22}H_{26}F_2N_4O_4 \cdot 0.75H_2O$: calcd.; C, 57.20; H, 6.00; N, 12.13 found; C, 57.43; H, 5.80; N, 11.90

Reference Example 5-1

4-(S)-(1-Ethoxycarbonylcyclopropyl)-3-(R)-fluoro-1-[1-(S)-phenylethyl]-2-pyrrolidone

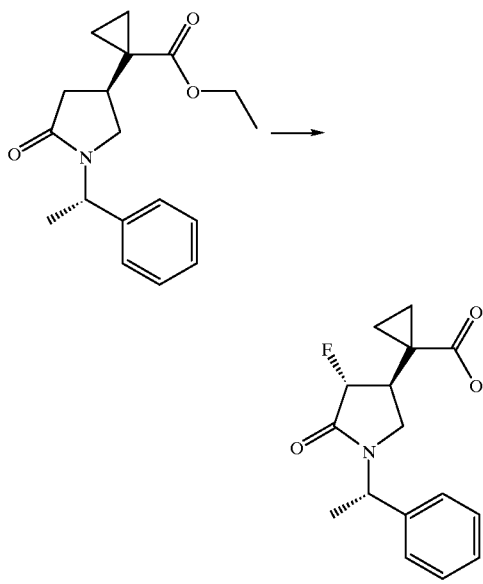

Under a nitrogen atmosphere, diisopropylamine (3.99 ml, 30.4 mmol) was dissolved in anhydrous tetrahydrofuran (50 ml) to which, after cooling to −78° C., was subsequently added dropwise an n-hexane solution of 1.68 M n-butyl lithium (18.1 ml, 30.4 mmol) over a period of 10 minutes. After 20 minutes of stirring at −10° C. and subsequent cooling to −78° C., to the resulting reaction solution was added dropwise an anhydrous tetrahydrofuran solution (30 ml) of 4-(S)-(1-ethoxycarbonylcyclopropyl)-1-[1-(S)-phenylethyl]-2-pyrrolidone (7.052 g, 23.40 mmol) over a period of 15 minutes. The reaction solution was stirred at −78° C. for 1 hour and then an anhydrous tetrahydrofuran solution (60 ml) of N-fluorobenzene disulfonimide (11.81 g, 37.44 mmol) was added dropwise thereto at the same temperature over a period of 25 minutes. The reaction solution was stirred at −78° C. for 2 hours and then at room temperature for 20 minutes. While cooling in an ice bath, the reaction solution was mixed with a saturated ammonium chloride aqueous solution (200 ml), the organic layer was separated and then the aqueous layer was extracted with diethyl ether (200 ml×2). The organic layers were combined, washed with water (200 ml×3) and then dried over anhydrous magnesium sulfate. After filtration, the filtrate was concentrated under reduced pressure, and the resulting residue was subjected to flash silica gel chromatography and eluted with an eluant of n-hexane:ethyl acetate=3:1, to thereby obtain 5.276 g (70.6%) of the title compound as a colorless oil.

$^1$H-NMR (400 MHz, CDCl$_3$) δ: 0.76–0.81 (1 H, m), 0.89–0.93 (1 H, m), 1.09 (3 H, t, J=6.84 Hz), 1.24–1.34 (2 H, m), 1.58 (3 H, d, J=7.33 Hz), 2.23 (1 H, dq, J=28.32, 8.30 Hz), 2.88–2.93 (1 H, m), 3.48 (1 H, t, J=9.28 Hz), 3.92–4.08 (2 H, m), 5.14 (1 H, dd, J=53.71, 7.81 Hz), 5.54 (1 H, q, J=7.33 Hz), 7.27–7.34 (5 H, m).

Reference Example 5-2

4-(S)-(1-Ethoxycarbonylcyclopropyl)-3-(R)-fluoro-1-[1-(S)-phenylethyl]-2-pyrrolidinethione

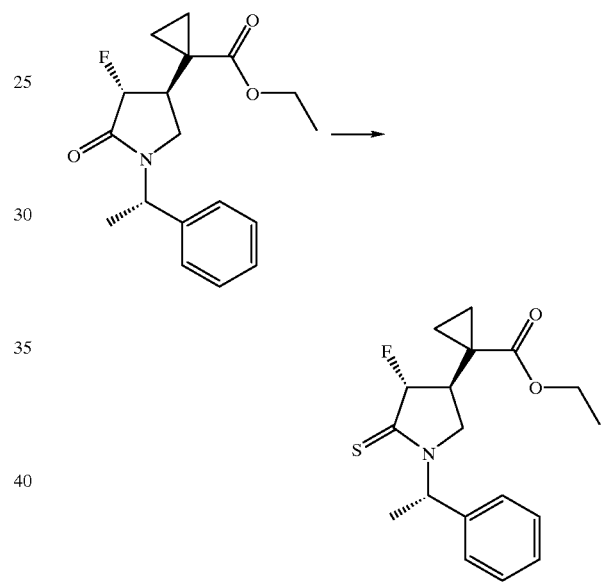

4-(S)-(1-Ethoxycarbonylcyclopropyl)-3-(R)-fluoro-1-[1-(S)-phenylethyl]-2-pyrrolidone (4.825 g, 15.11 mmol) was dissolved in dry benzene (150 ml), and the solution was mixed with Lawesson's reagent (3.085 g, 7.625 mmol) and heated under reflux for 30 minutes. After cooling, benzene was evaporated under a reduced pressure, and the resulting residue was subjected to flash silica gel chromatography and eluted with an eluant of n-hexane:ethyl acetate=5:1, to thereby obtain 4.494 g (88.7%) of the title compound as a light yellow oil.

$^1$H-NMR (400 MHz, CDCl$_3$) δ: 0.75–0.82 (1 H, m), 0.88–0.93 (1 H, m), 1.11 (3 H, t, J=7.33 Hz), 1.25–1.34 (2 H, m), 1.64 (3 H, d, J=7.33 Hz), 2.28 (1 H, dq, J=26.86, 8.30 Hz), 3.12–3.18 (1 H, m), 3.72 (1 H, dd, J=11.23, 9.28 Hz), 3.92–4.08 (2 H, m), 5.22 (1 H, dd, J=53.22, 7.81 Hz), 6.33 (1 H, q, J=7.33 Hz), 7.28–7.38 (5 H, m).

Reference Example 5-3

4-(R)-(1-Ethoxycarbonylcyclopropyl)-3-(S)-fluoro-1-[1-(S)-phenylethyl]pyrrolidine

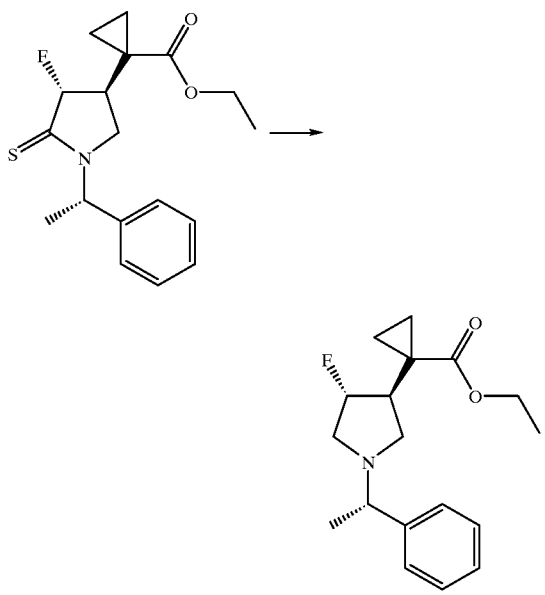

4-(S)-(1-Ethoxycarbonylcyclopropyl)-3-(R)-fluoro-1-[1-(S)-phenylethyl]-2-pyrrolidinethione (4.401 g, 13.12 mmol) was dissolved in anhydrous ethanol (150 ml), and the solution was mixed with Raney nickel (13 ml) and stirred at room temperature for 1 hour. After removing the catalyst by celite filtration (ethanol washing), the resulting filtrate was concentrated under reduced pressure. The thus obtained residue was dissolved in diethyl ether (250 ml), washed with 10% ammonia water (100 ml×5) and saturated brine (100 ml) in that order and then dried over anhydrous magnesium sulfate. After filtration, the filtrate was concentrated under reduced pressure and the resulting residue was subjected to flash silica gel chromatography and eluted with an eluant of n-hexane:ethyl acetate=4:1, to thereby obtain 3.794 g (94.7%) of the title compound as a colorless oil.

$^1$H-NMR (400 MHz, CDCl$_3$) δ: 0.66–0.71 (1 H, m), 0.83–0.88 (1 H, m), 1.19 (3 H, t, J=7.33 Hz), 1.28–1.44 (2 H, m), 1.37 (3 H, d, J=6.84 Hz), 2.02 (1 H, dm, J=29.30 Hz), 2.10 (1 H, q, J=9.28 Hz), 2.67 (1 H, ddd, J=33.20, 11.23, 5.37 Hz), 2.80 (1 H, t, J=7.82 Hz), 3.17 (1 H, q, J=6.84 Hz), 3.33 (1 H, dd, J=22.95, 11.23 Hz), 4.06 (2 H, q, J=7.33 Hz), 5.16 (1 H, dd, J=56.65, 3.41 Hz), 7.21–7.34 (5 H, m).

Reference Example 5-4

1-Benzyloxycarbonyl-4-(R)-(1-ethoxycarbonylcyclopropyl)-3-(S)-fluoropyrrolidine

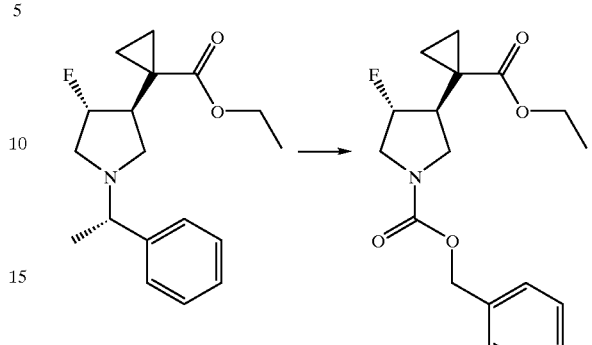

4-(R)-(1-Ethoxycarbonylcyclopropyl)-3-(S)-fluoro-1-[1-(S)-phenylethyl]pyrrolidine (3.786 g, 12.40 mmol) was dissolved in dry dichloromethane (120 ml), and benzyl chloroformate (3.37 ml, 25.0 mmol) was added dropwise to the thus prepared solution which was cooled in an ice bath. After stirring the reaction solution for 25 hours at room temperature, dichloromethane was evaporated under reduced pressure. Thereafter, the resulting residue was subjected to flash silica gel chromatography and eluted with an eluant of n-hexane:ethyl acetate=4:1, to thereby obtain 3.718 g (89.4%) of the title compound as a colorless oil.

$^1$H-NMR (400 MHz, CDCl$_3$) δ: 0.71–0.78 (1 H, m), 0.90–0.95 (1 H, m), 1.23 (3 H, t, J=6.83 Hz), 1.19–1.25 (1 H, m), 1.28–1.32 (1 H, m), 2.48 (1 H, dm, J=28.32 Hz), 3.27 (1 H, t, J=10.25 Hz), 3.67 (1 H, dd, J=23.93, 13.19 Hz), 3.80–3.92 (2 H, m), 4.11 (2 H, q, J=6.83 Hz), 5.14 (2 H, s), 5.17 (1 H, brd, J=55.17 Hz), 7.29–7.35 (5 H, m).

Reference Example 5-5

1-[1-Benzyloxycarbonyl-4-(R)-fluoro-3-(S)-pyrrolidinyl]cyclopropanecarboxylic acid

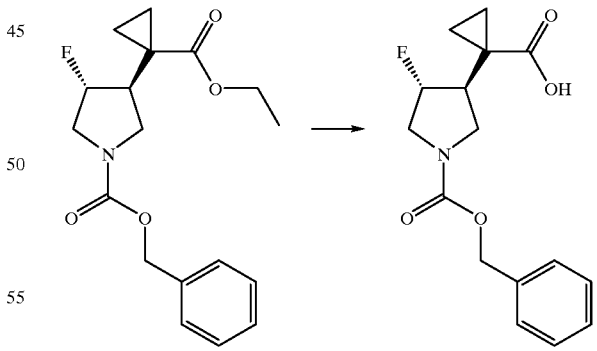

1-Benzyloxycarbonyl-4-(R)-(1-ethoxycarbonylcyclopropyl)-3-(S)-fluoropyrrolidine (3.715 g, 11.08 mmol) was dissolved in ethanol (110 ml), and 10 N sodium hydroxide aqueous solution (11 ml) was added dropwise to the thus prepared solution which was cooled in an ice bath. The reaction solution was stirred at room temperature for 18 hours and then ethanol was evaporated under reduced pressure. The thus obtained residue was mixed with water (50 ml) and washed with dichloromethane (50 ml×2). The thus separated aqueous layer was cooled in an ice bath, acidified by adding dropwise concentrated hydrochloric acid, extracted with diethyl ether (100 ml×5) and then dried over anhydrous magnesium sulfate. After filtration, the filtrate was concentrated under reduced pressure, and the residue was dissolved in benzene (100 ml) and again concentrated under reduced pressure. This azeotropic step with benzene was repeated 3 times to obtain 3.346 g (98.3%) of the title compound as a colorless amorphous substance.

$^1$H-NMR (400 MHz, CDCl$_3$) δ: 0.84–0.89 (1 H, m), 0.99–1.07 (1 H, m), 1.32–1.42 (2 H, m), 2.37–2.56 (1 H, m), 3.26–3.31 (1 H, m), 3.58–3.67 (1 H, m), 3.82–3.88 (2 H, m), 5.13 (1 H, s), 5.20 (1 H, brd, J=54.96 Hz), 7.30–7.34 (5 H, m).

Reference Example 5-6

1-Benzyloxycarbonyl-4-(R)-(1-tert-butoxycarbonylaminocyclopropyl)-3-(R)-fluoropyrrolidine

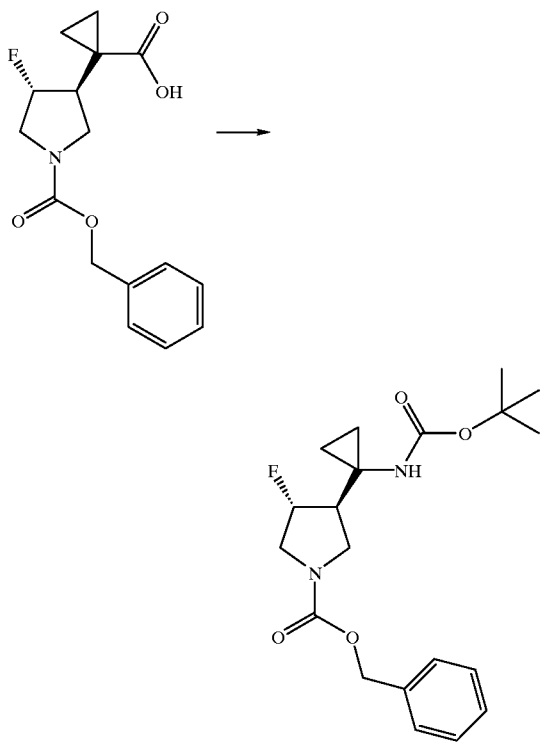

1-[1-Benzyloxycarbonyl-4-(R)-fluoro-3-(S)-pyrrolidinyl] cyclopropanecarboxylic acid (3.342 g, 10.87 mmol) was dissolved in tert-butyl alcohol (100 ml), and the solution was mixed with diphenylphosphoryl acid azide (2,398 μl, 11.11 mmol) and triethylamine (2,273 μl, 16.31 mmol), stirred at room temperature for 2 hours and then heated under reflux for 14 hours. The reaction solution was cooled and then concentrated under reduced pressure, and the resulting residue was subjected to flash silica gel chromatography and eluted with an eluant of n-hexane:ethyl acetate=3:1, to thereby obtain 2.682 g (65.2%) of the title compound as a colorless oil.5

$^1$H-NMR (400 MHz, CDCl$_3$) δ: 0.64–0.70 (1 H, m), 0.79–0.83 (1 H, m), 0.86–1.09 (2 H, m), 1.39 (9 H, s), 2.21 (1 H, dm, J=21.48 Hz), 3.44 (1 H, dd, J=11.23, 2.93 Hz), 3.59–3.76 (3 H, m), 4.91 (1 H, brs), 5.14 (2 H, s), 5.40 (1 H, brd, J=52.74 Hz), 7.28–7.33 (5 H, m).

Example 5

5-Amino-7-[4-(R)-(1-aminocyclopropyl)-3-(R)-fluoro-1-pyrrolidinyl]-6-fluoro-1-[2-(S)-fluoro-1-(R)-cyclopropyl]-1,4-dihydro-8-methyl-4-oxoquinoline-3-carboxylic acid hydrochloride

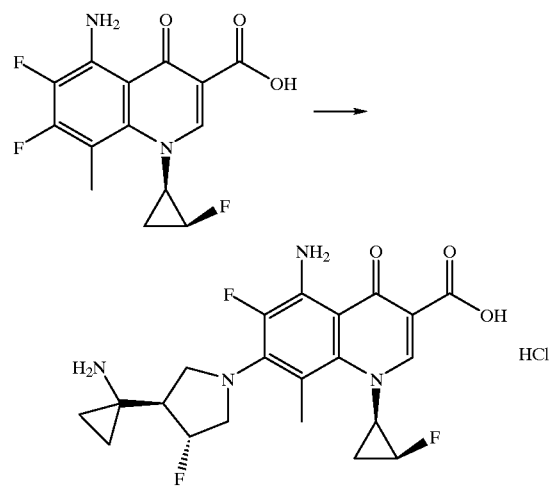

1-Benzyloxycarbonyl-4-(R)-(1-tert-butoxycarbonylaminocyclopropyl)-3-(R)-fluoropyrrolidine (757.8 mg, 2.002 mmol) was dissolved in methanol (80 ml), and the solution was mixed with a 5% palladium-carbon catalyst (water content, 55.6%; 800 mg) and stirred for 7 hours under a pressured hydrogen atomosphere (4.5 kg/cm$^2$). The catalyst was removed by celite filtration (methanol washing), and the filtrate was concentrated under reduced pressure. The thus obtained residue was dissolved in dimethyl sulfoxide (8 ml), and the solution was mixed with 5-amino-6,7-difluoro-1-[2-(S)-fluoro-1-(R)-cyclopropyl]-1, 4-dihydro-8-methyl-4-oxoquinoline-3-carboxylic acid (404.7 mg, 1.296 mmol) and triethylamine (3 ml) and stirred for 4 days in an oil bath of 120° C. under a nitrogen atmosphere. After cooling, dimethyl sulfoxide was evaporated under reduced pressure, the thus obtained residue was dissolved in chloroform (150 ml) and washed with 10% citric acid aqueous solution (100 ml×2) and saturated brine (100 ml) in that order and then the organic layer was dried over anhydrous magnesium sulfate. After filtration, the filtrate was concentrated under reduced pressure. To the thus obtained residue, which was cooled in an ice bath, was added dropwise concentrated hydrochloric acid (10 ml), followed by stirring at room temperature for 15 minutes. After adding water (10 ml) to the reaction solution, the aqueous solution was washed with dichloromethane (30 ml×4), adjusted to pH 7.4 with sodium hydroxide aqueous solution and then extracted with chloroform (100 ml×4). The organic layers were combined, dried over anhydrous magnesium sulfate and then filtered, and the filtrate was concentrated under reduced pressure. The thus obtained residue was subjected to preparative silica gel thin layer chromatography (development with the bottom layer of a mixed solvent of chloroform:methanol:water=7:3:1), and then the thus obtained crude product was dissolved in ethanol (20 ml). 1 N hydrochloric acid (1.5 ml) was added dropwise thereto under ice-cooling, and the resulting reaction solution was stirred for 5 minutes at the same temperature and then concentrated under reduced pressure (ethanol azeotropic treatment was conducted three times). Thereafter, the resulting residue was purified by recrystallization from ethanol-diisopropyl ether and then dried under reduced pressure to obtain 141.8 mg (22.3%) of the title compound as a yellow powder.

Melting point: 220.2–224.9° C. (decomposition)

$^1$H-NMR (400 MHz, 0.1 N NaOD) δ: 0.58–0.68 (4 H, m), 1.11–1.25 (1 H, m), 1.52–1.59 (1 H, m), 2.41 (3 H, s), 2.39–2.49 (1 H, m), 3.39 (1 H, t, J=9.27 Hz), 3.58–3.67 (1 H, m), 3.71–3.83 (2 H, m), 3.88–3.99 (1 H, m), 4.96 (1 H, dm, J=65.86 Hz), 5.49 (1 H, brd, J=54.69 Hz), 8.27 (1 H, d, J=3.41 Hz).

Elemental analysis data; for $C_{21}H_{23}F_3N_4O_3 \cdot HCl \cdot H_2O$: calcd.; C, 51.38; H, 5.34; N, 11.41 found; C, 51.21; H, 5.38; N, 11.22

Example 6

10-[4-(R)-(1-Aminocyclopropyl)-3-(R)-fluoro-1-pyrrolidinyl]-9-fluoro-2,3-dihydro-3-(S)-methyl-7-oxo-7H-pyrido[1.2.3-de][1.4]benzoxazine-6-carboxylic acid

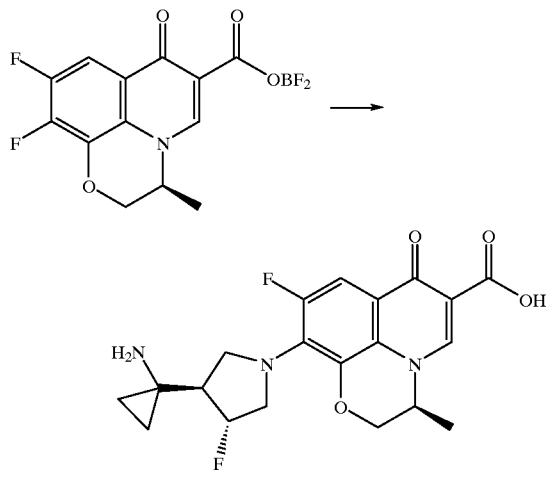

1-Benzyloxycarbonyl-4-(R)-(1-tert-butoxycarbonylaminocyclopropyl)-3-(R)-fluoropyrrolidine (759.9 mg, 2.008 mmol) was dissolved in methanol (80 ml), and the solution was mixed with a 5% palladium-carbon catalyst (water content, 55.6%; 800 mg) and stirred for 7 hours under a pressured hydrogen atmosphere (4.5 kg/cm$^2$). The catalyst was removed by celite filtration (methanol washing), and the filtrate was concentrated under reduced pressure. The thus obtained residue was dissolved in dimethyl sulfoxide (8 ml), and the solution was mixed with 9,10-difluoro-2,3-dihydro-3-(S)-methyl-7-oxo-7H-pyrido[1.2.3-de][1.4]benzoxazine-6-carboxylic acid-BF$_2$ chelate (440.9 mg, 1.340 mmol) and triethylamine (374 μl, 2.68 mmol) and stirred at room temperature for 20 hours. After concentrating the reaction solution under reduced pressure, the resulting residue was mixed with water, and the thus precipitated yellow crystals were collected by filtration and washed with water. The thus obtained crystals were suspended in a solution of methanol:water=9:1 (20 ml), and the suspension was mixed with triethylamine (1 ml) and heated under reflux for 4 hours. After cooling, the reaction solution was concentrated under reduced pressure, and the thus obtained residue was dissolved in chloroform (100 ml) and washed with 10% citric acid aqueous solution (100 ml×2) and saturated brine (100 ml) in that order and then the organic layer was dried over anhydrous magnesium sulfate. After filtration, the filtrate was concentrated under reduced pressure. To the thus obtained residue, which was cooled in an ice bath, was added dropwise concentrated hydrochloric acid (10 ml), followed by 15 minutes of stirring at room temperature. After adding water (10 ml) to the reaction solution, the aqueous solution was washed with dichloromethane (30 ml×2), adjusted to pH 7.2 with a sodium hydroxide aqueous solution and then extracted with chloroform (100 ml×4). The organic layers were combined, dried over anhydrous magnesium sulfate and then filtered, and the filtrate was concentrated under reduced pressure. Thereafter, the resulting residue was purified by recrystallization from a mixture of ethanol and 28% ammonia water, and then dried under reduced pressure to obtain 370.8 mg (67.5%) of the title compound as light yellow crystals.

Melting point: 240.6–243.4° C. (decomposition)

$^1$H-NMR (400 MHz, 0.1 N NaOD) δ: 0.59–0.68 (4 H, m), 1.52 (3 H, d, J=6.84 Hz), 2.39 (1 H, dt, J=29.30, 7.81 Hz), 3.37 (1 H, t, J=7.81 Hz), 3.74–3.90 (3 H, m), 3.95 (1 H, t, J=9.76 Hz), 4.36 (1 H, d, J=10.26 Hz), 4.53 (1 H, d, J=11.23 Hz), 4.62 (1 H, q, J=6.84 Hz), 5.34 (1 H, brd, J=54.20 Hz), 7.57 (1 H, d, J=13.67 Hz), 8.35 (1 H, s).

Elemental analysis data; for $C_{20}H_{21}F_2N_3O_4 \cdot 0.25H_2O$: calcd.; C, 58.60; H, 5.29; N, 10.25 found; C, 58.42; H, 5.35; N, 10.01

Reference Example 6-1

4-(S)-(1-Ethoxycarbonylcyclopropyl)-3,3-difluoro-1-[1-(S)-phenylethyl]-2-pyrrolidone

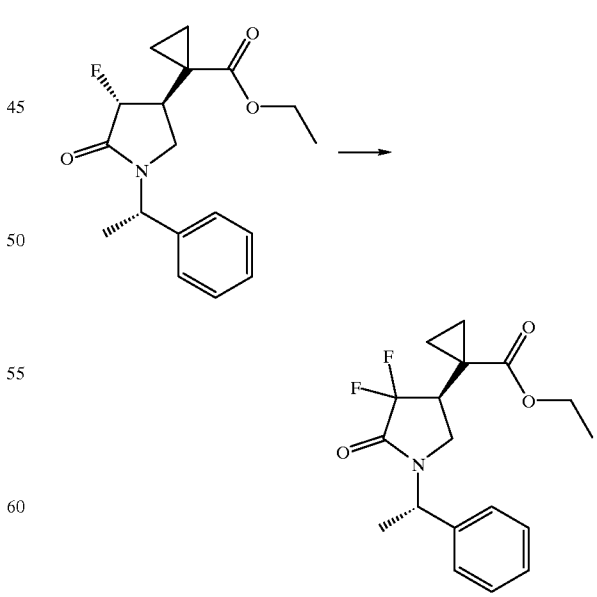

Under a nitrogen atmosphere, diisopropylamine (2.49 ml, 19.0 mmol) was dissolved in anhydrous tetrahydrofuran (25 ml) to which, after cooling to −78° C., was subsequently added dropwise an n-hexane solution of 1.68 M n-butyl lithium (11.2 ml, 18.8 mmol) in 10 minutes. After 20 minutes of stirring at −10° C. and subsequent cooling to −78° C., to the resulting reaction solution was added dropwise an anhydrous tetrahydrofuran solution (15 ml) of 4-(S)-(1-ethoxycarbonylcyclopropyl)-3-(R)-fluoro-1-[1-(S)-phenylethyl]-2-pyrrolidone (5.011 g, 15.69 mmol) over a period of 15 minutes. After 30 minutes of stirring at −78° C., to the reaction solution cooled at the same temperature was added dropwise an anhydrous tetrahydrofuran solution (35 ml) of N-fluorobenzene disulfonimide (7.421 g, 23.54 mmol) over a period of 20 minutes. The reaction solution was stirred at −78° C. for 2 hours and then at room temperature for 1 hour While cooling in an ice bath, the reaction solution was mixed with a saturated ammonium chloride aqueous solution (100 ml), the organic layer was separated and then the water layer was extracted with diethyl ether (100 ml×3). The organic layers were combined, washed with water (100 ml×2) and then dried over anhydrous magnesium sulfate. After filtration, the filtrate was concentrated under reduced pressure, and the resulting residue was subjected to flash silica gel chromatography and eluted with an eluant of n-hexane:ethyl acetate=4:1, to thereby obtain 3.637 g (68.7%) of the title compound as a colorless oil.

$^1$H-NMR (400 MHz, CDCl$_3$) δ: 0.76–0.82 (1 H, m), 0.87–0.94 (1 H, m), 1.09 (3 H, t, J=6.83 Hz), 1.23–1.36 (2 H, m), 1.58 (3 H, d, J=7.33 Hz), 2.56–2.69 (1 H, m), 2.92–2.98 (1 H, m), 3.53 (1 H, td, J=10.93, 2.91 Hz), 3.84–3.92 (1 H, m), 4.02–4.10 (1 H, m), 5.53 (1 H, q, J=7.33 Hz), 7.28–7.35 (5 H, m).

Reference Example 6-2

4-(S)-(1-Ethoxycarbonylcyclopropyl)-3,3-difluoro-1-[1-(S)-phenylethyl]-2-pyrrolidinethione

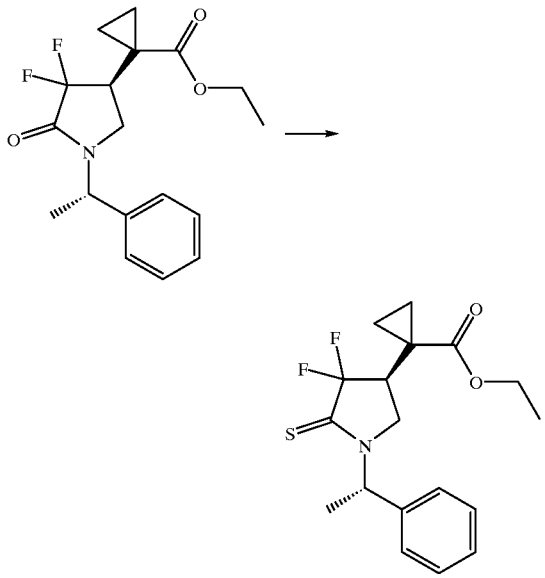

4-(S)-(1-Ethoxycarbonylcyclopropyl)-3,3-difluoro-1-[1-(S)-phenylethyl]-2-pyrrolidone (3.621 g, 10.73 mmol) was dissolved in dry benzene (100 ml), and the solution was mixed with Lawesson's reagent (2.192 g, 5.420 mmol) and heated under reflux for 1 hour. After cooling, benzene was evaporated under reduced pressure, and the resulting residue was subjected to flash silica gel chromatography and eluted with an eluant of n-hexane:ethyl acetate=5:1, to thereby obtain 2.886 g (76.1%) of the title compound as a light yellow oil.

$^1$H-NMR (400 MHz, CDCl$_3$) δ: 0.85–0.95 (2 H, m), 1.10 (3 H, t, J=6.84 Hz), 1.24–1.32 (2 H, m), 1.64 (3 H, d, J=7.33 Hz), 2.69–2.81 (1 H, m), 3.20 (1 H, ddd, J=11.72, 6.84, 2.93 Hz), 3.73 (1 H, td, J=10.26, 2.54 Hz), 3.84–3.92 (1 H, m), 4.02–4.11 (1 H, m), 6.31 (1 H, q, J=7.33 Hz), 7.32–7.38 (5 H, m).

Reference Example 6-3

4-(R)-(1-Ethoxycarbonylcyclopropyl)-3,3-difluoro-1-[1-(S)-phenylethyl]pyrrolidine

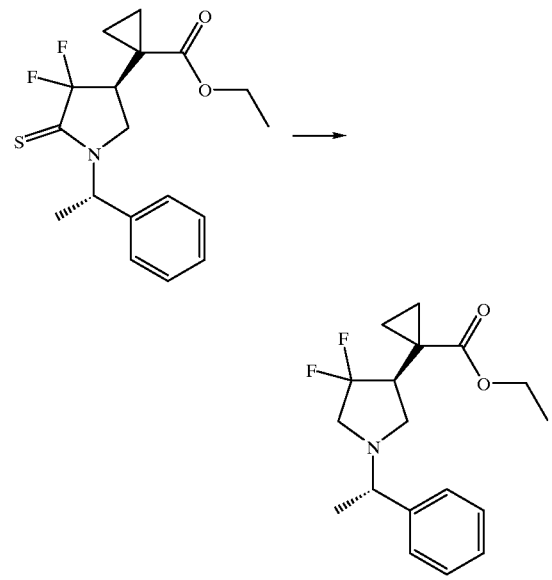

4-(S)-(1Ethoxycarbonylcyclopropyl)-3,3-difluoro-1-[1-(S)-phenylethyl]-2-pyrrolidinethione (2.883 g, 8.157 mmol) was dissolved in anhydrous ethanol (80 ml), and the solution was mixed with Raney nickel (8 ml) and stirred at room temperature for 30 minutes. After removing the catalyst by celite filtration (ethanol washing), the resulting filtrate was concentrated under reduced-pressure. The thus obtained residue was dissolved in diethyl ether (150 ml), washed with 10% ammonia water (100 ml×4) and saturated brine (100 ml) in that order and then dried over anhydrous magnesium sulfate. After filtration, the filtrate was concentrated under reduced pressure and the resulting residue was subjected to flash silica gel chromatography and eluted with an eluant of n-hexane:ethyl acetate=4:1, to thereby obtain 2.540 g (96.3%) of the title compound as a colorless oil.

$^1$H-NMR (400 MHz, CDCl$_3$) δ: 0.67–0.89 (2 H, m), 1.19 (3 H, t, J=7.33 Hz), 1.27–1.46 (2 H, m), 1.38 (3 H, d, J=7.33 Hz), 2.34–2.62 (2 H, m), 2.68–2.96 (2 H, m), 3.20 (1 H, q, J=7.33 Hz), 3.52–3.48 (1 H, m), 3.94–4.09 (2 H, m), 7.28–7.34 (5 H, m).

Reference Example 6-4

1-Benzyloxycarbonyl-4-(R)-(1-ethoxycarbonylcyclopropyl)-3,3-difluoropyrrolidine

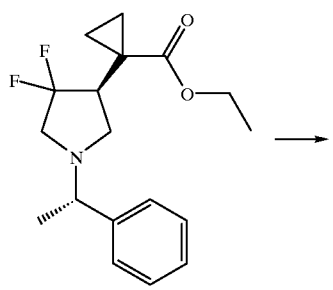

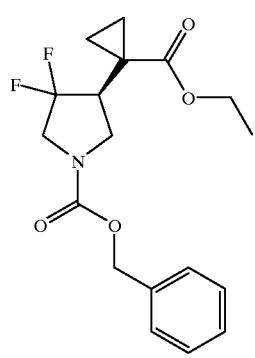

4-(R)-(1-Ethoxycarbonylcyclopropyl)-3,3-difluoro-1-[1-(S)-phenylethyl]pyrrolidine(2.536 g, 7.842 mmol) was dissolved in dry dichloromethane (80 ml), and benzyl chloroformate (2.80 ml, 19.6 mmol) was added dropwise to the thus prepared solution which was cooled in an ice bath. The reaction solution was stirred at room temperature for 44 hours and then dichloromethane was evaporated under reduced pressure. Thereafter, the resulting residue was subjected to flash silica gel chromatography and eluted with an eluant of n-hexane:ethyl acetate=4:1, to thereby obtain 2.294 g (82.8%) of the title compound as a colorless oil.

$^1$H-NMR (400 MHz, CDCl$_3$) δ: 0.97–1.05 (1 H, m), 1.07–1.16 (1 H, m), 1.22 (3 H, t, J=7.33 Hz), 1.20–1.30 (1 H, m), 1.32–1.42 (1 H, m), 2.93–3.07 (1 H, m), 3.36–3.44 (1 H, m), 3.77–3.84 (2 H, m), 3.93 (1 H, t, J=10.74 Hz), 4.12 (2 H, qd, J=7.33, 1.47 Hz), 5.14 (2 H, s), 7.28–7.35 (5 H, m).

Reference Example 6-5

1-[1-Benzyloxycarbonyl-4,4-difluoro-3-(S)-pyrrolidinyl]cyclopropanecarboxylic acid

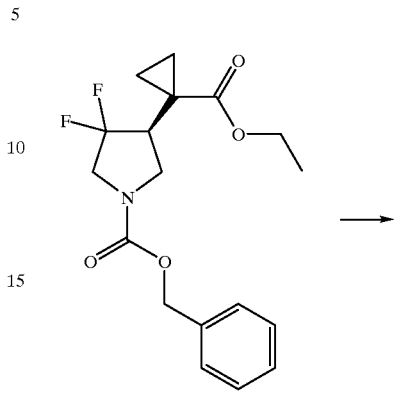

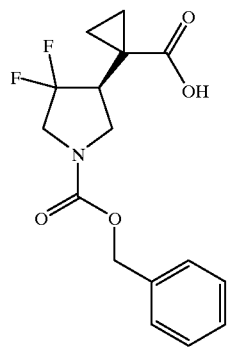

1-Benzyloxycarbonyl-4-(R)-(1-ethoxycarbonylcyclopropyl)-3,3-difluoropyrrolidine (2.287 g, 6.472 mmol) was dissolved in ethanol (65 ml) to which, while cooling in an ice bath, was added dropwise a 10 N sodium hydroxide aqueous solution (6.5 ml). The reaction solution was stirred at room temperature for 16 hours and then ethanol was evaporated under reduced pressure. The thus obtained residue was mixed with water (50 ml) and washed with dichloromethane (50 ml×2), and the thus separated aqueous layer was cooled in an ice bath, acidified by adding dropwise concentrated hydrochloric acid and then extracted with diethyl ether (100 ml×5), subsequently drying the extract over anhydrous magnesium sulfate. After filtration, the filtrate was concentrated under reduced pressure, and the thus obtained residue was dissolved in benzene (100 ml) and again concentrated under reduced pressure. This azeotropic treatment with benzene was repeated 3 times to obtain 1.956 g (92.9%) of the title compound as a colorless oil.

$^1$H-NMR (400 MHz, CDCl$_3$) δ: 1.08–1.14 (1 H, m), 1.19–1.28 (1 H, m), 1.37–1.42 (1 H, m), 1.44–1.49 (1 H, m), 2.93–3.09 (1 H, m), 3.37–3.46 (1 H, m), 3.76–3.85 (2 H, m), 3.92–4.00 (1 H, m), 5.14 (2 H, s), 7.29–7.34 (5 H, m).

Reference Example 6-6

1-Benzyloxycarbonyl-4-(R)-(1-tert-butoxycarbonylaminocyclopropyl)-3,3-difluoropyrrolidine

Example 7

5-Amino-7-[4-(R)-(1-aminocyclopropyl)-3,3-difluoro-1-pyrrolidinyl]-6-fluoro-1-[2-(S)-fluoro-1-(R)-cyclopropyl]-1,4-dihydro-8-methyl-4-oxoquinoline-3-carboxylic acid hydrochloride

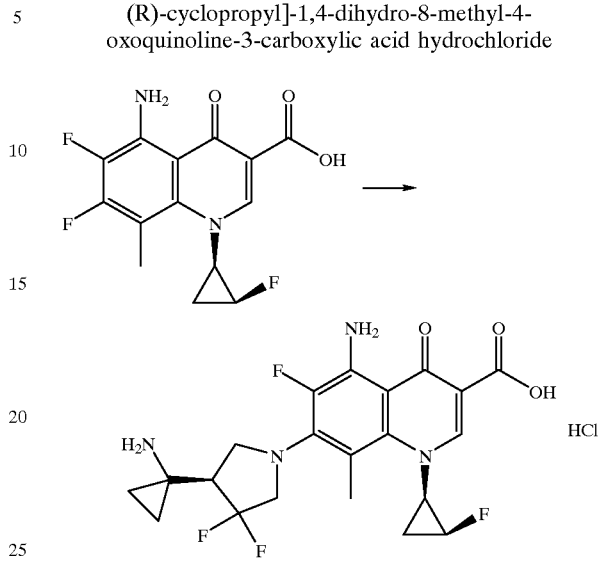

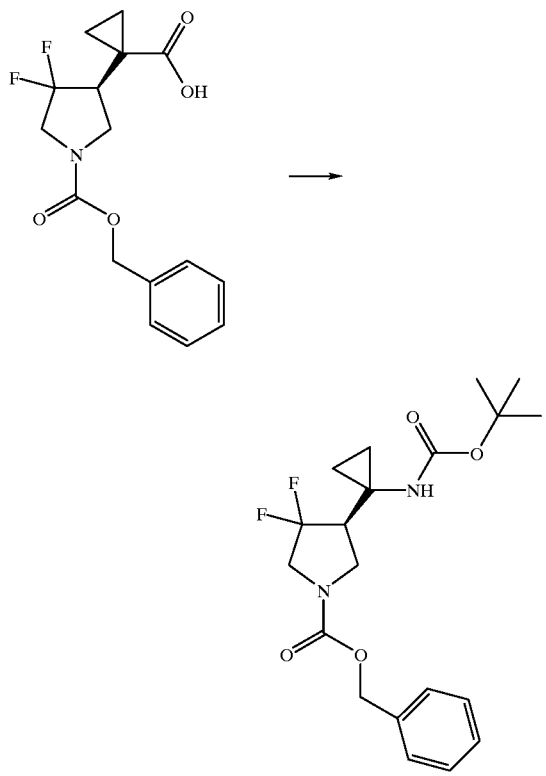

1-[12-Benzyloxycarbonyl-4,4-difluoro-3-(S)-pyrrolidinyl]cyclopropanecarboxylic acid (1.953 g, 6.004 mmol) was dissolved in tert-butyl alcohol (50 ml), and the solution was mixed with diphenylphosphoryl azide (1,426 $\mu$l, 6.604 mmol) and triethylamine (1,381 $\mu$l, 9.906 mmol), stirred at room temperature for 2 hours and then heated under reflux for 16 hours. The reaction solution was cooled and then concentrated under reduced pressure, and the resulting residue was subjected to flash silica gel chromatography and eluted with an eluant of n-hexane:ethyl acetate=4:1, to thereby obtain 1.430 g (60.1%) of the title compound as a colorless oil.

$^1$H-NMR (400 MHz, CDCl$_3$) δ: 0.83–0.92 (2 H, m), 1.40 (9 H, s), 1.34–1.55 (2 H, m), 2.38–2.51 (1 H, m), 3.47 (1 H, t, J=9.28 Hz), 3.67–3.84 (2 H, m), 4.99 (1 H, brs), 5.13 (2 H, s), 7.29–7.35 (5 H, m).

1-Benzyloxycarbonyl-4-(R)-(1-tert-butoxycarbonylaminocyclopropyl)-3,3-difluoropyrrolidine (792.4 mg, 1.999 mmol) was dissolved in methanol (80 ml), and the solution was mixed with a 5% palladium-carbon catalyst (water content, 55.6%; 800 mg) and stirred for 6 hours under a pressured hydrogen atmosphere (4.5 kg/cm$^2$). The catalyst was removed by celite filtration (methanol washing), and the filtrate was concentrated under reduced pressure. The thus obtained residue was dissolved in dimethyl sulfoxide (8 ml), and the solution was mixed with 5-amino-6,7-difluoro-1-[2-(S)-fluoro-1-(R)-cyclopropyl]-1,4-dihydro-8-methyl-4-oxoquinoline-3-carboxylic acid (416.2 mg, 1.333 mmol) and triethylamine (3 ml) and stirred for 5 days in an oil bath of 120° C. under a nitrogen atmosphere. After cooling, dimethyl sulfoxide was evaporated under reduced pressure, the thus obtained residue was dissolved in chloroform (150 ml) and washed with a 10% citric acid aqueous solution (100 ml×2) and saturated brine (100 ml) in that order and then the organic layer was dried over anhydrous magnesium sulfate. After filtration, the filtrate was concentrated under reduced pressure. To the thus obtained residue, which was cooled in an ice bath, was added dropwise concentrated hydrochloric acid (10 ml), followed by 15 minutes of stirring at room temperature. After adding water (10 ml) to the reaction solution, the aqueous solution was washed with dichloromethane (30 ml×5); adjusted to pH 7.4 with sodium hydroxide aqueous solution and then extracted with chloroform (100 ml×4). The organic layers were combined, dried over anhydrous magnesium sulfate and then filtered, and the filtrate was concentrated under reduced pressure. The thus obtained residue was subjected to preparative silica gel thin layer chromatography (development with the bottom layer of a mixture of chloroform:methanol:water=7:3:1), and the thus obtained crude product was dissolved in ethanol (20 ml). While cooling in an ice bath, 1 N hydrochloric acid (1.5 ml) was added dropwise thereto, and the reaction solution was stirred at the same temperature for 5 minutes and then concentrated under reduced pressure (ethanol azeotropic treatment was conducted three times). Thereafter, the resulting residue was purified by recrystallization from ethanol-diisopropyl ether and then dried under reduced pressure to obtain 137.4 mg (19.9%) of the title compound as a yellow powder.

Melting point: 211.2–215.4° C. (decomposition)

$^1$H-NMR (400 MHz, 0.1 N NaOD) δ: 0.59–0.71 (4 H, m), 1.08–1.20 (1 H, m), 1.48–1.57 (1 H, m), 2.30 (3 H, s), 2.25–2.33 (1 H, m), 3.37–2.54 (1 H, m), 3.88 (1 H, t, J=9.28 Hz), 3.90–3.95 (1 H, m), 3.97–4.04 (1 H, m), 4.96 (1 H, dm, J=65.92 Hz), 8.25 (1 H, d, J=2.93 Hz).

Elemental analysis data; for $C_{21}H_{22}F_4N_4O_3 \cdot HCl \cdot 1.5H_2O$: calcd.; C, 48.70; H, 5.05; N, 10.82 found; C, 48.58; H, 5.11; N, 10.66

Example 8

10-[4-(R)-(1-Aminocyclopropyl)-3,3-difluoro-1-pyrrolidinyl]-9-fluoro-2,3-dihydro-3-(S)-methyl-7-oxo-7H-pyrido[1.2.3-de][1.4]benzoxazine-6-carboxylic acid

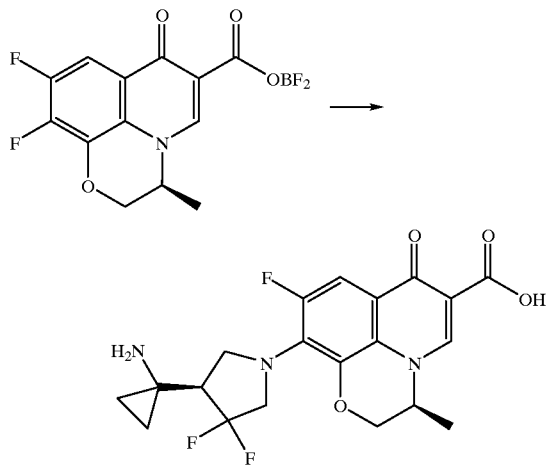

1-Benzyloxycarbonyl-4-(R)-(1-tert-butoxycarbonylaminocyclopropyl)-3,3-difluoropyrrolidine (628.8 mg, 1.586 mmol) was dissolved in methanol (60 ml), and the solution was mixed with a 5% palladium-carbon catalyst (water content, 55.6%; 650 mg) and stirred for 7 hours under a pressured hydrogen atomosphere (4.5 kg/cm$^2$). The catalyst was removed by celite filtration (methanol washing), and the filtrate was concentrated under reduced pressure. The thus obtained residue was dissolved in dimethyl sulfoxide (8 ml), and the solution was mixed with 9,10-difluoro-2,3-dihydro-3-(S)-methyl-7-oxo-7H-pyrido[1.2.3-de][1.4]benzoxazine-6-carboxylic acid-BF$_2$ chelate (347.9 mg, 1.057 mmol) and triethylamine (294 μl, 2.11 mmol) and stirred at room temperature for 41 hours. After concentration of the reaction solution under reduced pressure, the resulting residue was mixed with water, and the thus precipitated yellow crystals were collected by filtration and washed with water. The thus obtained crystals were suspended in a solution of methanol:water=9:1 (20 ml), and the suspension was mixed with triethylamine (1 ml) and heated under reflux for 5 hours. After cooling, the reaction solution was concentrated under reduced pressure, and the thus obtained residue was dissolved in chloroform (100 ml) and washed with 10% citric acid aqueous solution (100 ml×2) and saturated brine (100 ml) in that order and then the organic layer was dried over anhydrous magnesium sulfate. After filtration, the filtrate was concentrated under reduced pressure. To the thus obtained residue, which was cooled in an ice bath, was added dropwise concentrated hydrochloric acid (10 ml), followed by 15 minutes of stirring at room temperature. After adding water (10 ml) to the reaction solution, the aqueous solution was washed with dichloromethane (30 ml×3), adjusted to pH 7.2 with sodium hydroxide aqueous solution and then extracted with chloroform (100 ml×4). The organic layers were combined, dried over anhydrous magnesium sulfate and then filtered, and the filtrate was concentrated under reduced pressure. Thereafter, the resulting residue was purified by recrystallization from a mixture of ethanol and 28% ammonia water, and then dried under reduced pressure to obtain 183.8 mg (41.1%) of the title compound as light yellow crystals.

Melting point: 246.7–248.0° C. (decomposition)

$^1$H-NMR (400 MHz, 0.1 N NaOD) δ: 0.61–0.72 (4 H, m), 1.53 (3 H, d, J=6.83 Hz), 2.36–2.45 (1 H, m), 3.74–3.94 (3 H, m), 4.08–4.14 (1 H, m), 4.37 (1 H, d, J=10.74 Hz), 4.53 (1 H, d, J=10.74 Hz), 4.61–4.64 (1 H, m), 7.60 (1 H, d, J=13.68 Hz), 8.36 (1 H, s).

Elemental analysis data; for $C_{20}H_{20}F_3N_3O_4$: calcd.; C, 56.74; H, 4.76; N, 9.92 found; C, 56.72; H, 4.66; N, 9.74

Reference Example 7-1

4-(S)-(1-Ethoxycarbonylcyclopropyl)-3-(S)-fluoro-1-[1-(S)-phenylethyl]-2-pyrrolidone

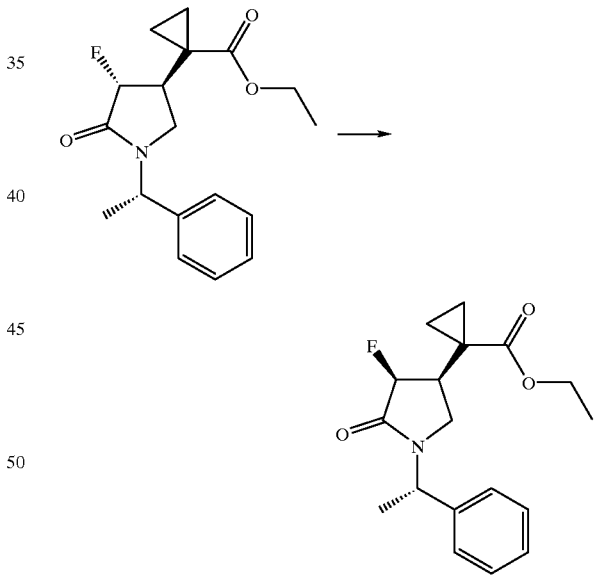

Under a nitrogen atmosphere, diisopropylamine (7.22 ml, 51.52 mmol) was dissolved in anhydrous tetrahydrofuran (100 ml) to which, after cooling to −78° C., was subsequently added dropwise an n-hexane solution of 1.68 M n-butyl lithium (28.1 ml, 47.21 mmol) over a period of 15 minutes. After 10 minutes of stirring at 0° C. and subsequent cooling to −78° C., to the resulting reaction solution was added dropwise an anhydrous tetrahydrofuran solution (40 ml) of 4-(S)-(1-ethoxycarbonylcyclopropyl)-3-(R)-fluoro-1-[1-(S)-phenylethyl]-2-pyrrolidone (13.72 g, 42.96 mmol) over a period of 20 minutes. After an additional 20 minutes of stirring at −78° C., to the reaction solution was added dropwise 2,6-di-tert-butylphenol (10.63 g, 51.52 mmol) dissolved in anhydrous tetrahydrofuran (40 ml) over a period of 20 minutes. The reaction solution was stirred at −78° C. for 10 minutes and then warmed to room temperature. While cooling in an ice bath, the resulting reaction solution was mixed with a saturated ammonium chloride aqueous solution (200 ml), the organic layer was separated and then the aqueous layer was extracted with diethyl ether (200 ml×2). The organic layers were combined, washed with water (400 ml×2) and then dried over anhydrous sodium sulfate. After filtration, the filtrate was concentrated under reduced pressure, and the resulting residue was subjected to flash silica gel chromatography and eluted with an eluant of n-hexane: ethyl acetate=3:1, to thereby obtain 10.19 g (74.2%) of the title compound as a colorless oil.

$^1$H-NMR (400 MHz, CDCl$_3$) δ: 0.57–0.63 (1 H, m), 0.78–0.84 (1 H, m), 1.07–1.13 (1 H, m), 1.26 (3 H, t, J=7.09 Hz), 1.23–1.29 (1 H, m), 1.54 (3 H, d, J=7.32 Hz), 2.59 (1 H, t, J=9.77 Hz), 3.05 (1 H, dq, J=28.81, 8.30 Hz), 3.25 (1 H, t, J=9.77 Hz), 4.00–4.16 (2 H, m), 5.15 (1 H, dd, J=52.73, 6.35 Hz), 5.53 (1 H, q, J=7.32 Hz), 7.27–7.38 (5 H, m).

Reference Example 7-2

4-(S)-(1-Ethoxycarbonylcyclopropyl)-3-(S)-fluoro-1-[1-(S)-phenylethyl]-2-pyrrolidinethione

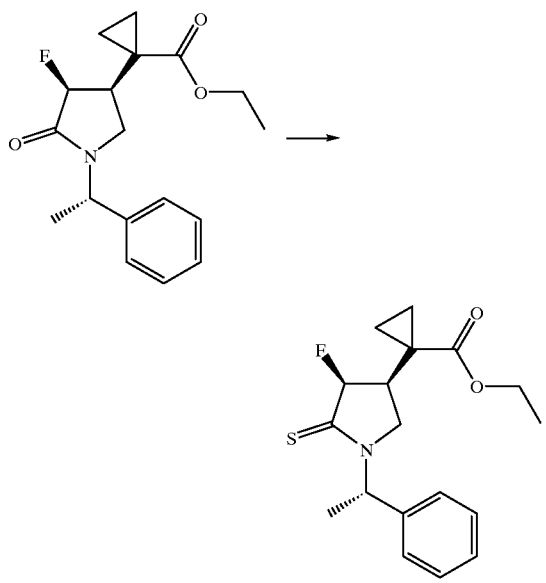

4-(S)-(1-Ethoxycarbonylcyclopropyl)-3-(S)-fluoro-1-[1-(S)-phenylethyl]-2-pyrrolidone (6.86 g, 21.48 mmol) was dissolved in dry toluene (100 ml), and the solution was mixed with Lawesson's reagent (5.21 g, 12.89 mmol) and heated at 60° C. for 30 minutes. After cooling, toluene was evaporated under reduced pressure, and the resulting residue was subjected to flash silica gel chromatography and eluted with an eluant of n-hexane:ethyl acetate=4:1, to thereby obtain 6.49 g (90.1%) of the title compound as a light yellow oil.

$^1$H-NMR (400 MHz, CDCl$_3$) δ: 0.59–0.66 (1 H, m), 0.86–0.92 (1 H, m), 1.08–1.15 (1 H, m), 1.20 (3 H, t, J=7.33 Hz), 1.24–1.31 (1 H, m), 1.60 (3 H, d, J=7.32 Hz), 2.85 (1 H, dd, J=11.23, 9.28 Hz), 3.16 (1 H, dq, J=30.27, 8.30 Hz), 3.50 (1 H, dd, J=11.23, 9.28 Hz), 4.04–4.15 (2 H, m), 5.32 (1 H, dd, J=52.73, 5.38 Hz), 6.28–6.34 (1 H, m), 7.30–7.41 (5 H, m).

Reference Example 7-3

4-(S)-(1-Ethoxycarbonylcyclopropyl)-3-(S)-fluoro-1-[1-(S)-phenylethyl]pyrrolidine

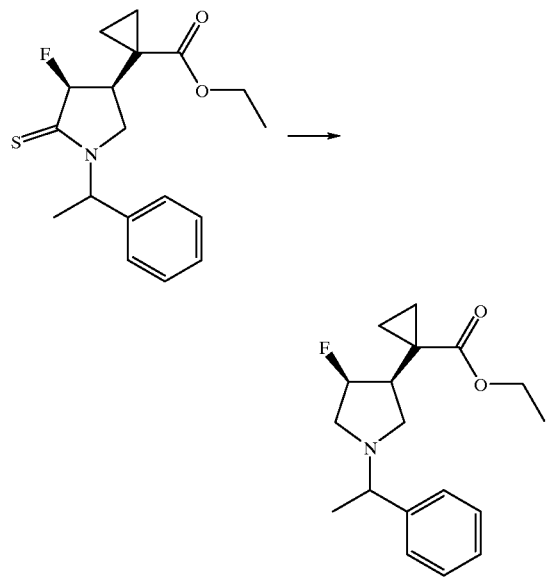

4-(S)-(1-Ethoxycarbonylcyclopropyl)-3-(S)-fluoro-1-[1-(S)-phenylethyl]-2-pyrrolidinethione (6.49 g, 19.35 mmol) was dissolved in anhydrous tetrahydrofuran (150 ml), and the solution was mixed with Raney nickel (15 ml) and stirred at room temperature for 30 minutes. After removing the catalyst by celite filtration (tetrahydrofuran washing), the resulting filtrate was concentrated under reduced pressure. The thus obtained residue was dissolved in diethyl ether (200 ml), washed with 10% ammonia water (200 ml×2) and saturated brine (150 ml) in that order and then dried over anhydrous sodium sulfate. After filtration, the filtrate was concentrated under reduced pressure to obtain 5.08 g (86.0%) of the title compound as a colorless oil.

$^1$H-NMR (400 MHz, CDCl$_3$) δ: 0.54–0.60 (1 H, m), 0.95–1.08 (2 H, m), 1.22 (3 H, t, J=7.33 Hz), 1.25–1.32 (1H, m), 1.35 (3 H, d, J=6.35 Hz), 1.99 (1 H, t, J=9.28 Hz), 2.42 (1 H, t, J=8.30 Hz), 2.63 (1 H, ddd, J=33.21, 11.72, 1.95 Hz), 2.99 (1 H, dm, J=28.32 Hz), 3.25–3.37 (2 H, m), 4.03–4.16 (2 H, m), 5.33 (1 H, dm, J=55.67 Hz), 7.21–7.36 (5 H, m).

Reference Example 7-4

1-Benzyloxycarbonyl-4-(S)-(1-ethoxycarbonylcyclopropyl)-3-(S)-fluoropyrrolidine

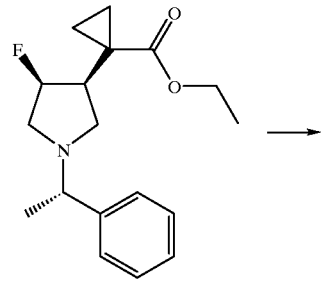

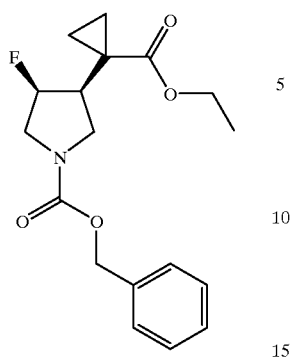

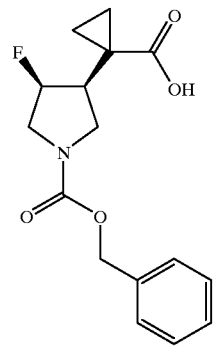

4-(S)-(1-Ethoxycarbonylcyclopropyl)-3-(S)-fluoro-1-[1-(S)-phenylethyl]pyrrolidine (5.08 g, 16.63 mmol) was dissolved in dry dichloromethane (50 ml), and benzyl chloroformate (3.56 ml, 25.0 mmol) was added dropwise to the thus prepared solution which was cooled in an ice bath. After 1 hour of heating of the reaction solution under reflux, dichloromethane was evaporated under reduced pressure. Thereafter, the resulting residue was subjected to flash silica gel chromatography and eluted with an eluant of n-hexane:ethyl acetate=3:1, to thereby obtain 4.67 g (83.7%) of the title compound as a colorless oil.

$^1$H-NMR (400 MHz, CDCl$_3$) δ: 0.71–0.78 (1 H, m), 1.11–1.23 (2 H, m), 1.24 (3 H, t, J=6.84 Hz), 1.29–1.37 (1 H, m), 2.93–3.00 (1 H, m), 3.10 (1 H, dm, J=34.67 Hz), 3.54–3.84 (2 H, m), 4.09–4.18 (2 H, m), 5.14 (2 H, s), 5.34 (1 H, ddm, J=53.71, 16.6 Hz), 7.29–7.38 (5 H, m).

1-Benzyloxycarbonyl-4-(S)-(1-ethoxycarbonylcyclopropyl)-3-(S)-fluoropyrrolidine (4.67 g, 13.92 mmol) was dissolved in ethanol (50 ml), and a 1 N sodium hydroxide aqueous solution (50 ml) was added dropwise to the resulting solution. The reaction solution was stirred at 40° C. for 1.5 hours and then ethanol was evaporated under reduced pressure. The resulting residue was mixed with water (50 ml) and washed with chloroform (100 ml), and the thus separated aqueous layer was acidified by adding dropwise 1 N hydrochloric acid and extracted with chloroform (200 ml×2) and then with diethyl ether (100 ml). The organic layers were combined and dried over anhydrous sodium sulfate. After filtration, the filtrate was concentrated under reduced pressure to obtain 3.94 g (92.1%) of the title compound as a colorless amorphous substance.

$^1$H-NMR (400 MHz, CDCl$_3$) δ: 0.79–0.89 (1 H, m), 1.18–1.35 (2 H, m), 1.37–1.47 (1 H, m), 2.90–3.18 (2 H, m), 3.50–3.84 (3 H, m), 5.13 (2 H, s), 5.31 (1 H, ddm, J=53.22, 15.13 Hz), 7.26–7.42 (5 H, m).

Reference Example 7-5

1-[1-Benzyloxycarbonyl-4-(S)-fluoro-3-(S)-pyrrolidinyl]cyclopropanecarboxylic acid

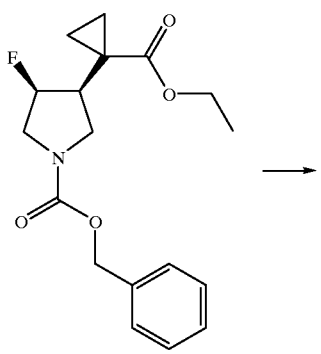

Reference Example 7-6

1-Benzyloxycarbonyl-4-(R)-(1-tert-butoxycarbonylaminocyclopropyl)-3-(S)-fluoropyrrolidine

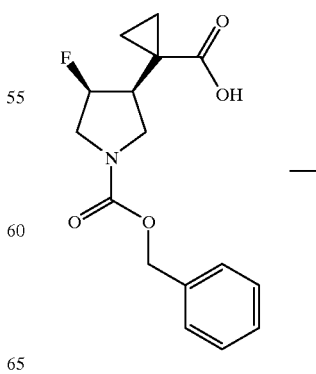

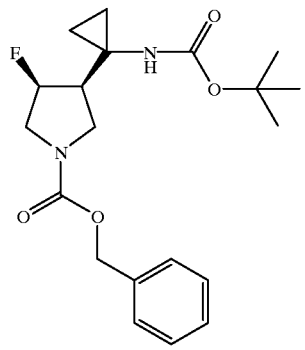

1-[1-Benzyloxycarbonyl-4-(S)-fluoro-3-(S)-pyrrolidinyl] cyclopropanecarboxylic acid (3.22 g, 10.48 mmol) was dissolved in anhydrous acetonitrile (80 ml), and the solution was mixed with N-N'-carbonyldiimidazole (2.55 g, 15.73 mmol) and stirred at room temperature for 30 minutes. Ammonia was bubbled into the reaction solution for 30 minutes at the same temperature. The reaction solution was concentrated under reduced pressure. The thus obtained residue was mixed with water (80 ml) and extracted with chloroform (80 ml×2), and the organic layers were combined and dried over anhydrous sodium sulfate. After filtration, the filtrate was concentrated under reduced pressure. The resulting residue was dissolved in tert-butyl alcohol (100 ml), and the solution was mixed with lead tetraacetate (7.93 g, 15.70 mmol) and heated under reflux for 30 minutes. The reaction solution was cooled, mixed with diethyl ether (50 ml) and sodium bicarbonate (10 g) and then stirred at room temperature for 10 minutes. After filtration, the filtrate was concentrated under reduced pressure. The thus obtained residue was mixed with ethyl acetate (150 ml), washed with a saturated sodium bicarbonate aqueous solution and then dried over anhydrous sodium sulfate. After filtration, the filtrate was concentrated under reduced pressure, and the resulting residue was subjected to flash silica gel chromatography and eluted with an eluant of n-hexane:ethyl acetate=3:2, to thereby obtain 3.216 g (81.2%) of the title compound as a colorless oil.

$^1$H-NMR (400 MHz, CDCl$_3$) δ: 0.65–0.74 (1 H, m), 0.77–0.84 (1 H, m), 0.85–1.00 (2 H, m), 1.42 (9 H, s), 2.21 (1 H, ddm, J=80.57, 36.14 Hz), 3.08–3.24 (2 H, m), 3.48–3.84 (3 H, m), 5.02 (1 H, brs), 5.13 (2 H, s), 5.15 (1 H, brd, J=53.72 Hz), 7.28–7.38 (5 H, m).

Example 9

5-Amino-7-[4-(R)-(1-aminocyclopropyl)-3-(S)-fluoro-1-pyrrolidinyl]-6-fluoro-1-[2-(S)-fluoro-1-(R)-cyproyyl]-1,4-dihydro-8-methyl-4-oxoquinoline-3-carboxylic acid hydrochloride

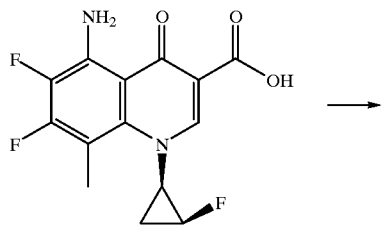  →

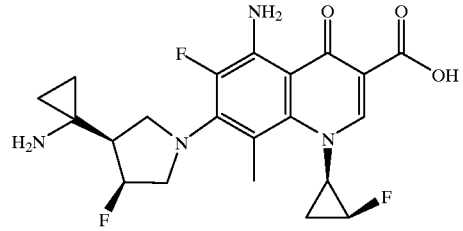

1-Benzyloxycarbonyl-4-(R)-(1-tert-butoxycarbonylaminocyclopropyl)-3-(S)-fluoropyrrolidine (1.43 g, 3.78 mmol) was dissolved in ethanol (60 ml), and the solution was mixed with a 5% palladium-carbon catalyst (water content, 55.6%; 1.5 g) and stirred for 3 hours under a hydrogen atmosphere. The catalyst was removed by celite filtration (methanol washing), and the filtrate was concentrated under reduced pressure. The thus obtained residue was dissolved in dimethyl sulfoxide (12 ml), and the solution was mixed with 5-amino-6,7-difluoro-1-[2-(S)-fluoro-1-(R)-cyclopropyl]-1,4-dihydro-8-methyl-4-oxoquinoline-3-carboxylic acid (1.18 g, 3.78 mmol) and triethylamine (3 ml) and stirred for 3 days at 130° C. under a nitrogen atmosphere. After cooling, dimethyl sulfoxide was evaporated under reduced pressure, the thus obtained residue was dissolved in chloroform (80 ml) and washed with a 10% citric acid aqueous solution (80 ml) and saturated brine (100 ml) in that order and then the organic layer was dried over anhydrous sodium sulfate. After filtration, the filtrate was concentrated under reduced pressure. The thus obtained residue was subjected to flash silica gel chromatography and eluted with a mixture of chloroform:methanol=9:1, and the eluate was concentrated under reduced pressure. To the thus obtained residue, which was cooled in an ice bath, was added dropwise concentrated hydrochloric acid (10 ml), followed by 50 minutes of stirring at room temperature. After adding 1 N hydrochloric acid (30 ml) to the reaction solution, the aqueous solution was washed with chloroform (50 ml×2) and adjusted to pH 12.0 with a sodium hydroxide aqueous solution. The aqueous solution was washed with chloroform (100 ml), adjusted to pH 7.4 with 1 N hydrochloric acid and then extracted with chloroform (150 ml×3). The organic layers were combined, dried over anhydrous sodium sulfate and then filtered, and the filtrate was concentrated under reduced pressure. To the thus obtained residue which was cooled in an ice bath was added dropwise 1 N hydrochloric acid (2.0 ml), followed by 5 minutes of stirring at the same temperature and subsequent concentration of the reaction solution under reduced pressure (ethanol azeotropic treatment was conducted three times). Thereafter, the resulting residue was purified by recrystallization from ethanol and then dried under reduced pressure to obtain 230 mg (12.1%) of the title compound as a yellow powder.

$^1$H-NMR (400 MHz, 0.1 N NaOD) δ: 0.55–0.71 (4 H, m), 1.10–1.21 (1 H, m), 1.46–1.58 (1 H, m), 2.30 (3 H, s), 2.21–2.35 (1 H, m), 3.32 (1 H, t, J=8.79 Hz), 3.49 (1 H, dd, J=25.88, 12.21 Hz), 3.85–3.97 (2 H, m), 4.11 (1 H, ddm, J=40.77, 12.45 Hz), 4.97 (1 H, dm, J=70.31 Hz), 5.49 (1 H, brd, J=55.18 Hz), 8.27 (1 H, d, J=3.42 Hz).

Elemental analysis data; for $C_{21}H_{23}F_3N_4O_3 \cdot HCl \cdot 1.25H_2O$: calcd.; C, 50.40; H, 5.33; N, 10.87 found; C, 50.45; H, 5.44; N, 11.21

Example 10

5-Amino-7-[4-(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methoxy-4-oxoquinoline-3-carboxylic acid

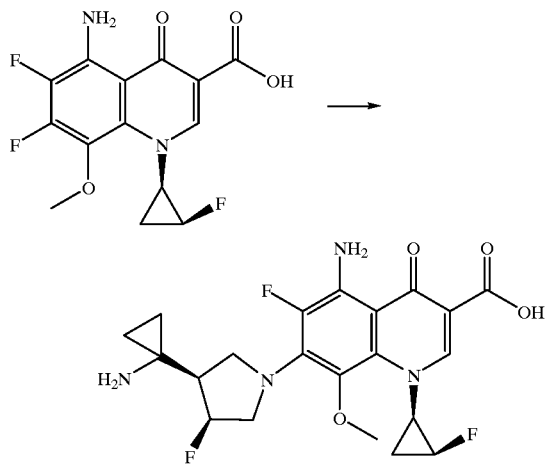

1-Benzyloxycarbonyl-4-(R)-(1-tert-butoxycarbonylaminocyclopropyl)-3-(S)-fluoropyrrolidine (400 mg, 1.06 mmol) was dissolved in ethanol (20 ml), and the solution was mixed with a 5% palladium-carbon catalyst (water content, 55.6%; 500 mg) and stirred for 18 hours under a hydrogen atmosphere. The catalyst was removed by celite filtration (methanol washing), and the filtrate was concentrated under reduced pressure. The thus obtained residue was dissolved in dimethyl sulfoxide (8 ml), and the solution was mixed with 5-amino-6,7-difluoro-1-[2-(S)-fluoro-1-(R)-cyclopropyl]-1,4-dihydro-8-methoxy-4-oxoquinoline-3-carboxylic acid (289 mg, 0.88 mmol) and triethylamine (2 ml) and stirred for 26 hours at 100° C. in a nitrogen atmosphere. After cooling, dimethyl sulfoxide was evaporated under reduced pressure, the thus obtained residue was dissolved in chloroform (80 ml) and washed-with a 10% citric acid aqueous solution (80 ml) and then the organic layer was dried over anhydrous sodium sulfate. After filtration, the filtrate was concentrated under reduced pressure. The thus obtained residue was subjected to flash silica gel chromatography and eluted with a mixture of chloroform:methanol=9:1, and the eluate was concentrated under reduced pressure. To the thus obtained residue, which was cooled in an ice bath, was added dropwise concentrated hydrochloric acid (5 ml), followed by 20 minutes of stirring at room temperature. After adding 1 N hydrochloric acid (30 ml) to the reaction solution, the aqueous solution was washed with chloroform (50 ml×2) and adjusted to pH 12.0 with a sodium hydroxide aqueous solution. The aqueous solution was washed with chloroform (100 ml×2), adjusted to pH 7.4 with 1 N hydrochloric acid and then extracted with chloroform (200 ml×3). The organic layers were combined, dried over anhydrous sodium sulfate and then filtered, and the filtrate was concentrated under reduced pressure. Thereafter, the resulting residue was purified by recrystallization from ethanol and then dried under reduced pressure to obtain 170 mg (42.6%) of the title compound as a yellow powder.

$^1$H-NMR (400 MHz, 0.1 N NaOD) δ: 0.57–0.74 (4 H, m), 1.12– 1.27 (1 H, m), 1.36–1.48 (1 H, m), 2.24 (1 H, dm, J=37.60 Hz), 3.46 (3 H, s), 3.53 (1 H, t, J=8.79 Hz), 3.69 (1 H, dd, J=25.40, 12.21 Hz), 3.86–3.94 (2 H, m), 4.10 (1 H, ddm, J=42.48, 12.70 Hz), 5.00 (1 H, dm, J=63.97 Hz), 5.49 (1 H, brd, J=54.69 Hz), 8.19 (1 H, d, J=3.91 Hz).

Elemental analysis data; for $C_{21}H_{23}F_3N_4O_4$: calcd.; C, 55.75; H, 5.12; N, 12.38 found; C, 55.78; H, 5.20; N, 12.28

Example 11

10-[4-(R)-(1-Aminocyclopropyl)-3-(S)-fluoro-1-pyrrolidinyl]-9-fluoro-2,3-dihydro-3-(S)-methyl-7-oxo-7H-pyrido[1.2.3-de][1.4]benzoxazine-6-carboxylic acid

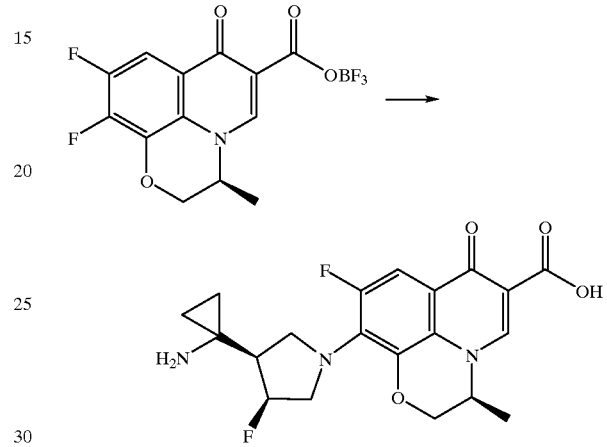

1-Benzyloxycarbonyl-4-(R)-(1-tert-butoxycarbonylaminocyclopropyl)-3-(S)-fluoropyrrolidine (913 mg, 2.41 mmol) was dissolved in methanol (50 ml), and the solution was mixed with a 5% palladium-carbon catalyst (water content, 55.6%; 1.0 g) and stirred for 3 hours under a hydrogen atmosphere. The catalyst was removed by celite filtration (methanol washing), and the filtrate was concentrated under reduced pressure. The thus obtained residue was dissolved in dimethyl sulfoxide (15 ml), and the solution was mixed with 9,10-difluoro-2,3-dihydro-3-(S)-methyl-7-oxo-7H-pyrido[1.2.3-de][1.4]benzoxazine-6-carboxylic acid-BF$_2$ chelate (661 mg, 2.01 mmol) and triethylamine (336 μl, 2.41 mmol) and stirred for 3 days at room temperature. The reaction solution was concentrated under reduced pressure, the resulting residue was mixed with water and then the thus precipitated yellow crystals were collected by filtration and washed with water. The thus obtained crystals were suspended in a mixture of methanol:water=1:1 (200 ml), and the suspension was mixed with triethylamine (4 ml) and heated under reflux for 4 hours. After cooling, the reaction solution was concentrated under reduced pressure, the thus obtained residue was dissolved in chloroform (200 ml) and washed with 10% citric acid aqueous solution (200 ml) and then the organic layer was dried over anhydrous sodium sulfate. After filtration, the filtrate was concentrated under reduced pressure. To the thus obtained residue, which was cooled in an ice bath, was added dropwise concentrated hydrochloric acid (10 ml), followed by 10 minutes of stirring at room temperature. After adding 1 N hydrochloric acid (30 ml) to the reaction solution, the aqueous solution was washed with chloroform (50 ml×2) and adjusted to pH 12.0 with a sodium hydroxide aqueous solution and then to pH 7.4 with 1 N hydrochloric acid, followed by extraction with chloroform (500 ml×3). The organic layers were combined, dried over anhydrous sodium sulfate and then filtered, and the filtrate was concentrated under reduced pressure. Thereafter, the resulting residue was purified by recrystallization from ethanol and then dried under reduced pressure to obtain 459 mg (56.4%) of the title compound as light yellow crystals.

$^1$H-NMR (400 MHz, 0.1 N NaOD) δ: 0.55–0.75 (4 H, m), 1.52 (3 H, d, J=6.84 Hz), 2.25 (1 H, dm, J=36.62 Hz), 3.49 (1 H, t, J=8.79 Hz), 3.70 (1 H, dd, J=26.37, 11.72 Hz), 3.88 (1 H, t, J=8.79 Hz), 4.10 (1 H, dd, J=40.53, 12.70 Hz), 4.30 (1 H, d, J=9.27 Hz), 4.50 (1 H, d, J=9.28 Hz), 4.55–4.65 (1 H, m), 5.47 (1 H, dt, J=55.17, 3.42 Hz), 7.53 (1 H, d, J=14.16 Hz), 8.33 (1 H, s).

Example 12

7-[4-(R)-(1-Aminocyclopropyl)-3-(S)-fluoro-1-pyrrolidinyl]-6-fluoro-1-[2-(S)-fluoro-1-(R)-cyclopropyl]-1,4-dihydro-8-methoxy-4-oxoquinoline-3-carboxylic acid

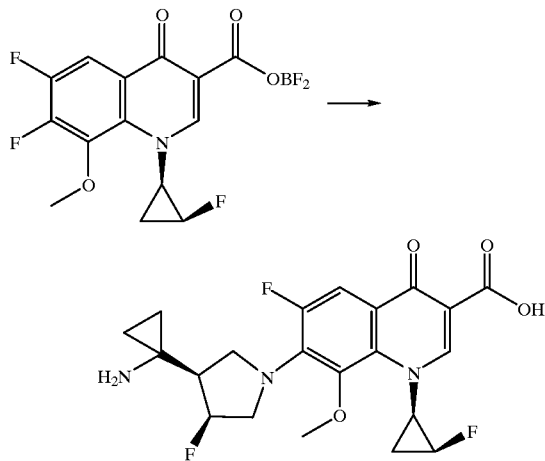

1-Benzyloxycarbonyl-4-(R)-(1-tert-butoxycarbonylaminocyclopropyl)-3-(S)-fluoropyrrolidine (1.07 g, 2.84 mmol) was dissolved in ethanol (50 ml), and the solution was mixed with a 10% palladium-carbon catalyst (water content, 50.5%; 1.0 g) and stirred for 16 hours under a hydrogen atmosphere. The catalyst was removed by celite filtration (methanol washing), and the filtrate was concentrated under reduced pressure. The thus obtained residue was dissolved in dimethyl sulfoxide (10 ml), and the solution was mixed with 6,7-difluoro-1-[2-(S)-fluoro-1-(R)-cyclopropyl]-1,4-dihydro-8-methoxy-4-oxoquinoline-3-carboxylic acid-BF$_2$ chelate (853 mg, 2.36 mmol) and triethylamine (395 µl, 2.83 mmol) and stirred for 24 hours at room temperature. The reaction solution was concentrated under reduced pressure, the resulting residue was mixed with water and then the thus precipitated solid matter was collected by filtration and washed with water. The thus obtained solid matter was suspended in a mixture of methanol:water=9:1 (100 ml), and the suspension was mixed with triethylamine (5 ml) and heated under reflux for 3 hours. After cooling, the reaction solution was concentrated under reduced pressure, the thus obtained residue was dissolved in chloroform (300 ml) and washed with 10% citric acid aqueous solution (300 ml) and then the organic layer was dried over anhydrous sodium sulfate. After filtration, the filtrate was concentrated under reduced pressure. To the thus obtained residue, which was cooled in an ice bath, was added dropwise concentrated hydrochloric acid (10 ml), followed by 5 minutes of stirring at room temperature. After adding 1 N hydrochloric acid (30 ml) to the reaction solution, the aqueous solution was washed with chloroform (50 ml×2) and adjusted to pH 12.0 with a sodium hydroxide aqueous solution. The aqueous solution was washed with chloroform (50 ml×2), adjusted to pH 7.4 with 1 N hydrochloric acid and then extracted with chloroform (500 ml ×3). The organic layers were combined, dried over anhydrous sodium sulfate and then filtered, and the filtrate was concentrated under reduced pressure. Thereafter, the resulting residue was purified by recrystallization from ethanol and then dried under reduced pressure to obtain 715 mg (69.3%) of the title compound as light yellow crystals.

Melting point: 218.5–219.8° C. (decomposition)

$^1$H-NMR (400 MHz, 0.1 N NaOD) δ: 0.57–0.74 (4 H, m), 1.32–1.45 (1 H, m), 1.48–1.60 (1H, m), 2.20–2.38 (1 H, m), 3.53–3.58 (1 H, m), 3.58 (3 H, s), 3.72 (1 H, dd, J=25.88, 13.19 Hz), 3.86–3.93 (1 H, m), 4.00–4.18 (2 H, m), 5.05 (1 H, dm, J=63.96 Hz), 5.51 (1 H, brd, J=54.68 Hz), 7.68 (1 H, d, J=14.16 Hz), 8.19 (1 H, d, J=3.91 Hz).

Elemental analysis data; for C$_{21}$H$_{22}$F$_3$N$_3$O$_4$: calcd.; C, 57.66; H, 5.07; N, 9.61 found; C, 57.96; H, 5.13; N, 9.48

Reference Example 8-1

Ethyl 1-acetylcyclobutanecarboxylate

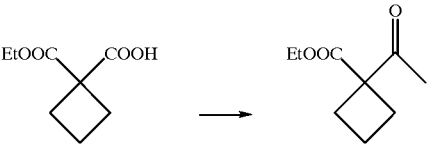

Ethyl hydrogen 1,1-cyclobutanecarboxylate (64.43 g, 374 mmol) was dissolved in methylene chloride (500 ml) to which, while cooling in an ice bath, were subsequently added oxalyl chloride (65.29 ml, 748 mmol) and a catalytic amount of N,N-dimethylformamide in that order. After 1.5 hours of stirring at room temperature, the solvent was evaporated and the resulting residue was twice subjected to azeotropic treatment with toluene, to thereby prepare an acid chloride.

Separately from this, under a stream of nitrogen, copper(I) iodide (85.52 g, 449 mmol) was suspended in 1 liter of tetrahydrofuran to which was then added dropwise a 1.4 M methyl lithium diethyl ether solution (294 ml) at −20° C., followed by 1 hour of stirring at the same temperature. To this was added dropwise a solution (300 ml) of the aforementioned acid chloride at the same temperature, followed by 1.5 hours of stirring. After completing the reaction, the reaction solution was warmed to room temperature and mixed with a 10% citric acid aqueous solution (500 ml). Tetrahydrofuran was evaporated, and the resulting residue was mixed with ethyl acetate (1 liter), washed, after removing insoluble material by filtration, with a 5% sodium thiosulfate aqueous solution (300 ml) and saturated brine (300 ml) in that order and then dried over anhydrous sodium sulfate. After evaporating the solvent, the resulting residue was subjected to silica gel column chromatography and eluted with an eluant of n-hexane:ethyl acetate=4:1, to thereby obtain 56.70 g (89%) of the title compound in an oily form.

$^1$H-NMR (400 MHz, CDCl$_3$) δ: 1.27 (3 H, t, J=7.33 Hz), 1.82–2.01 (2 H, m), 2.12 (3 H, s), 2.45–2.55 (4 H, m), 4.20–4.24 (2 H, m).

Reference Example 8-2

Ethyl 1-ethoxycarbonyl-β-hydroxy-β-methyl-cyclobutylpropanoate

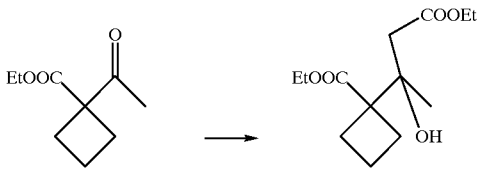

Ethyl 1-acetylcyclobutanecarboxylate (13.79 g, 81 mmol) was dissolved in tetrahydrofuran (50 ml), and the solution was mixed with zinc powder (10.59 g) and a catalytic amount of iodine. While heating under reflux, a tetrahydrofuran solution (100 ml) of ethyl bromoacetate (13.48 ml, 121 mmol) was added dropwise thereto. The reaction solution was heated under reflux for an additional 1 hour, cooled and then mixed with 1 N hydrochloric acid (100 ml). After evaporating the solvent, the resulting residue was mixed with ethyl acetate (500 ml), washed, after removing insoluble material by filtration, with saturated brine (300 ml) and then dried over anhydrous sodium sulfate. By evaporating the solvent, the title compound was obtained quantitatively in an oily form.

$^1$H-NMR (400 MHz, CDCl$_3$) δ: 1.24–1.32 (9 H, m), 1.73–1.87 (2 H, m), 2.21–2.34 (2 H, m), 2.41–2.57 (5 H, m), 4.16–4.21 (4 H, m).

Reference Example 8-3

(E)-Ethyl 3-(1-ethoxycarbonylcyclobutyl)-2-butenoate

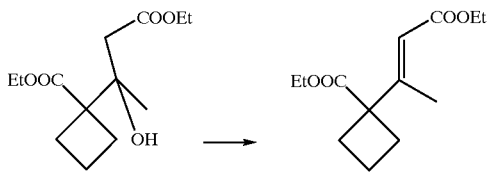

Ethyl 1-ethoxycarbonyl-β-hydroxy-β-methyl-cyclobutylpropanoate (22.27 g, 86 mmol) was dissolved in pyridine (42 ml), and thionyl chloride (8.18 ml, 112 mmol) was added dropwise to the thus prepared solution which was cooled at −10° C. After completing the reaction, the reaction solution was poured into ice water (250 ml) and extracted with ethyl acetate (100 ml×3). The organic layers were combined, washed with 1 N hydrochloric acid (100 ml) and saturated brine (100 ml) in that order and then dried over anhydrous sodium sulfate. The solvent was evaporated and the thus obtained residue was dissolved in methylene chloride (250 ml). At 0° C., to this was added dropwise 1,8-diazabicyclo [5,4,0]-7-undecene (12.89 ml), followed by 18 hours of stirring at room temperature. After completing the reaction, the solvent was evaporated and the thus obtained residue was mixed with ice water (100 ml) and extracted with ethyl acetate (200 ml×3). The organic layers were combined, washed with 1 N hydrochloric acid (100 ml) and saturated brine (100 ml) and then dried over anhydrous sodium sulfate. After evaporating the solvent, the resulting residue was subjected to silica gel column chromatography and eluted with an eluant of n-hexane:ethyl acetate=4:1, to thereby obtain 16.91 g (82%) of the title compound in an oily form.

$^1$H-NMR (400 MHz, CDCl$_3$) δ: 1.24 (3 H, t, J=6.83 Hz), 1.29 (3 H, t, J=7.32 Hz), 1.74–1.80 (2 H, m), 1.94–2.04 (1 H, m), 2.07 (3 H, d, J=1.47 Hz), 2.12–2.30 (2 H, m), 2.12–2.30 (2 H, m), 2.50–2.57 (2 H, m), 4.13–4.20 (4 H, m).

Reference Example 8-4

4-(1-Ethoxycarbonylcyclobutyl)-1-[(S)-1-phenylethyl]-3-pyrrolin-2-one

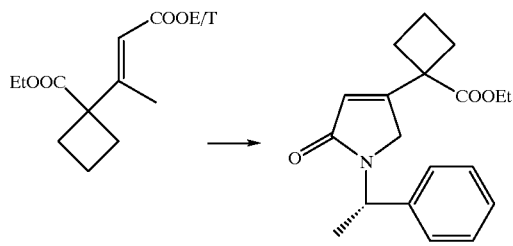

(E)-Ethyl 3-(1-ethoxycarbonylcyclobutyl)-2-butenoate (16.91 g, 70 mmol) was dissolved in chloroform (180 ml), and the solution was mixed with N-bromosuccinimide (12.53 g, 70 mmol) and a catalytic amount of azobisisobutyronitrile and heated under reflux for 18 hours. After completing the reaction, the solvent was evaporated, the thus obtained residue was mixed with carbon tetrachloride (100 ml), insoluble material was removed by filtration and then the resulting filtrate was concentrated. The thus obtained residue was dissolved in ethanol (100 ml) and mixed with sodium bicarbonate (11.82 g, 140 mmol). At room temperature, thereto was added dropwise (S)-phenylethylamine (9.87 ml, 77 mmol). After completing the dropwise addition, the mixture was heated under reflux for 3 hours. After completing the reaction, the solvent was evaporated, and the thus obtained residue was mixed with methylene chloride (300 ml). After removing insoluble material by filtration, the solvent was evaporated and the resulting residue was subjected to silica gel column chromatography and eluted with an eluant of n-hexane: ethyl acetate=1:1, to thereby obtain 19.57 g (43%) of the title compound in an oily form.

$^1$H-NMR (400 MHz, CDCl$_3$) δ: 1.17 (3 H, t, J=7.33 Hz), 1.74–1.80 (2 H, m), 1.59 (3 H, d, J=6.84 Hz), 1.84–2.01 (2 H, m), 2.15–2.28 (2 H, m), 2.60–2.69 (2 H, m), 3.56 (2 H, d, J=9.04 Hz), 3.88 (2 H, d, J=9.04 Hz), 4.13 (2 H, q, J=7.32 Hz), 5.50–5.59 (1 H, m), 6.03 (1 H, s), 7.26–7.35 (5 H, m).

Reference Example 8-5

4-(1-Ethoxycarbonylcyclobutyl)-1-[(S)-1-phenylethyl]-2-pyrrolidone

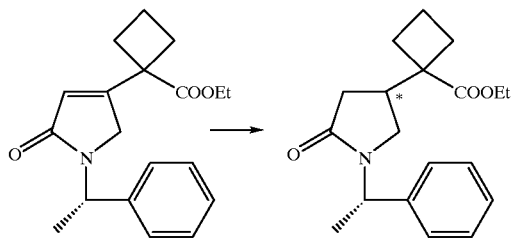

4-(1-Ethoxycarbonylcyclobutyl)-1-[(S)-1-phenylethyl]-3-pyrrolin-2-one (9.57 g, 31 mmol) was dissolved in ethanol (150 ml), and the solution was mixed with platinum oxide (230 mg) and stirred for 18 hours in a hydrogen atmosphere. After completing the reaction, the reaction solution was filtered and concentrated, and the resulting residue was applied three times to a silica gel chromatography column and eluted with an eluant of n-hexane:ethyl acetate=1:1, to thereby obtain optical isomer A (2.3 g, 24%) and optical isomer B (7.1 g, 74%) of the title compound each in an oily form.

Optical Isomer A

¹H-NMR (400 MHz, CDCl₃) δ: 1.26 (3 H, t, J=6.83 Hz), 1.49 (2 H, d, J=7.32 Hz), 1.83–1.95 (4 H, m), 2.38–2.54 (4 H, m), 2.66–2.74 (1 H, m), 3.01 (1 H, t, J=8.30 Hz), 3.14 (1 H, d, J=5.86, 9.77 Hz), 4.09–4.18 (2 H, m), 5.48 (1 H, dd, J=7.32, 14.16 Hz), 7.27–7.35 (5 H, m).

Optical Isomer B

¹H-NMR (400 MHz, CDCl₃) δ: 1.17 (3 H, t, J=7.32 Hz), 1.52 (2 H, d, J=7.33 Hz), 1.68–1.92 (4 H, m), 2.23–2.43 (3 H, m), 2.50–2.57 (1 H, m), 2.73–2.86 (2 H, m), 3.37 (1 H, t, J=8.30 Hz), 4.05 (2 H, q, J=7.32 Hz), 5.50 (1 H, dd, J=7.32, 14.16 Hz), 7.24–7.35 (5 H, m).

Reference Example 8-6

Trans 4-(1-ethoxycarbonylcyclobutyl)-3-fluoro-1-[1-(S)-phenylethyl]-2-pyrrolidone (optical isomer B)

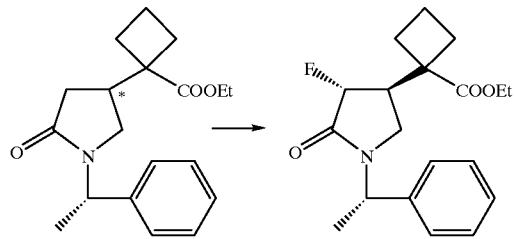

Under a nitrogen atmosphere, diisopropylamine (2.55 ml, 18.2 mmol) was dissolved in anhydrous tetrahydrofuran (120 ml) to which, after cooling to −78° C., was subsequently added dropwise an n-hexane solution of 1.63 M an n-butyl lithium (11.2 ml, 18.2 mmol) over a period of 10 minutes. After 15 minutes of stirring at 0° C., the reaction solution was cooled to −78° C. and 4-(1-ethoxycarbonylcyclopropyl)-1-[1-(S)-phenylethyl]-2-pyrrolidone (optical isomer B; 4.42 g, 14.01 mmol) dissolved in anhydrous tetrahydrofuran (30 ml) was added dropwise thereto over a period of 15 minutes. The reaction solution was stirred at −78° C. for 1 hour, and N-fluorobenzene disulfonimide (7.07 g, 22.42 mmol) dissolved in anhydrous tetrahydrofuran (25 ml) was added dropwise thereto at the same temperature over a period of 5 minutes. The reaction solution was stirred at −78° C. for 30 minutes and then at room temperature for 20 minutes. Saturated ammonium chloride aqueous solution (200 ml) was added to the reaction solution which was cooled in an ice bath, tetrahydrofuran was evaporated and then the aqueous layer was extracted with ethyl acetate (200 ml×2). The organic layers were combined, washed with water (200 ml×3) and then dried over anhydrous sodium sulfate. After filtration, the filtrate was concentrated under reduced pressure, and the resulting residue was subjected to silica gel column chromatography and eluted with an eluant of n-hexane:ethyl acetate=1:1, to thereby obtain 3.88 g (83%) of the title compound in an oily form.

¹H-NMR (400 MHz, CDCl₃) δ: 1.14 (3 H, t, J=6.83 Hz), 1.57 (2 H, d, J=6.83 Hz), 1.88–2.08 (4 H, m), 2.33–2.58 (3 H, m), 2.81–2.92 (1 H, m), 3.42 (1 H, t, J=9.77 Hz), 3.93–4.07 (2 H, m), 5.18 (1 H, dd, J=6.83, 53.22 Hz), 5.51 (1 H, dd, J=7.32, 14.16 Hz), 7.25–7.34 (5 H, m).

Reference Example 8-7

Cis 4-(1-ethoxycarbonylcyclobutyl)-3-fluoro-1-[1-(S)-phenylethyl]-2-pyrrolidone (optical isomer B)

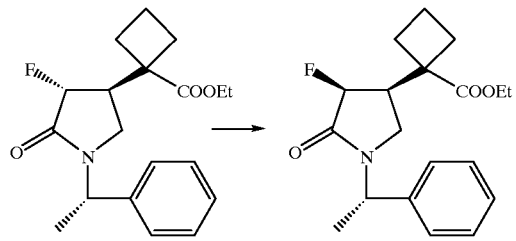

Under a nitrogen atmosphere, diisopropylamine (2.97 ml, 21.19 mmol) was dissolved in anhydrous tetrahydrofuran (30 ml) to which, after cooling to −78° C., was subsequently added dropwise an n-hexane solution of 1.63 M n-butyl lithium (10.8 ml, 17.60 mmol) over a period of 5 minutes. After 15 minutes of stirring at 0° C., the reaction solution was cooled to −78° C. and trans 4-(1-ethoxycarbonylcyclopropyl)-3-fluoro-1-[1-(S)-phenylethyl]-2-pyrrolidone (optical isomer B; 4.71 g, 14.13 mmol) dissolved in anhydrous tetrahydrofuran (30 ml) was added dropwise thereto over a period of 5 minutes. The reaction solution was stirred at −78° C. for 3 minutes, and 2,6-di-tert-butylphenol (4.37 g, 21.18 mmol) dissolved in anhydrous tetrahydrofuran (40 ml) was added dropwise thereto over a period of 5 minutes. The reaction solution was stirred at −78° C. for 10 minutes, mixed with saturated ammonium chloride aqueous solution (200 ml) and then warmed to room temperature. The organic layer was separated and then the aqueous layer was extracted with chloroform (100 ml×2). The organic layers were combined, washed with water (100 ml×2) and then dried over anhydrous sodium sulfate. After filtration, the filtrate was concentrated under reduced pressure, and the resulting residue was subjected to silica gel column chromatography and eluted with an eluant of n-hexane:ethyl acetate=2:1 to recover 1.96 g (42%) of the starting material and then with n-hexane:ethyl acetate=3:2 to obtain 1.79 g (38%) of the title compound in an oily form.

¹H-NMR (400 MHz, CDCl₃) δ: 1.22 (3 H, t, J=6.83 Hz), 1.56–1.58 (3 H, d, J=6.83 Hz), 1.84–2.42 (6 H, m), 2.83–2.97 (1 H, m), 3.15–3.24 (1 H, m), 3.36–3.43 (1 H, m), 4.11–4.17 (2 H, m), 5.07 (1 H, dd, J=6.83, 52.24 Hz), 5.56 (1 H, q, J=7.33 Hz), 7.26–7.36 (5 H, m).

Reference Example 8-8

Cis 4-(1-carboxycyclobutyl)-3-fluoro-1-[1-(S)-phenylethyl]-2-pyrrolidone (optical isomer B)

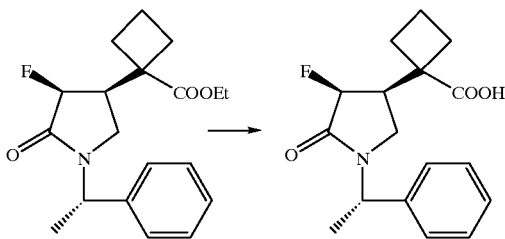

Cis 4-(1-ethoxycarbonylcyclobutyl)-3-fluoro-1-[1-(S)-phenylethyl]-2-pyrrolidone (optical isomer B; 1.79 g, 5.37 mmol) was dissolved in methanol (10 ml) to which was subsequently added dropwise a 1 N sodium hydroxide aqueous solution (10 ml). The reaction solution was stirred at 40° C. for 18 hours and then methanol was evaporated under reduced pressure. The thus obtained residue was mixed with water (50 ml) and washed with chloroform (100 ml). The thus separated aqueous layer was acidified by dropwise addition of 1 N hydrochloric acid and extracted with chloroform (100 ml×2). The organic layers were combined and dried over anhydrous sodium sulfate. After filtration, the filtrate was concentrated under reduced pressure to obtain the title compound quantitatively as a crude product.

Reference Example 8-9

Cis 4-(1-tert-butoxycarbonylaminocyclobutyl)-3-fluoro-1-[1-(S)-phenylethyl]-2-pyrrolidone (optical isomer B)

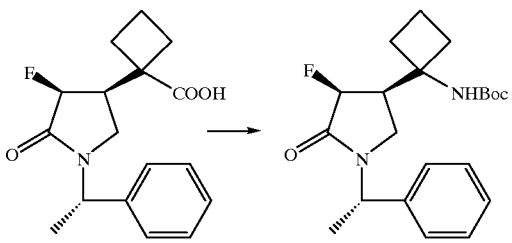

Cis 4-(1-carboxycyclobutyl)-3-fluoro-1-[1-(S)-phenylethyl]-2-pyrrolidone (optical isomer B; 1.92 g, 6.29 mmol) was dissolved in anhydrous acetonitrile (30 ml), and the solution was mixed with N,N'-carbonyl diimidazole (1.33 g, 8.20 mmol) and stirred at 60° C. for 1 hour. At room temperature and for 10 minutes, ammonia was bubbled into the reaction solution which was subsequently concentrated under reduced pressure. The thus obtained residue was mixed with water (100 ml) and extracted with chloroform (100 ml×2), and the organic layers were combined and dried over anhydrous sodium sulfate. After filtration, the filtrate was concentrated under reduced pressure, and the resulting residue was dissolved in tert-butyl alcohol (50 ml), mixed with lead tetraacetate (6.32 g, 14.25 mmol) and then heated under reflux for 1 hour. After cooling, the reaction solution was mixed with diethyl ether (50 ml) and sodium bicarbonate (6 g), and the mixture was stirred at room temperature for 10 minutes. After filtration, the filtrate was concentrated under reduced pressure. The thus obtained residue was mixed with 100 ml of ethyl acetate, washed with saturated sodium bicarbonate and then dried over anhydrous sodium sulfate. Thereafter, this was filtered and the resulting filtrate was concentrated under reduced pressure to obtain 1.74 g (65%) of the title compound in an oily form.

$^1$H-NMR (400 MHz, CDCl$_3$) δ: 1.40 (9 H, s), 1.92–2.21 (6 H, m), 3.04–3.12 (1 H, m), 3.31–3.38 (1 H, m), 4.87 (1 H, brs), 5.01 (1 H, dd, J=5.86, 52.73 Hz), 5.52 (1 H, dd, J=7.32, 14.16 Hz), 7.30–7.38 (5 H, m).

Reference Example 8-10

Cis 1-[1-(S)-phenylethyl]-4-(1-tert-butoxycarbonylaminocyclobutyl)-3-fluoropyrrolidone (optical isomer B)

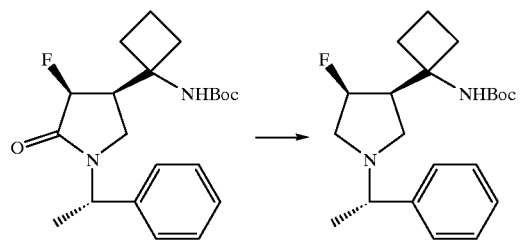

Cis 4-(1-tert-butoxycarbonylaminocyclobutyl)-3-fluoro-1-[1-(S)-phenylethyl]-2-pyrrolidone (optical isomer B; 1.74 g, 4.62 mmol) was dissolved in tetrahydrofuran (30 ml), and the solution was mixed with a 1 M boran-tetrahydrofuran complex (13.86 ml) at 0° C. and then stirred at room temperature for 2 days. After completing the reaction, the solvent was evaporated and the thus obtained residue was mixed with water (50 ml) and extracted with chloroform (100 ml×2). The organic layers were combined and dried over anhydrous sodium sulfate. After filtration, the filtrate was concentrated under reduced pressure, and the resulting residue was dissolved in 80% aqueous ethanol (40 ml), mixed with triethylamine (10 ml) and then heated under reflux for 2 hours. Thereafter, the solvent was evaporated and the resulting residue was subjected to silica gel column chromatography and eluted with an eluant of n-hexane:ethyl acetate=2:1, to thereby obtain 1.13 g (67%) of the title compound in an oily form.

$^1$H-NMR (400 MHz, CDCl$_3$) δ: 1.37 (3 H, d, J=6.35 Hz), 1.44 (9 H, s), 1.65–2.58 (7 H, m) 2.70–2.92 (4 H, m), 3.27–3.32 (1 H, m), 5.14 (1 H, brd), 5.53 (1 H, brs), 7.22–7.33 (5 H, m).

Example 13

5-Amino-7-[cis 4-(1-aminocyclobutyl)-3-fluoro-1-pyrrolidinyl]-6-fluoro-1-[2-(S)-fluoro-1-(R)-cyclopropyl]-1,4-dihydro-8-methyl-4-oxoquinoline-3-carboxylic acid (optical isomer B)

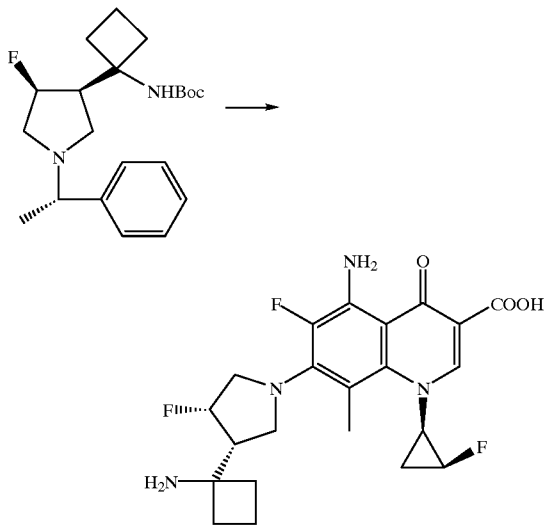

Cis 1-[1-(S)-phenylethyl]-4-(1-tert-butoxycarbonylaminocyclobutyl)-3-fluoropyrrolidine (optical isomer B; 1.13 g, 3.12 mmol) was dissolved in ethanol (20 ml), and the solution was mixed with a 10% palladium-carbon catalyst (water content, 55.6%; 1.0 g) and stirred at 50° C. for 18 hours under a hydrogen atmosphere. The catalyst was removed by celite filtration (methanol washing), and the filtrate was concentrated under reduced pressure. The thus obtained residue was dissolved in dimethyl sulfoxide (10 ml), and the solution was mixed with 5-amino-6,7-difluoro-1-[2-(S)-fluoro- 1-(R)-cyclopropyl]-1,4-dihydro-8-methyl-4-oxoquinoline-3-carboxylic acid (1.18 g, 3.78 mmol) and triethylamine (5 ml) and stirred at 140° C. for 4 days under a nitrogen atmosphere. After cooling, dimethyl sulfoxide was evaporated under reduced pressure, the thus obtained residue was dissolved in chloroform (50 ml) and washed with a 10% citric acid aqueous solution (50 ml) and saturated brine (100 ml) in that order and then the organic layer was dried over anhydrous sodium sulfate. After filtration, the filtrate was concentrated under reduced pressure. The thus obtained residue was subjected to flash silica gel chromatography and eluted with an eluant of chloroform:methanol=9:1. The eluate was concentrated under reduced pressure. To the thus obtained residue, which was cooled in an ice bath, was added dropwise concentrated hydrochloric acid (5 ml), followed by 30 minutes of stirring at room temperature. After adding 1 N hydrochloric acid (30 ml) to the reaction solution, the aqueous solution was washed with chloroform (50 ml×2) and adjusted to pH 12.0 with a sodium hydroxide aqueous solution. The aqueous solution was washed with chloroform (100 ml), adjusted to pH 7.4 with 1 N hydrochloric acid and then extracted with chloroform (150 ml×3). The organic layers were combined, dried over anhydrous sodium sulfate and then filtered, and the filtrate was concentrated under reduced pressure. The thus obtained residue was subjected to preparative TLC (development with the bottom layer of a mixture of chloroform:methanol:water=7:3:1) to obtain a crude title compound, and this was recrystallized from a mixture of ethanol and ether to obtain 157 mg (17%) of the title compound.

Melting point: 177–184° C.

$^1$H-NMR (400 MHz, CDCl$_3$) δ: 1.16–2.34 (13 H, m), 2.47–2.60 (1 H, m), 3.35 (1 H, t, J=8.79 Hz), 3.53 (1 H, q, J=12.21 Hz), 3.78–3.83 (1 H, m), 4.09–4.21 (2 H, m), 4.76–4.95 (1 H, m), 5.42 (1 H, dt, J=3.41, 55.18 Hz), 6.53 (2 H, brs), 8.60 (1 H, d, J=3.41 Hz)

Elemental analysis data; for $C_{22}H_{25}F_3N_4O_3 \cdot 0.5H_2O$: calcd.; C, 57.51; H, 5.70; N, 12.19 found; C, 57.59; H, 5.52; N, 11.89

The antimicrobial activity expressed as a minimum inhibitory concentration (MIC, μg/ml) of the compounds of Example Nos. 3–8, 12 and 13 with respect to various microbial strains is set forth in Tables 1 to 3 below.

TABLE 1

| Strain/Compound | Example No. | | |
|---|---|---|---|
| | 3 | 4 | 5 |
| E. coli, NIHJ | ≦0.003 | 0.013 | ≦0.003 |
| S. flexneli, 2A 5503 | ≦0.003 | 0.013 | ≦0.003 |
| Pr. vulgaris, 08601 | 0.025 | 0.10 | 0.013 |
| Pr. mirabilis, IFO-3849 | 0.05 | 0.20 | 0.025 |
| Ser. marcescens, 10100 | 0.10 | 0.20 | 0.05 |
| Ps. aeruginosa, 32104 | 0.20 | 0.78 | 0.10 |
| Ps. aeruginosa, 32121 | 0.10 | 0.39 | 0.05 |
| Ps. maltophilia, IID-1275 | 0.10 | 0.20 | 0.05 |
| S. aureus, 209P | ≦0.003 | ≦0.003 | ≦0.003 |
| S. epidermidis, 56500 | ≦0.003 | 0.013 | ≦0.003 |
| Str. pyogenes, G-36 | ≦0.003 | 0.025 | ≦0.003 |
| Str. faecalis, ATCC-19433 | 0.025 | 0.10 | 0.013 |
| S. aureus, 870307 | 0.025 | 0.10 | 0.006 |

TABLE 2

| Strain/Compound | Example No. | | |
|---|---|---|---|
| | 6 | 7 | 8 |
| E. coli, NIHJ | 0.013 | ≦0.003 | 0.025 |
| S. flexneli, 2A 5503 | 0.025 | ≦0.003 | 0.05 |
| Pr. vulgaris, 08601 | 0.05 | 0.05 | 0.10 |
| Pr. mirabilis, IFO-3849 | 0.20 | 0.025 | 0.78 |
| Ser. marcescens, 10100 | 0.10 | 0.05 | 0.39 |
| Ps. aeruginosa, 32104 | 0.78 | 0.10 | 1.56 |
| Ps. aeruginosa, 32121 | 0.20 | 0.05 | 0.39 |
| Ps. maltophilia, IID-1275 | 0.39 | 0.05 | 0.39 |
| S. aureus, 209P | 0.006 | ≦0.003 | 0.025 |
| S. epidermidis, 56500 | 0.025 | ≦0.003 | 0.05 |
| Str. pyogenes, G-36 | 0.025 | ≦0.003 | 0.10 |
| Str. faecalis, ATCC-19433 | 0.10 | 0.013 | 0.20 |
| S. aureus, 870307 | 0.39 | 0.013 | 0.78 |

TABLE 3

| Strain/Compound | Example No. | |
|---|---|---|
| | 12 | 13 |
| E. coli, NIHJ | ≦0.003 | ≦0.003 |
| S. flexneli, 2A 5503 | 0.013 | 0.006 |
| Pr. vulgaris, 08601 | 0.013 | 0.025 |
| Pr. mirabilis, IFO-3849 | 0.05 | 0.05 |
| Ser. marcescens, 10100 | 0.10 | 0.20 |
| Ps. aeruginosa, 32104 | 0.39 | 0.20 |
| Ps. aeruginosa, 32121 | 0.10 | 0.10 |
| Ps. maltophilia, IID-1275 | 0.20 | 0.20 |
| S. aureus, 209P | ≦0.003 | ≦0.003 |

TABLE 3-continued

| Strain/Compound | Example No. 12 | Example No. 13 |
|---|---|---|
| S. epidermidis, 56500 | 0.013 | 0.006 |
| Str. pyogenes, G-36 | 0.006 | 0.006 |
| Str. faecalis, ATCC-19433 | 0.025 | 0.025 |
| S. aureus, 870307 | 0.025 | 0.05 |

The following are working examples in accordance with the second aspect of this invention.

Referential Example 9-1

Ethyl 3-(1-tert-butoxycarbonylaminocyclopropyl)propiolate

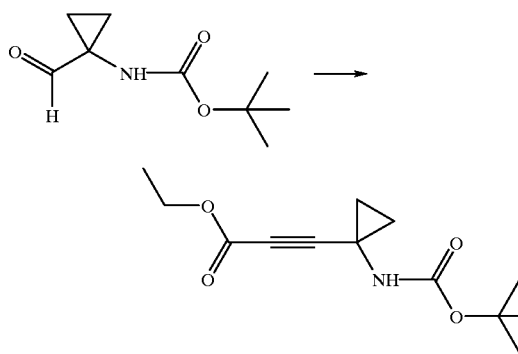

Under a nitrogen atmosphere, chloromethyltrimethylphosphonium chloride (5.156 g, 14.85 mmol) was suspended in dry tetrahydrofuran (30 ml). After cooling the suspension to provide an internal temperature of −55° C., a 1.68 M solution of n-butyllithium in n-hexane (8.87 ml, 14.90 mmol) was added dropwise thereinto over a period of 5 minutes. Then, the reaction suspension was stirred under ice cooling for 30 minutes and then at room temperature for an additional 3 hours followed by cooling to provide an internal temperature of −55° C. Into this reaction suspension was added dropwise a solution of 1-tert-butoxycarbonylaminocyclopropane carbaldehyde (2.49 g, 13.50mmol) in dry tetrahydrofuran (10 ml) over a period of 10 minutes and the resultant mixture was stirred at −50° C. for 1 hour and then under ice cooling for additional 30 minutes. The reaction suspension was cooled to −78° C. and a 1.68 M solution of n-butyllithium in n-hexane (17.68 ml, 29.70 mmol) was added dropwise thereinto over a period of 10 minutes followed by stirring at −78° C. for 20 minutes. Next, ethyl chloroformate (1.61 ml, 16.88 mmol) was added dropwise into this reaction suspension followed by stirring at −78° C. for 1.5 hours and then under ice cooling for 1 hour. Under ice cooling, a saturated aqueous solution of sodium chloride (30 ml) was added to the reaction suspension and the organic layer was separated. The aqueous layer was extracted with diethyl ether (30 ml×2) and the combined organic layer was washed with a saturated aqueous solution of sodium chloride (30 ml) and dried over anhydrous magnesium sulfate. After filtering, the filtrate was concentrated under reduced pressure and the residue was subjected to flash silica gel column chromatography (eluent: n-hexane:ethyl acetate=5:1) to obtain 2.178 g (63.9%) of the title compound as a colorless oily substance.

$^1$H-NMR (400 MHz, CDCl$_3$) δ: 5.04 (brs, 1H), 4.27 (q, J=7.16 Hz, 2H), 1.44 (s, 9H), 1.28 (t, J=7.16 Hz, 3H), 1.15 (m, 2H),1.06 (m, 2H).

Referential Example 9-2

Ethyl 1-benzyl-4-(1-tert-butoxycarbonylaminocyclopropyl)-3-pyrroline-3-carboxylate

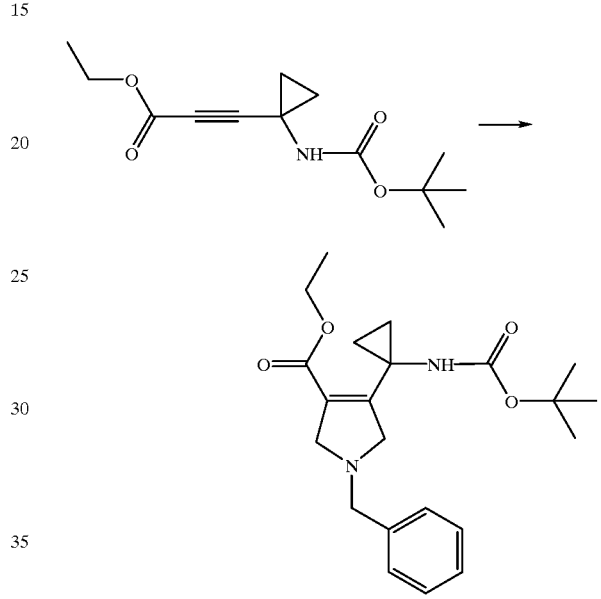

N-Benzyl-N-(n-butoxymethyl)trimethylsilylmethylamine (2.006 g, 7.176 mmol) and ethyl 3-(1-tert-butoxycarbonylaminocyclopropyl)propiolate (1.136 g, 4.485 mmol) were dissolved in dry dichloromethane (9 ml). While stirring at room temperature, a 1.0 M solution of trifluoroacetic acid in dichloromethane (0.72 ml, 0.72 mmol) was added thereto and the liquid reaction mixture was stirred for 3 hours. Then a saturated aqueous solution of sodium bicarbonate (20 ml) was added to the liquid reaction mixture followed by extraction with dichloromethane (20 ml×3). The combined organic layer was washed with a saturated aqueous solution of sodium chloride (30 ml) and dried over anhydrous magnesium sulfate. After filtering, the filtrate was concentrated under reduced pressure and the residue was subjected to flash silica gel column chromatography (eluent: chloroform) to obtain 1.449 g (83.6%) of the title compound as a colorless oily substance.

$^1$H-NMR (400 MHz, CDCl$_3$) δ: 7.40–7.11 (m, 5H), 5.17 (brs,. 1H), 4.12 (q, J=6.83 Hz, 2H), 3.85 (m, 2H), 3.72 (m, 2H), 3.67 (s, 2H), 1.44 (s, 9H), 1.24 (t, J=6.83 Hz, 3H), 1.14 (m, 2H), 1.01 (m, 2H).

Referential Example 9-3

Ethyl cis-1-benzyl-4-(1-tert-butoxycarbonylaminocyclopropyl)-pyrrolidine-3-carboxylate

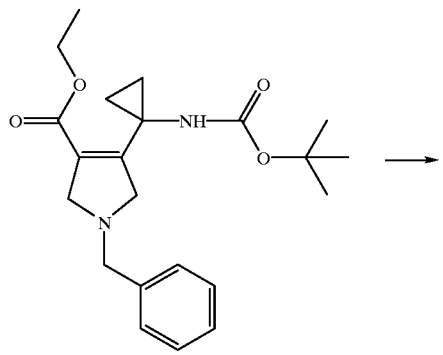

Under a nitrogen gas stream, bis(bicyclo[2.2.1]hepta-2,5-diene)rhodium (I) perchlorate (54.5 mg, 0.14 mmol) and 1,2-bis(diphenylphosphino)ethane (67.4 mg, 0.17 mmol) were dissolved in degassed methanol (25 ml) and stirred at room temperature for 10 minutes. To this catalyst solution was added a solution of ethyl 1-benzyl-4-(1-tert-butoxycarbonylaminocyclopropyl)-3-pyrroline-3-carboxylate (1.090 g, 2.820 mmol) in dry and degassed methanol (15 ml). The thus obtained liquid reaction mixture was then stirred under a hydrogen atmosphere (1 kg/cm$^2$) at room temperature for 2.5 hours. After adding active carbon (1 g), the liquid reaction mixture was allowed to stand at room temperature for 30 minutes and then filtered-through celite (washed with methanol). The filtrate was concentrated under reduced pressure and the residue was subjected to flash silica gel column chromatography (eluent:n-hexane:ethyl acetate=5:1) to obtain 1.071 g (97.8%) of the title compound as colorless crystals.

$^1$H-NMR (400 MHz, CDCl$_3$) δ: 7.40–7.19 (m, 5H), 5.07 (brs, 1H), 4.13 (q, J=7.33 Hz, 2H), 3.63 (s, 2H), 2.87 (m, 1H), 2.67 (m, 1H), 2.54 (m, 1H), 2.35 (m, 1H), 2.15 (m, 1H), 1.79 (m, 1H), 1.46 (s, 9H), 1.23 (t, J=7.33 Hz, 3H), 0.85 (m, 2H), 0.69 (m, 2H).

Referential Example 9-4 cis-1-Benzyl-4-(1-tert-butoxycarbonylaminocyclopropyl)-3-hydroxymethylpyrrolidine

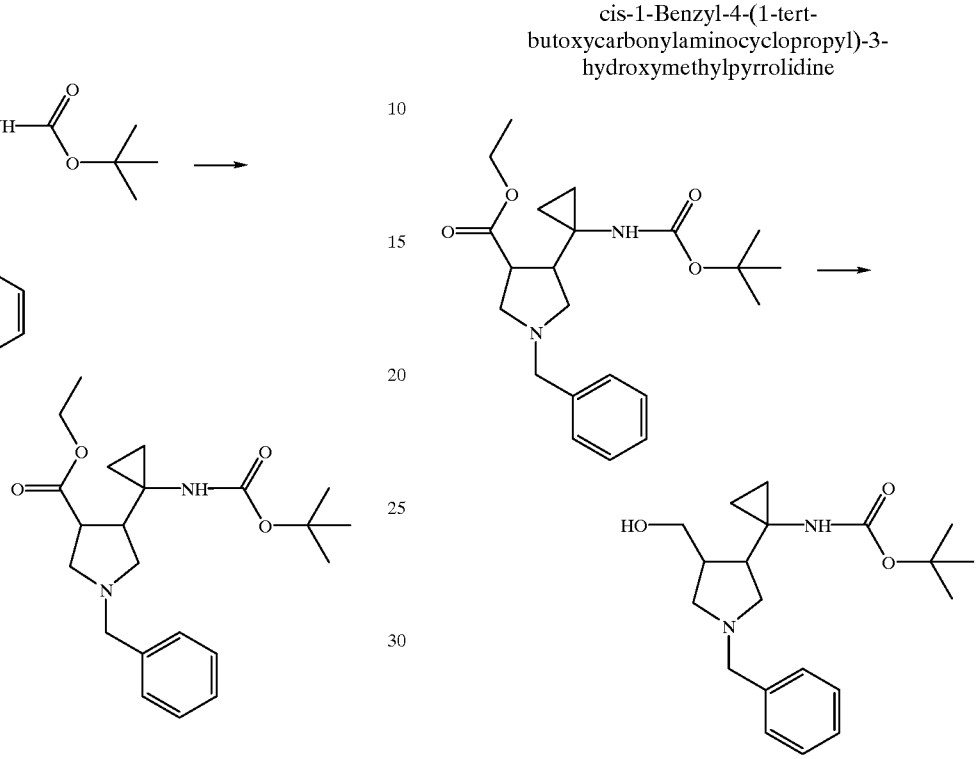

Under a nitrogen gas stream, lithium aluminum hydride (195.6 mg, 5.135 mmol) was suspended in dry tetrahydrofuran (40 ml). Under stirring at −15° C., a solution of ethyl cis-1-benzyl-4-(1-tert-butoxycarbonylaminocyclopropyl)-pyrrolidine-3-carboxylate (1.001 g, 2.577 mmol) in dry tetrahydrofuran (10 ml) was added dropwise thereinto over a period of 15 minutes. After stirring the reaction suspension under ice cooling for 3.5 hours, cooling water (5 ml) was slowly added thereto and the mixture was stirred at room temperature for an additional 15 minutes. The reaction suspension was filtered through celite (washed with diethyl ether). The filtrate was concentrated under reduced pressure and dried to obtain 833.9 mg (93.4%) of the title compound as a colorless oily substance.

$^1$H-NMR (400 MHz, CDCl$_3$) δ: 7.39–7.00 (m, 5H), 5.10 (brs, 1H), 3.69 (m, 2H), 3.58 (s, 2H), 2.99 (m, 1H), 2.61 (m, 1H), 2.51 (m, 1H), 2.27 (m, 1H), 2.00 (m, 1H), 1.94 (brs, 1H), 1.74 (m, 1H), 1.42 (s, 9H), 0.90 (m, 1H), 0.74–0.61 (m, 3H).

Referential Example 9-5 cis-4-(1-tert-Butoxycarbonylaminocyclopropyl)-3-hydroxymethylpyrrolidine

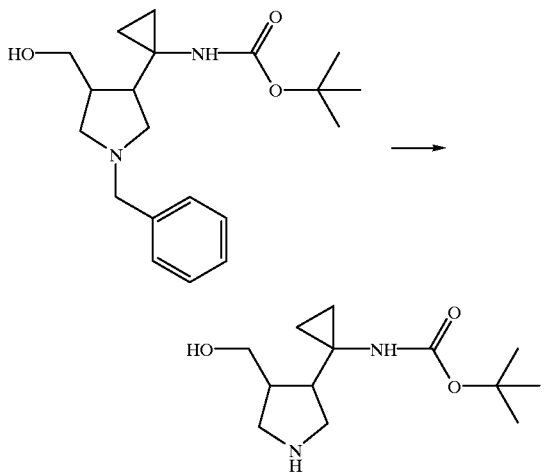

cis-1-Benzyl-4-(1-tert-butoxycarbonylaminocyclopropyl)-3-hydroxymethylpyrrolidine (820.1 mg, 2.376 mmol) was dissolved in methanol (50 ml). After adding a 5% palladium-carbon catalyst (moisture content: 55.6%, 750 mg), the mixture was stirred under elevated hydrogen pressure (4.5 kg/cm$^2$) over a period of one day and night. After filtering off the catalyst through celite (washed with methanol), the filtrate was concentrated under reduced pressure to obtain 578.8 mg (91.0%) of the title compound as a white amorphous substance.

$^1$H-NMR (400 MHz, CDCl$_3$) δ: 5.05 (brs, 1H), 3.72 (m, 2H), 3.15 (m, 2H), 2.82 (m, 2H), 2.29 (m, 1H), 1.94 (br, 2H), 1.76 (m, 1H), 1.42 (s, 9H), 0.92 (m, 2H), 0.82 (m, 1H), 0.61 (m, 1H).

Example 14

5-Amino-7-[cis-4-(1-aminocyclopropyl)-3-hydroxymethyl-1-pyrrolidinyl]-1-cyclopropyl-6-fluoro-1,4-dihydro-8-methyl-4-oxoquinoline-3-carboxylic acid

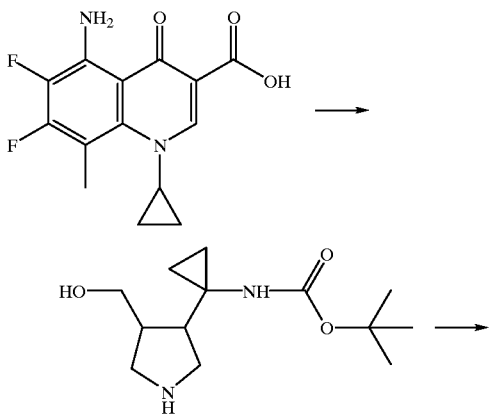

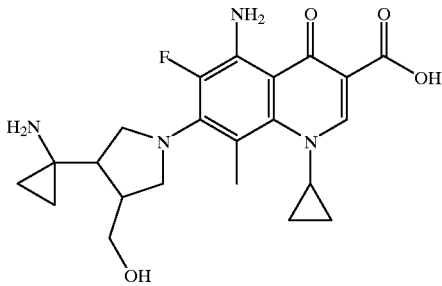

cis-4-(1-tert-Butoxycarbonylaminocyclopropyl)-3-hydroxymethylpyrrolidine (550.1 mg, 2.146 mmol) was dissolved in dimethyl sulfoxide (15 ml) and triethylamine (3.5 ml) and 5-amino-1-cyclopropyl-6,8-difluoro-1,4-dihydro-8-methyl-4-oxoquinoline-3-carboxylic acid (300.2 mg, 1.020 mmol) were added thereto. Then the mixture was stirred under a nitrogen atmosphere in an oil bath at 150° C. for 22 hours. After allowing it to cool, dimethyl sulfoxide was removed by evaporation. The residue was dissolved in chloroform (100 ml), washed successively with a 10% aqueous solution of citric acid (100 ml) and a saturated aqueous solution of sodium chloride (50 ml). The organic layer was dried over anhydrous magnesium sulfate. After filtering, the filtrate was concentrated under reduced pressure. Under ice cooling, concentrated hydrochloric acid (10 ml) was added dropwise into the residue followed by stirring for 1 hour. The liquid reaction mixture was washed with dichloromethane (20 ml×4) and the pH value of the aqueous layer was adjusted to 12 with a 15% aqueous solution of sodium hydroxide followed by washing with dichloromethane (20 ml×2). The pH value of this aqueous solution was adjusted to 7.2 with 1 N hydrochloric acid followed by extraction with chloroform (100 ml×4). The combined organic layer was dried over anhydrous magnesium sulfate and filtered. The filtrate was concentrated under reduced pressure and the crude product thus obtained was recrystallized from a 2-propanol/diisopropyl ether system. The crystals thus obtained were dried under reduced pressure at 70° C. for 18 hours to give 112.4 mg (25.6%) of the title compound as yellow crystals.

Melting point: 158.8–159.9° C. (decomp.).

$^1$H-NMR (400 MHz, 0.1 N-NaOD) δ: 8.39 (s, 1H), 3.99 (m, 1H), 3.80 (dd, J=11.23, 5.37 Hz, 1H), 3.62 (m, 2H), 3.51 (d, J=7.32, 2H), 3.41 (t, J=7.81 Hz, 1H), 2.45 (m, 1H), 2.37 (s, 3H), 1.71 (q, J=7.81, 1H), 1.18 (m, 2H), 0.74 (m, 1H), 0.70 (m, 1H), 0.55 (m, 4H).

Elemental analysis data: as $C_{22}H_{27}FN_4O_4$ calcd.: C, 61.31; H, 6.32; N, 13.02 found: C, 61.25; H, 6.32; N, 12.74.

Referential Example 10-1

4-(S)-(1-Ethoxycarbonylcyclopropyl)-3-(R)-fluoro-1-[1-(S)-phenylethyl]-2-pyrrolidone

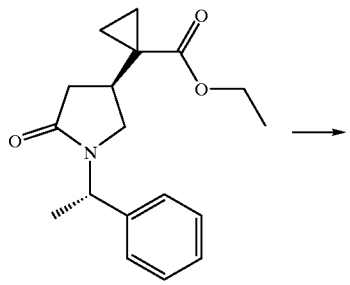

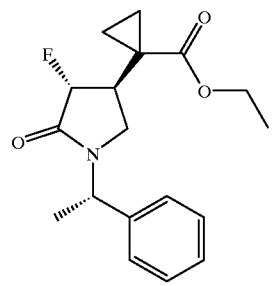

Under a nitrogen atmosphere, diisopropylamine (3.99 ml, 30.4 mol) was dissolved in dry tetrahydrofuran (50 ml). After cooling the solution to −78° C., a 1.68 M solution of n-butyllithium in n-hexane (18.1 ml, 30.4 mmol) was added dropwise thereinto over a period of 10 minutes. Then the liquid reaction mixture was stirred at −10° C. for 20 minutes and cooled to −78° C. Next, a solution of 4-(S)-(1-ethoxycarbonylcyclopropyl)-1-[1-(S)-phenylethyl]-2-pyrrolidone (7.052 g, 23.40 mmol) in dry tetrahydrofuran (30 ml) was added dropwise thereinto over a period of 15 minutes. The liquid reaction mixture was stirred at −78° C. for 1 hour. Then a solution of N-fluorobenzenedisulfonimide (11.81 g, 37.44 mmol) in dry tetrahydrofuran (60 ml) was added dropwise thereinto at the same temperature over a period of 25 minutes. The liquid reaction mixture was stirred at −78° C. for 2 hours and then heated to room temperature followed by stirring for an additional 20 minutes. Under ice cooling, a saturated aqueous solution of ammonium chloride (200 ml) was added to the liquid reaction mixture. The organic layer was separated and the aqueous layer was extracted with diethyl ether (200 ml×2). The combined organic layer was washed with water (200 ml×3) and dried over anhydrous magnesium sulfate. After filtering, the filtrate was concentrated under reduced pressure and the residue was subjected to flash silica gel column chromatography (eluent:n-hexane:ethyl acetate=3:1) to obtain 5.276 g (70.6%) of the title compound as a colorless oily substance.

$^1$H-NMR (400 MHz, CDCl$_3$) δ: 0.76–0.81 (1H, m), 0.89–0.93 (1H, m), 1.09 (3H, t, J=6.84 Hz), 1.24–1.34 (2H, m), 1.58 (3H, d, J=7.33 Hz), 2.23 (1H, dq, J=28.32, 8.30 Hz), 2.88–2.93 (1H, m), 3.48 (1H, t, J=9.28 Hz), 3.92–4.08 (2H, m), 5.14 (1H, dd, J=53.71, 7.81 Hz), 5.54 (1H, q, J=7.33 Hz), 7.27–7.34 (5H, m).

Referential Example 10-2

4-(S)-(1-Ethoxycarbonylcyclopropyl)-3-(S)-fluoro-1-[1-(S)-phenylethyl]-2-pyrrolidone

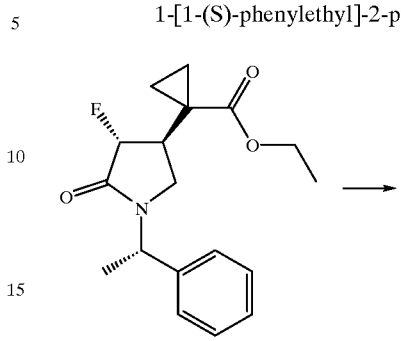

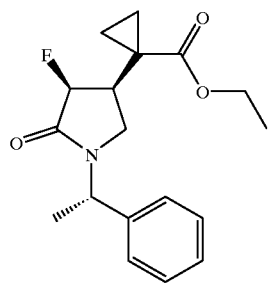

Under a nitrogen atmosphere, diisopropylamine (7.22 ml, 51.52 mmol) was dissolved in dry tetrahydrofuran (100 ml). After cooling the solution to −78° C., a 1.68 M solution of n-butyllithium in n-hexane (28.1 ml, 47.21 mmol) was added dropwise thereinto over a period of 15 minutes. Then the liquid reaction mixture was stirred at 0° C. for 10 minutes and cooled to −78° C. Next, a solution of 4-(S)-(1-ethoxycarbonylcyclopropyl)-3-(R)-fluoro-1-[1-(S)-phenylethyl]-2-pyrrolidone (13.72 g, 42.96 mmol) in dry tetrahydrofuran (40 ml) was added dropwise thereinto over a period of 20 minutes. The liquid reaction mixture was stirred at −78° C. for 20 minutes. Then, a solution of 2,6-di-tert-butylphenol (10.63 g, 51.52 mmol) in dry tetrahydrofuran (40 ml) was added dropwise thereinto over a period of 20 minutes. The liquid reaction mixture was stirred at −78° C. for 10 minutes and then heated to room temperature. Under ice cooling, a saturated aqueous solution of ammonium chloride (200 ml) was added to the liquid reaction mixture. The organic layer was separated and the aqueous layer was extracted with diethyl ether (200 ml×2). The combined organic layer was washed with water (400 ml×2) and dried over anhydrous magnesium sulfate. After filtering, the filtrate was concentrated under reduced pressure and the residue was subjected to flash silica gel column chromatography (eluent:n-hexane:ethyl acetate=3:1) to obtain 10.19 g (74.2%) of the title compound as a colorless oily substance.

$^1$H-NMR (400 MHz, CDCl$_3$) δ: 0.57–0.63 (1H, m), 0.78–0.84 (1H, m), 1.07–1.13 (1H, m), 1.26 (3H, t, J=7.09 Hz), 1.23–1.29 (1H, m), 1.54 (3H, d, J=7.32 Hz), 2.59 (1H, t, J=9.77 Hz), 3.05 (1H, dq, J=28.82, 8.30 Hz), 3.25 (1H, t, J=9.77 Hz), 4.00–4.16 (2H, m), 5.15 (1H, dd, J=52.73, 6.35 Hz), 5.53 (1H, q, J=7.32 Hz), 7.27–7.38 (5H, m).

Referential Example 10-3

4-(S)-(1-Ethoxycarbonylcyclopropyl)-3-(S)-fluoro-
1-[1-(S)-phenylethyl]-2-pyrrolidinthione

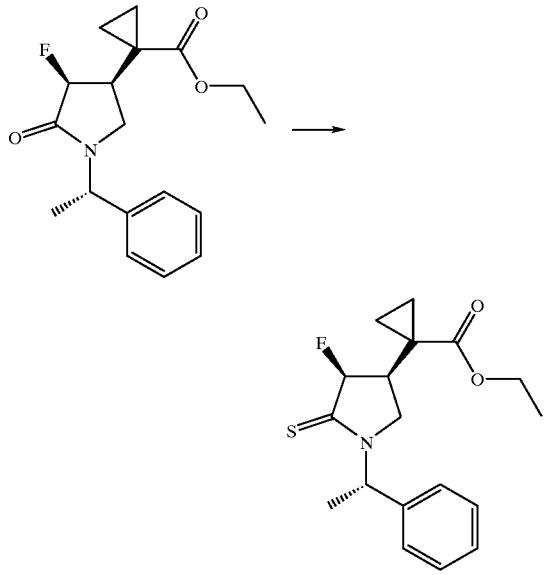

4-(S)-(1-Ethoxycarbonylcyclopropyl)-3-(S)-fluoro-1-[1-(S)-phenylethyl]-2-pyrrolidone (6.86 g, 21.48 mmol) was dissolved in dry toluene (100 ml). After adding Lawesson's reagent (5.21 g, 12.89 mmol), the mixture was heated at 60° C. for 30 minutes. After allowing the liquid reaction mixture to cool, toluene was evaporated under reduced pressure and the residue was subjected to flash silica gel column chromatography (eluent:n-hexane:ethyl acetate=4:1) to obtain 6.49 g (90.1%) of the title compound as a pale yellow oily substance.

$^1$H-NMR (400 MHz, CDCl$_3$) δ: 0.59–0.66 (1H, m), 0.86–0.92 (1H, m), 1.08–1.15 (1H, m), 1.20 (3H, t, J=7.33 Hz), 1.24–1.31 (1H, m), 1.60 (3H, d, J=7.32 Hz), 2.85 (1H, dd, J=11.23, 9.28 Hz), 3.16 (1H, dq, J=30.27, 8.30 Hz), 3.50 (1H, dd, J=11.23, 9.28 Hz), 4.04–4.15 (2H, m), 5.32 (1H, dd, J=52.73, 5.38 Hz), 6.28–6.34 (1H, m), 7.30–7.41 (5H, m).

Referential Example 10-4

4-(S)-(1-Ethoxycarbonylcyclopropyl)-3-(S)-fluoro-
1-[1-(S)-phenylethyl]pyrrolidine

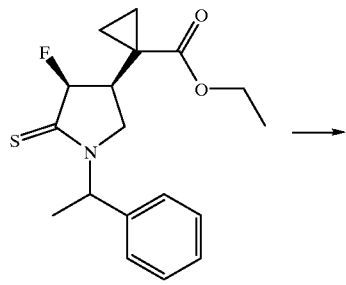

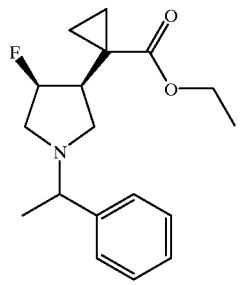

4-(S)-(1-Ethoxycarbonylcyclopropyl)-3-(S)-fluoro-1-[1-(S)-phenylethyl]-2-pyrrolidinthione (6.49 g, 19.35 mmol) was dissolved in dry tetrahydrofuran (150 ml). After adding Raney nickel catalyst (15 ml), the mixture was stirred at room temperature for 30 minutes. After eliminating the catalyst by filtering through celite (washed with tetrahydrofuran), the filtrate was concentrated under reduced pressure. The residue was dissolved in diethyl ether (200 ml) and the thus obtained solution was washed with a 10% aqueous solution of ammonia (200 ml×2) and a saturated aqueous solution of sodium chloride (150 ml) and dried over anhydrous sodium sulfate. After filtering, the filtrate was concentrated under reduced pressure to obtain 5.08 g (86.0%) of the title compound as a colorless oily substance.

$^1$H-NMR (400 MHz, CDCl$_3$) δ: 0.54–0.60 (1H, m), 0.95–1.08 (2H, m), 1.22 (3H, t, J=7.33 Hz), 1.25–1.32 (1H, m), 1.35 (3H, d, J=6.35 Hz), 1.99 (1H, t, J=9.28 Hz), 2.42 (1H, t, J=8.30 Hz), 2.63 (1H, ddd, J=33.21, 11.72, 1.95 Hz), 2.99 (1H, dm, J=28.32 Hz), 3.25–3.37 (2H, m), 4.03–4.16 (2H, m), 5.33 (1H, dm, J=55.67 Hz), 7.21–7.36 (5H, m).

Referential Example 10-5

1-Benzyloxycarbonyl-4-(S)-(1-
ethoxycarbonylcyclopropyl)-3-(S)-fluoropyrrolidine

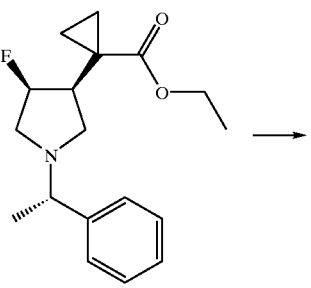

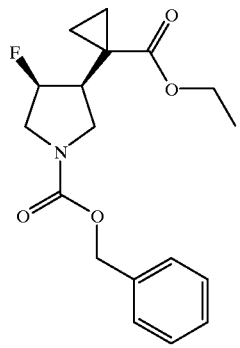

4-(S)-(1Ethoxycarbonylcyclopropyl)-3-(S)-fluoro-1-[1-(S)-phenylethyl]pyrrolidine (5.08 g, 16.63 mmol) was dissolved in dry dichloromethane (50 ml). Under ice cooling, benzyl chloroformate (3.56 ml, 25.0 mmol) was added dropwise into this solution. Then the liquid reaction mixture was heated under reflux for 1 hour and dichloromethane was evaporated under reduced pressure. The residue was subjected to flash silica gel column chromatography (eluent:n-hexane:ethyl acetate=3:1) to obtain 4.67 g (83.7%) of the title compound as a colorless oily substance.

$^1$H-NMR (400 MHz, CDCl$_3$) δ: 0.71–0.78 (1H, m), 1.11–1.23 (2H, m), 1.24 (3H, t, J=6.84 Hz), 1.29–1.37 (1H, m), 2.93–3.00 (1H, m), 3.10 (1H, dm, J=34.67 Hz), 3.54–3.84 (2H, m), 4.09–4.18 (2H, m) 5.14 (2H, s), 5.34 (1H, ddm, J=53.71, 16.6 Hz), 7.29–7.38 (5H, m).

Referential Example 10-6

1-[1-Benzyloxycarbonyl-4-(S)-fluoro-3-(S)-pyrrolidinyl]-cyclopropanecarboxylic acid

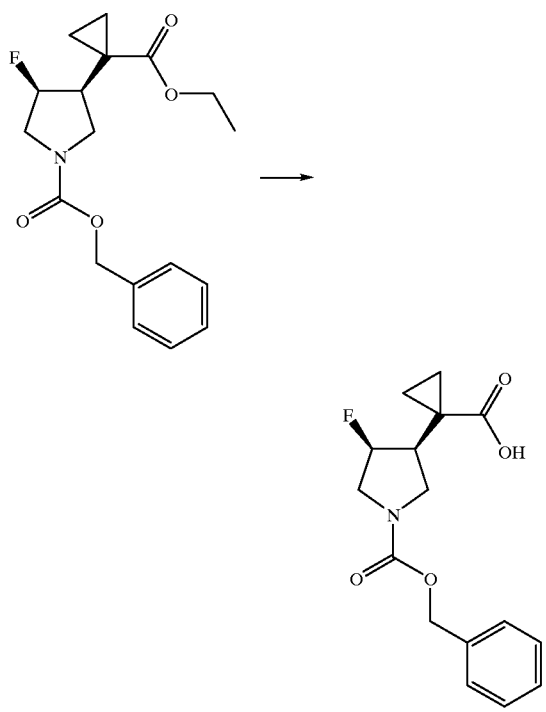

1-Benzyloxycarbonyl-4-(S)-(1-ethoxycarbonyl-cyclopropyl)-3-(S)-fluoropyrrolidine (4.67 g, 13.92 mmol) was dissolved in ethanol (50 ml). Then a 1 N aqueous solution of sodium hydroxide (50 ml) was added dropwise into this solution. Then the liquid reaction mixture was stirred at 40° C. for 1.5 hours and ethanol was removed by evaporation under reduced pressure. Water (50 ml) was added to the residue followed by washing with chloroform (100 ml). The aqueous layer was separated and acidified by adding dropwise 1 N hydrochloric acid thereinto. Next, it was extracted successively with chloroform (200 ml×2) and diethyl ether (100 ml). The combined organic layer was dried over anhydrous sodium sulfate. After filtering, the filtrate was concentrated under reduced pressure to obtain 3.94 g (92.1%) of the title compound as a colorless amorphous substance.

$^1$H-NMR (400 MHz, CDCl$_3$) δ: 0.79–0.89 (1H, m), 1.18–1.35 (2H, m), 1.37–1.47 (1H, m), 2.90–3.18 (2H, m), 3.50–3.84 (3H, m), 5.13 (2H, s), 5.31 (1H, ddm, J=53.22, 15.13 Hz), 7.26–7.42 (5H, m).

Referential Example 10-7

1-Benzyloxycarbonyl-4-(R)-(1-tert-butoxycarbonylaminocyclopropyl)-3-(S)-pyrrolidine

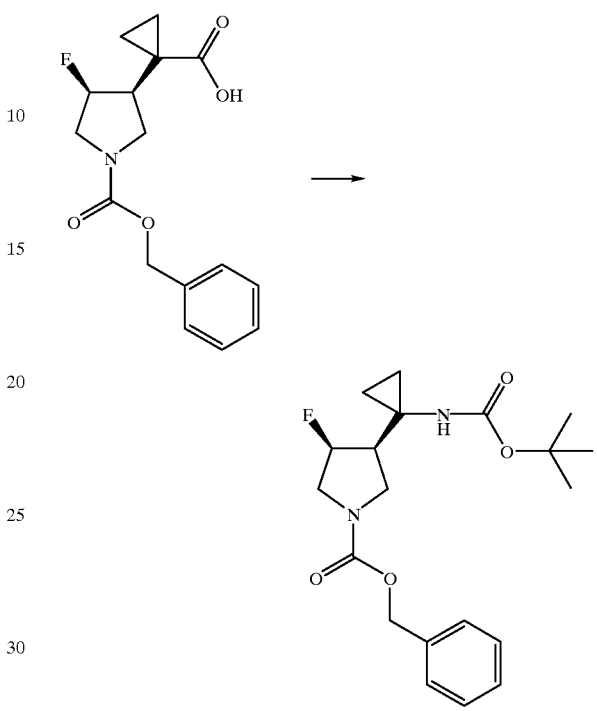

1-[1-Benzyloxycarbonyl-4-(S)-fluoro-3-(S)-pyrrolidinyl] cyclopropanecarboxylic acid (3.22 g, 10.48 mmol) was dissolved in dry acetonitrile (80 ml). After adding N,N'-carbonyldiimidazole (2.55 g, 15.73 mmol), the liquid reaction mixture was stirred at room temperature for 30 minutes. Next, ammonia gas was bubbled thereinto at the same temperature. Then the liquid reaction mixture was concentrated under reduced pressure. Water (80 ml) was added to the residue followed by extraction with chloroform (80 ml×2). The combined organic layer was dried over anhydrous sodium sulfate. After filtering, the filtrate was concentrated under reduced pressure. The residue was dissolved in tert-butyl alcohol (100 ml) and lead tetraacetate (7.93 g, 15.70 mmol) was added thereto. After heating under reflux for 30 minutes, the liquid reaction mixture was allowed to cool and diethyl ether (50 ml) and sodium hydrogencarbonate (10 g) were added thereto. Then the mixture was stirred at room temperature for 10 minutes and filtered. The filtrate was concentrated under reduced pressure. After adding ethyl acetate (150 ml) to the residue, the mixture was washed with a saturated aqueous solution of sodium bicarbonate and dried over anhydrous sodium sulfate. After filtering, the filtrate was concentrated under reduced pressure and the residue was subjected to flash silica gel column chromatography (eluent:n-hexane:ethyl acetate=3:2) to obtain 3.216 g (81.2%) of the title compound as a colorless oily substance.

$^1$H-NMR (400 MHz, CDCl$_3$) δ: 0.65–0.74 (1H, m), 0.70–0.84 (1h, m), 0.85–1.00 (2H, m), 1.42 (9H, s), 2.21 (1H, ddm, J=80.57, 36.14 Hz), 3.08–3.24 (2H, m), 3.48–3.84 (3H, m), 5.02 (1H, brs), 5.13 (2H, s), 5.15 (1H, brd. J=53.72 Hz), 7.28–7.38 (5H, m).

Example 15

5-Amino-7-[4-(R)-(1-aminocyclopropyl)-3-(S)-fluoro-1-pyrrolidihyl]-6-fluoro-1-[2-(S)-fluoro-1-(R)-cyclopropyl]-1,4-dihydro-8-methyl-4-oxoquinoline-3-carboxylic acid hydrochloride

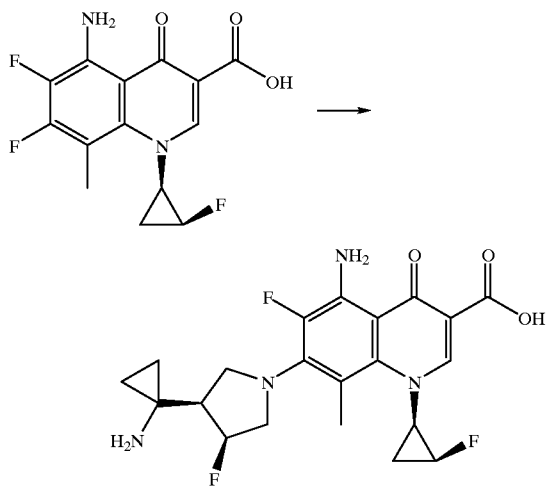

1-Benzyloxycarbonyl-4-(R)-(1-tert-butoxycarbonylaminocyclopropyl)-3-(S)-fluoropyrrolidine (1.43 g, 3.78 mmol) was dissolved in ethanol (60 ml). After adding a 5% palladium-carbon catalyst (moisture content: 55.6%, 1.5 g), the mixture was stirred under a hydrogen atmosphere for 3 hours. After filtering off the catalyst through celite (washed with methanol), the filtrate was concentrated under reduced pressure. The residue thus obtained was dissolved in dimethyl sulfoxide (12 ml) and 5-amino-6,7-difluoro-1-[2-(S)-fluoro-1-(R)-cyclopropyl]-1,4-dihydro-8-methyl-4-oxoquinoline- 3-carboxylic acid (1.18 g, 3.78 mmol) and triethylamine (3 ml) were added thereto. Then the mixture was stirred under a nitrogen atmosphere at 130° C. for 3 days. After allowing it to cool, dimethyl sulfoxide was evaporated. The residue was dissolved in chloroform (80 ml), washed successively with a 10% aqueous solution of citric acid (80 ml) and a saturated aqueous solution of sodium chloride (100 ml). The organic layer was dried over anhydrous sodium sulfate. After filtering, the filtrate was concentrated under reduced pressure. The residue was subjected to flash silica gel column chromatography (eluent:chloroform:methanol=9:1) followed by concentration of the eluate under reduced pressure. Under ice cooling, concentrated hydrochloric acid (10 ml) was added dropwise into the residue followed by stirring at room temperature for 50 minutes. After adding 1 N hydrochloric acid (30 ml), the liquid reaction mixture was washed with chloroform (50 ml×2) and its pH value was adjusted to 12.0 with an aqueous solution of sodium hydroxide followed by washing with chloroform (100 ml). The pH value of this aqueous solution was adjusted to 7.4 with 1 N hydrochloric acid followed by extraction with chloroform (150 ml×3). The combined organic layer was dried over anhydrous sodium sulfate and filtered. The filtrate was concentrated under reduced pressure and 1 N hydrochloric acid (2.0 ml) was added dropwise into the residue under ice cooling. After stirring at the same temperature for 5 minutes, the liquid reaction mixture was concentrated under reduced pressure (azeotropic distillation with ethanol, three times). The residue was recrystallized from ethanol and dried under reduced pressure to obtain 230 mg (12.1%) of the title compound as a yellow powder.

$^1$H-NMR (400 MHz, 0.1 N-NaOD) δ: 0.55–0.71 (4H, m), 1.10–1.21 (1H, m), 1.46–1.58 (1H, m), 2.30 (3H, s), 2.21–2.35 (1H, m), 3.32 (1H, t, J=8.79 Hz), 3.49 (1H, dd, J=25.88, 12.21 Hz), 3.85–3.97 (2H, m), 4.11 (1H, ddm, J=40.77, 12.45 Hz), 4.97 (1H, dm, J=70.31 Hz), 5.49 (1H, brd, J=55.18 Hz), 8.27 (1H, d, J=3.42 Hz).

Elemental analysis data: as $C_{21}H_{23}F_3N_4O_3 \cdot HCl \cdot 1.25H_2O$ calcd.: C, 50.40; H, 5.33; N, 10.87 found: C, 50.45; H, 5.44; N, 11.21.

Example 16

5-Amino-7-[4-(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methoxy-4-oxoquinoline-3-carboxylic acid

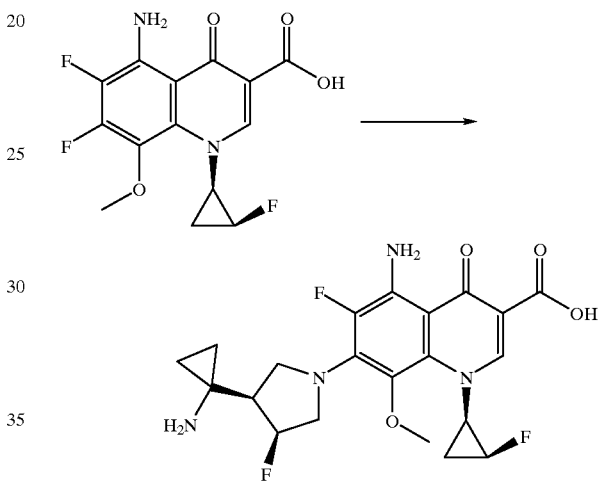

1-Benzyloxycarbonyl-4-(R)-(1-tert-butoxycarbonylaminocyclopropyl)-3-(S)-fluoropyrrolidine (400 mg, 1.06 mmol) was dissolved in ethanol (20 ml). After adding a 5% palladium-carbon catalyst (moisture content: 55.6%, 500 mg), the mixture was stirred under a hydrogen atmosphere for 18 hours. After filtering off the catalyst through celite (washed with methanol), the filtrate was concentrated under reduced pressure. The residue thus obtained was dissolved in dimethyl sulfoxide (8 ml) and 5-amino-6,7-difluoro-1-[2-(S)-fluoro-1-(R)-cyclopropyl]-1,4-dihydro-8-methoxy-4-oxoquinoline-3-carboxylic acid (289 mg, 0.88 mmol) and triethylamine (2 ml) were added thereto. Then the mixture was stirred under a nitrogen atmosphere at 100° C. for 26 hours. After allowing it to cool, dimethyl sulfoxide was removed by evaporation. The residue was dissolved in chloroform (80 ml), and washed with a 10% aqueous solution of citric acid (80 ml). The organic layer was dried over anhydrous sodium sulfate. After filtering, the filtrate was concentrated under reduced pressure. The residue was subjected to flash silica gel column chromatography (eluent: chloroform:methanol=9:1) followed by concentration of the eluate under reduced pressure. Under ice cooling, concentrated hydrochloric acid (5 ml) was added dropwise into the residue followed by stirring at room temperature for 20 minutes. After adding 1 N hydrochloric acid (30 ml), the liquid reaction mixture was washed with chloroform (50 ml×2) and its pH value was adjusted to 12.0 with an aqueous solution of sodium hydroxide followed by washing with chloroform (100 ml×2). The pH value of this aqueous solution was adjusted to 7.4 with 1 N hydrochloric acid followed by extraction with chloroform (200 ml×3). The combined organic layer was dried over anhydrous sodium sulfate and filtered. The filtrate was concentrated under reduced pressure and the residue was recrystallized from ethanol and dried under reduced pressure to obtain 170 mg (42.6%) of the title compound as a yellow powder.

$^1$H-NMR (400 MHz, 0.1 N-NaOD) δ: 0.57–0.74 (4H, m), 1.12–1.27 (1H, m), 1.36–1.48 (1H, m), 2.24 (1H, dm, J=37.60 Hz), 3.46 (3H, s), 3.53 (1H, t, J=8.79 Hz), 3.69 (1H, dd, J=25.40, 12.21 Hz), 3,86–3.94 (2H, m), 4.10 (1H, ddm, J=42.48, 12.70 Hz), 5.00 (1H, dm, J=63.97 Hz), 5.49 (1H, brd. J=54.69 Hz), 8.19 (1H, d, J=3.91 Hz).

Elemental analysis data: as $C_{21}H_{23}F_3N_4O_4$ calcd.: C, 55.75; H, 5.12; N, 12.38 found: C, 55.78; H, 5.20; N, 12.28.

Example 17

10-[4-(R)-(1-Aminocyclopropyl)-3-(S)-fluoro-1-pyrrolidinyl]-9-fluoro-2,3-dihydro-3-(S)-methyl-7-oxo-7H-pyrido[1,2,3-de][1,4]benzoxazine-6-carboxylic acid

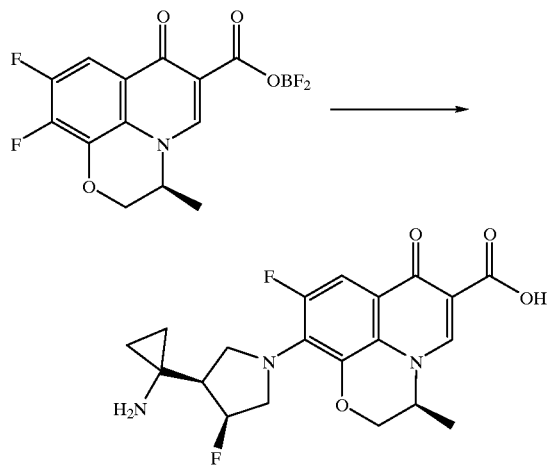

1-Benzyloxycarbonyl-4-(R)-(1-tert-butoxycarbonylaminocyclopropyl)-3-(S)-fluoropyrrolidine (913 mg, 2.41 mmol) was dissolved in methanol (50 ml). After adding a 5% palladium-carbon catalyst (moisture content: 55.6%, 1.0 g), the mixture was stirred under a hydrogen atmosphere for 3 hours. After filtering off the catalyst through celite (washed with methanol), the filtrate was concentrated under reduced pressure. The residue thus obtained was dissolved in dimethyl sulfoxide (15 ml) and 9,10-difluoro-2,3-dihdyro-3-(S)-methyl-7-oxo-7H-pyrido [1,2,3-de][1,4]benzoxazine-6-carboxylic acid-BF$_2$chelate (661 mg, 2.01 mmol) and triethylamine (336 μl, 2.41 mmol) were added thereto. Then the mixture was stirred at room temperature for 3 days. After concentrating the liquid reaction mixture under reduced pressure, water was added to the residue. The yellow crystals thus precipitated were collected by filtration and washed with water. The thus obtained crystals were suspended in a solution (200 ml) of methanol:water=1:1. After adding triethylamine (4 ml), the mixture was heated under reflux for 4 hours. After allowing it to cool, the liquid reaction mixture was concentrated under reduced pressure and the residue was dissolved in chloroform (200 ml) and washed with a 10% aqueous solution of citric acid (200 ml). The organic layer was dried over anhydrous sodium sulfate. After filtering, the filtrate was concentrated under reduced pressure. Under ice cooling, concentrated hydrochloric acid (10 ml) was added dropwise into the residue followed by stirring at room temperature for 10 minutes. After adding 1 N hydrochloric acid (30 ml), the liquid reaction mixture was washed with chloroform (50 ml×2) and its pH value was adjusted to 12.0 with an aqueous solution of sodium hydroxide. The pH value of this aqueous solution was adjusted to 7.4 with 1 N hydrochloric acid followed by extraction with chloroform (500 ml×3). The combined organic layer was dried over anhydrous sodium sulfate and filtered. The filtrate was concentrated under reduced pressure and the residue was recrystallized from ethanol and dried under reduced pressure to obtain 459 mg (56.4%) of the title compound as pale yellow crystals.

$^1$H-NMR (400 MHz, 0.1 N-NaOD) δ: 0.55–0.75 (4H, m), 1.52 (3H, d, J=6.84 Hz), 2.25 (1H, dm, J=36.62 Hz), 3.49 (1H, t, J=8.79 Hz), 3.70 (1H, dd, J=26.37, 11.72 Hz), 3.88 (1H, t, J=8.79 Hz), 4.10 (1H, dd, J=40.53, 12.70 Hz), 4.30 (1H, d, J=9.27 Hz), 4.50 (1H, d, J=9.28 Hz), 4.55–4.65 (1H, m), 5.47 (1H, dt, J=55.17, 3.42 Hz), 7.53 (1H, d, J=14.16 Hz), 8.33 (1H, s).

Referential Example 11-1

Ethyl 1-acetylcyclopropanecarboxylate

Ethyl acetoacetate (100 g, 0.77 mol) was dissolved in acetone (500 ml). To the thus obtained solution was added dibromoethane (361 g, 1.92 mol) and potassium carbonate (266 g, 1.92 mol) and the mixture was heated under reflux for 4 days. After filtering off insoluble matter, the filtrate was distilled under reduced pressure (80° C./8 mmHg) to obtain 78.1 g (65.1%) of the title compound as a colorless oily substance.

$^1$H-NMR (400 MHz, CDCl$_3$) δ: 1.29 (3H, t, J=7.33 Hz), 1.47 (4H, s), 2.47 (3H, s), 4.21 (2H, q, J=7.33 Hz).

Referential Example 11-2

Ethyl 3-(1-ethoxycarbonylcyclopropyl)-2-fluoro-2-butenoate

To a solution (1500 ml) of ethyl 1-acetylcyclopropanecarboxylate (124.5 g, 0.797 mmol) in benzene was added zinc powder (156.4 g, 2.39 mmol). While heating under reflux, a catalytic amount of iodine was added thereto. Subsequently, a solution of ethyl bromofluoroacetate (94.23 ml, 0.797 mol) in benzene (200 ml) was added dropwise thereinto over a period of 1 hour followed by heating under reflux for 1 hour. Under ice cooling, 1 N hydrochloric acid (1000 ml) was added to the liquid reaction mixture and the mixture was stirred for 1 hour. The organic layer taken up by phase separation was washed successively with 1 N hydrochloric acid, water and a saturated aqueous solution of sodium chloride, dried over anhydrous sodium sulfate and filtered. The filtrate was concentrated under reduced pressure and the residue was dissolved in pyridine (387 ml, 4.78 mol). After adding thionyl chloride (69.8 ml, 0.957 mol) at −10° C., the resultant mixture was stirred under ice cooling for 3 hours. Under ice cooling, the liquid reaction mixture was poured into 1 N hydrochloric acid (2000 ml) and ethyl acetate (1500 ml) was added thereto. The organic layer taken up by phase separation was washed successively with 1 N hydrochloric acid, water and a saturated aqueous solution of sodium chloride, dried over anhydrous sodium sulfate and filtered. The filtrate was concentrated under reduced pressure and the residue was dissolved in dichloromethane (500 ml). Under ice cooling, 1,8-azabicyclo[5.4.0]-7-undecene (131 ml, 0.877 mol) was added dropwise thereinto and then the resultant mixture was stirred at room temperature for 17 hours. After adding 1 N hydrochloric acid (2000 ml) and chloroform (1000 ml), the organic layer taken up by phase separation was washed with a saturated aqueous solution of sodium chloride, dried over anhydrous sodium sulfate and filtered. The filtrate was concentrated under reduced pressure and the residue thus obtained was subjected to flash silica gel column chromatography (eluent:n-hexane:ethyl acetate=4:1) 152.78 g (78.5%) of the title compound as an oily substance. The compound thus obtained, which was a mixture of geometrical isomers (about 1:1), was not separated but employed in the subsequent reaction as such.

Referential Example 11-3

(E)-Ethyl 4-bromo-3-(1-ethoxycarbonylcyclopropyl)-2-fluoro-2-butenoate

To a solution of ethyl 3-(1-ethoxycarbonylcyclopropyl)-2-fluoro-2-butenoate (152.78 g, 0.625 mol) in chloroform (1500 ml) were added N-bromosuccinimide (111.33 g, 0.625 mol) and a catalytic amount of 2,2'-azobis-(isobutyronitrile) and then the resultant mixture was heated under reflux for 16 hours. Then, the liquid reaction mixture was cooled and concentrated under reduced pressure. After adding benzene (300 ml), insoluble matter was filtered off and the filtrate was concentrated under reduced pressure. The residue was subjected to flash silica gel column chromatography (eluent:n-hexane:ethyl acetate=4:1) to obtain 100.5 g (49.7%) of the title compound as a yellow oily substance. On the other hand, 75 g (37.1%) of (Z)-ethyl 4-bromo-3-(1-ethoxycarbonylcyclopropyl)-2-fluoro-2-butenoate (the geometrical isomer of the title compound) was obtained as a yellow oily substance with the use of another eluent (n-hexane:ethyl acetate=2:1).
(E)-isomer
$^1$H-NMR (400 MHz, CDCl$_3$) δ: 1.23 (3H, t, J=7.08 Hz), 1.38 (3H, t, J=7.08 Hz), 1.52–1.62 (4H, br), 4.11 (2H, q, J=7.08 Hz), 4.35 (2H, q, J=7.08 Hz), 4.54 (2H, s).
(Z)-isomer
$^1$H-NMR (400 MHz, CDCl$_3$) δ: 1.21 (3H, t, J=7.08 Hz), 1.32 (3H, t, J=7.08 Hz), 1.52–1.62 (4H, br), 4.11 (2H, q, J=7.08 Hz), 4.13 (2H, s), 4.29 (2H, q, J=7.08 Hz).

Referential Example 11-4

4-(1-Ethoxycarbonylcyclopropyl)-3-fluoro-1-[1-(S)-phenylethyl]-3-pyrrolin-2-one

To a solution of (E)-ethyl 4-bromo-3-(1-ethoxycarbonylcyclopropyl)-2-fluoro-2-butenoate (143 mmol) in ethanol (1000 ml) was added sodium hydrogencarbonate (30.08 g, 358 mmol). After adding dropwise 1-(S)-phenylethylamine (20.31 ml, 158 mmol) thereinto at room temperature, the mixture was heated under reflux for 3 hours. Then the liquid reaction mixture was cooled and filtered through celite. The filtrate was concentrated under reduced pressure and the residue was subjected to flash silica gel column chromatography (eluent:n-hexane:ethyl acetate=2:1) to obtain 36.95 g (81.2%) of the-title compound as an oily substance.
$^1$H-NMR (400 MHz, CDCl$_3$) δ: 1.16 (3H, t, J=7.08 Hz), 1.22–1.30 (2H, m), 1.55–1.59 (2H, m), 1.62 (3H, d, J=7.33 Hz), 3.76 (2H, ddd, J=128.42, 18.07, 5.37 Hz), 4.08 (2H, q, J=7.08 Hz), 5.56 (1H, q, J=7.33 Hz).

Referential Example 11-5

4-(S)-(1-Ethoxycarbonylcyclopropyl)-3-(S)-fluoro-1-[1-(S)-phenylethyl]-2-pyrrolidone To a solution of 4-(1-ethoxycarbonylcyclopropyl)-3-fluoro-1-[1-(S)-phenylethyl]-3-pyrrolin-2-one (587 mg, 1.85 mmol) in ethanol (5 ml) was added Raney nickel (R-100, 2 ml). Under a hydrogen atmosphere of 5 kg/cm$^2$, the mixture was stirred at room temperature for 1 hour. Next, Raney nickel (R-100, 3 ml) was further added and stirring was continued under the same conditions for 2.5 hours. After eliminating the catalyst by filtering through celite (washed with ethanol), the filtrate was concentrated under reduced pressure. The residue was subjected to flash silica gel column chromatography (eluent:n-hexane:ethyl acetate=3:1) to obtain 382 mg (64.6%) of the title compound as a colorless oily substance. The $^1$H-NMR data of this compound agreed with the data of the compound obtained in Referential Example 10-2.
$^1$H-NMR (400 MHz, CDCl$_3$) δ: 0.57–0.63 (1H, m), 0.78–0.84 (1H, m), 1.07–1.13 (1H, m), 1.26 (3H, t, J=7.09 Hz), 1.23–1.29 (1H, m), 1.54 (3H, d, J=7.32 Hz), 2.59 (1H, t, J=8.30 Hz), 3.05 (1H, dq, J=28.81, 8.30 Hz), 3.25 (1H, t, J=8.30 Hz), 4.00–4.16 (2H, m), 5.15 (1H, dd, J=52.73, 6.35 Hz), 5.53 (1H, q, J=7.32 Hz), 7.27–7.38 (5H, m).

Referential Example 11-6

4-(S)-(1-Carboxycyclopropyl)-3-(S)-fluoro-1-[1-(S)-phenylethyl]-2-pyrrolidone 4-(S)-(1-ethoxycarbonylcyclopropyl)-3-(S)-fluoro-1-[1-(S)-phenylethyl]-2-pyrrolidone (12.56 g, 39.33 mmol) was dissolved in ethanol (120 ml) and a 1 N aqueous solution of sodium hydroxide (120 ml) was added dropwise thereinto. After stirring at 40° C. for 6 hours, ethanol was evaporated under reduced pressure. The residue was washed with chloroform (100 ml×2). Under ice cooling, the separated aqueous layer was acidified by adding dropwise 1 N hydrochloric acid thereinto and then extracted successively with chloroform (300 ml×2) and diethyl ether (300 ml). The combined organic layer was dried over anhydrous sodium sulfate and filtered. The filtrate was concentrated under reduced pressure to obtain 10.24 g (89.4%) of the title compound as colorless needles.
$^1$H-NMR (400 MHz, CDCl$_3$) δ: 0.65–0.75 (1H, m), 0.85–0.95 (1H, m), 1.15–1.25 (1H, m), 1.26–1.36 (1H, m), 1.54 (3H, d, J=7.32 Hz), 2.60. (1H, t, J=7.8 Hz), 3.01 (1H, dq, J=27.83, 7.81 Hz), 3.28 (1H, t, J=7.81 Hz), 5.16 (1H, dd, J=52.74, 6.35 Hz), 5.53 (1H, q, J=7.32 Hz), 7.27–7.38 (5H, m).

Referential Example 11-7

4-(R)-(1-tert-Butoxycarbonylaminocyclopropyl)-3-(S)-fluoro-1-[1-(S)-phenylethyl]-2-pyrrolidone
§ Process by Hoffman Rearrangement
To a solution of 4-(S)-(1-carboxycyclopropyl)-3-(S)-fluoro-1-[1-(S)-phenylethyl]-2-pyrrolidone (11.90 g, 40.85 mmol) in acetonitrile (160 ml) was added 1,1'-carbonyldiimidazole (13.25 g, 81.70 ml). The thus obtained mixture was stirred at room temperature for 30 minutes and then at 40° C. for additional 30 minutes. After cooling the liquid reaction mixture to room temperature, ammonia gas was bubbled thereinto for 30 minutes. After removing the solvent by evaporation, chloroform (500 ml) was added to the residue followed by washing with water. The organic layer was dried over anhydrous sodium sulfate and filtered. The filtrate was concentrated under reduced pressure and the residue thus obtained was dissolved in tert-butyl alcohol (200 ml) and heated to 70° C. Then lead tetraacetate (purity 90% or more, 24.15 g, 49.02 mmol) was added thereto and the mixture was heated under reflux for 20 minutes. After cooling, sodium hydrogencarbonate was added followed by dilution with ethyl acetate (300 ml). Then, insoluble matter was filtered off and the filtrate was washed with a saturated aqueous solution of sodium bicarbonate. The organic layer was dried over anhydrous sodium sulfate and the solvent was evaporated under reduced pressure to obtain 10.52 g (71.7%) of the title compound.

§ Process by Curtius Rearrangement

Under a nitrogen gas stream, toluene (100 ml) was added to 4-(S)-(1-carboxycyclopropyl)-3-(S)-fluoro-1-[1-(S)-phenylethyl]-2-pyrrolidone (3.66 g, 12.56 mmol). Next, triethylamine (3.50 ml, 25.13 mmol) was added dropwise thereinto at room temperature. When the liquid reaction mixture became a homogeneous system, diphenylphosphoric acid azide (2.71 ml, 12.56 mmol) was added and the resultant mixture was stirred at room temperature for 1 hour and then heated under reflux for 2 hours. Then, tert-butyl alcohol (100 ml) was added to the liquid reaction mixture and the mixture was further heated under reflux for 21 hours. The liquid reaction mixture was cooled and concentrated under reduced pressure. The residue thus obtained was subjected to flash silica gel column chromatography (eluent:n-hexane:ethyl acetate=1:1) to obtain 3.30 g (72.5%) of the title compound as a colorless oily substance.

$^1$H-NMR (400 MHz, CDCl$_3$) δ: 0.58–0.66 (1H, m), 0.70–0.82 (2H, m), 0.88–0.96 (1H, m), 1.31 (9H, s), 1.54 (3H, d, J=7.33 Hz), 2.36–2.52 (1H, m), 2.86 (1H, t, J=8.30 Hz), 3.32 (1H, t, J=8.30 Hz), 4.99 (1H, dd, J=52.73, 6.35 Hz), 4.99 (1H, s), 5.46 (1H, q, J=7.33 Hz), 7.27–7.42 (5H, m).

Referential Example 11-8

4-(R)-(1-tert-Butoxycarbonylaminocyclopropyl)-3-(S)-fluoro-1-[1-(S)-phenylethyl]pyrrolidine Under a nitrogen atmosphere, a 1 M solution of borane-tetrahydrofuran complex in tetrahydrofuran (120 ml) was added dropwise under ice cooling into a solution of 4-(R)-(1-tert-butoxycarbonylaminocyclopropyl)-3-(S)-fluoro-1-[1-(S)-phenylethyl]-2-pyrrolidone in tetrahydrofuran (120 ml) and the mixture was stirred at room temperature for 5 hours. After evaporating the solvent under reduced pressure, a solvent mixture (200 ml) of ethanol with water (4:1) and triethylamine (20 ml) were added to the residue followed by heating under reflux for 2 hours. Then, the liquid reaction mixture was concentrated under reduced pressure and chloroform (400 ml) was added to the residue. After washing with a saturated aqueous solution of sodium chloride, the organic layer was dried over anhydrous sodium sulfate and filtered. The filtrate was concentrated under reduced pressure and the residue was subjected to flash silica gel column chromatography (eluent:n-hexane:ethyl acetate=1:2) to obtain 7.84 g (99.4%) of the title compound as a colorless oily substance.

$^1$H-NMR (400 MHz, CDCl$_3$) δ: 0.54–0.62 (1H, m), 0.70–0.95 (3H, m), 1.35 (3H, d, J=6.35 Hz), 1.42 (9H, s), 2.27–2.45 (2H, m), 2.46–2.56 (1H, m), 2.60–2.75 (1H, m), 3.00–3.15 (1H, m), 3.29 (1H, q, J=6.35 Hz), 5.06 (1H, s), 5.05–5.20 (1H, m), 7.20–7.32 (5H, m).

Example 18

7-[4-(R)-(1-Aminocyclopropyl)-3-(S)-fluoro-1-pyrrolidinyl]-6-fluoro-1-[2-(S)-fluoro-1-(R)-cyclopropyl]-1,4-dihydro-8-methoxy-4-oxoquinoline-3-carboxylic acid 4-(R)-(1-tert-butoxycarbonylaminocyclopropyl)-3-(S)-fluoro-1-[1-(S)-phenylethyl]pyrrolidine (6.32 g, 18.14 mmol) was dissolved in ethanol (150 ml). After adding a 10% palladium-carbon catalyst (moisture content: 50.2%, 6.0 g), the mixture was stirred at 40° C. under a hydrogen atmosphere for 36 hours. After filtering off the catalyst through celite (washed with ethanol), the filtrate was concentrated under reduced pressure. The residue thus obtained was dissolved in dimethyl sulfoxide (20 ml) and 6,7-difluoro-1-[2-(S)-fluoro-1-(R)-cyclopropyl]-1,4-dihydro-8-methoxy- 4-oxoquinoline-3-carboxylic acid-BF$_2$ chelate (4.37 g, 12.09 mmol) and triethylamine (5.05 ml, 36.23 mmol) were added thereto. Then the mixture was stirred at room temperature for 23 hours. After concentrating the liquid reaction mixture under reduced pressure, water was added to the residue. The solid matter thus precipitated was collected by filtration and washed with water. The thus obtained solid was suspended in a solution (400 ml) of methanol:water=10:1. After adding triethylamihe (20 ml), the mixture was heated under reflux for 4 hours. After allowing it to cool, the liquid reaction mixture was concentrated under reduced pressure and the residue was dissolved in chloroform (500 ml) and washed with a 10% aqueous solution of citric acid (500 ml). The organic layer was dried over anhydrous sodium sulfate. After filtering, the filtrate was concentrated under reduced pressure. Under ice cooling, concentrated hydrochloric acid (30 ml) was added dropwise into the residue followed by stirring at room temperature for 2 hours. After adding 1 N hydrochloric acid (30 ml), the liquid reaction mixture was washed with chloroform (100 ml×2) and its pH value was adjusted to 12.0 with an aqueous solution of sodium hydroxide. The pH value of this aqueous solution was adjusted to 7.4 with 1 N hydrochloric acid followed by extraction with chloroform (500 ml×4). The combined organic layer was dried over anhydrous sodium sulfate and filtered. The filtrate was concentrated under reduced pressure and the residue was recrystallized from ethanol and dried under reduced pressure to obtain 4.09 g (77.3%) of the title compound as pale yellow crystals.

$^1$H-NMR (400 MHz, 0.1 N-NaOD) δ: 0.57–0.74 (4H, m), 1.32–1.45 (1H, m), 1.48–1.60 (1H, m), 2.20–2.38 (1H, m), 3.53–3.58 (1H, m), 3.58 (3H, s), 3.72 (1H, dd, J=25.88, 13.19 Hz), 3.86–3.93 (1H, m), 4.00–4.18 (2H, m), 5.50 (1H, dm, J=63.96 Hz), 5.51 (1h, brd. J=54.68 Hz), 7.68 (1H, d, 14.16 Hz), 8.19 (1H, d, J=3.91 Hz).

Elemental analysis data: as C$_{21}$H$_{22}$F$_3$N$_3$O$_4$ calcd.: C, 57.66; H, 5.07; N, 9.61 found: C, 57.52; H, 5.02; N, 9.48.

Example 19

10-[4-(R)-(1-Aminocyclopropyl)-3-(S)-fluoro-1-pyrrolidinyl]-9-fluoro-2,3-dihydro-3-(S)-methyl-7-oxo-7H-pyrido[1,2,3-de][1,4]benzoxazine-6-carboxylic acid hydrochloride 4-(R)-(1-tert-butoxycarbonylaminocyclopropyl)-3-(S)-fluoro-1-[1-(S)-phenylethyl]pyrrolidine (1.12 g, 3.21 mmol) was dissolved in ethanol (20 ml). After adding a 10% palladium-carbon catalyst (moisture content: 50.2%, 1.12 g), the mixture was stirred at 40° C. under a hydrogen atmosphere for 4 hours. After filtering off the catalyst through celite (washed with ethanol), the filtrate was concentrated under reduced pressure. The residue thus obtained was dissolved in dimethyl sulfoxide (10 ml), and 9.10-difluoro-2,3-dihydro-3-(S)-methyl-7-oxo-7H-pyrido[1,2,3-de][1,4]benzoxazine- 6-carboxylic acid-BF$_2$ chelate (705 mg, 2.14 mmol) and triethylamine (0.60 ml, 4.29 mmol) were added thereto. Then, the mixture was stirred at room temperature for 3 hours. After concentrating the liquid reaction mixture under reduced pressure, water was added to the residue. The yellow crystals thus precipitated were collected by filtration and washed with water. The thus obtained crystals were suspended in methanol (moisture content: 10%, 100 ml). After adding triethylamine (5 ml), the mixture was heated under reflux for 14 hours. After allowing it to cool, the liquid reaction mixture was concentrated under reduced pressure and the residue was dissolved in chloroform (200 ml) and washed with a 10% aqueous solution of citric acid (200 ml). The organic layer was dried over anhydrous sodium sulfate. After filtering, the filtrate was concentrated under reduced pressure. Under ice cooling, concentrated hydrochloric acid (10 ml) was dropped into the residue followed by stirring at room temperature for 10 minutes. After adding 1 N hydrochloric acid (30 ml), the liquid reaction mixture was washed with chloroform (50 ml×2) and its pH value was adjusted to 12.0 with an aqueous solution of sodium hydroxide. The pH value of this aqueous solution was adjusted to 7.4 with 1 N hydrochloric acid followed by extraction with chloroform (500 ml×3). The combined organic layer was dried over anhydrous sodium sulfate and filtered. The filtrate was concentrated under reduced pressure and 1 N hydrochloric acid (5.0 ml) was added dropwise into the residue under ice cooling. After stirring at the same temperature for 5 minutes, the liquid reaction mixture was concentrated under reduced pressure (azeotropic distillation with ethanol, three times). The residue was recrystallized from ethanol and dried under reduced pressure to obtain 685 mg (68.9%) of the title compound as a pale yellow powder.

$^1$H-NMR (400 MHz, 0.1 N-NaOD) δ: 0.59–0.68 (4H, m), 1.52 (3H, d, J=6.84 Hz), 2.39 (1H, dt, J=29.30, 7.81 Hz), 3.37 (1H, t, J=7.81 Hz), 3.74–3.90 (3H, m), 3.95 (1H, t, J=9.76 Hz), 4.36 (1H, d, J=10.26 Hz), 4.53 (1H, d, J=11.23 Hz), 4.62 (1H, q, J=6.84 Hz), 5.34 (1H, brd, J=54.02 Hz), 7.57 (1H, d, J=13.67 Hz), 8.35 (1H, s).

Elemental analysis data: as $C_{20}H_{21}F_2N_3O_4 \cdot HCl \cdot 1.25H_2O$ calcd.: C, 51.73; H, 5.32; N, 9.05 found: C, 51.97; H, 5.34; N, 9.10.

Example 20

5-Amino-7-[4-(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methyl-4-oxoquinoline-3-carboxylic acid hydrochloride 4-(R)-(1-tert-butoxycarbonylaminocyclopropyl)-3-(S)-fluoro-1-[1-(S)-phenylethyl]pyrrolidine (2.11 g, 6.06 mmol) was dissolved in ethanol (40 ml). After adding a 10% palladium-carbon catalyst (moisture content: 50.2%, 2.11 g), the mixture was stirred under a hydrogen atmosphere for 5 hours. After filtering off the catalyst through celite (washed with ethanol), the filtrate was concentrated under reduced pressure. The residue-thus obtained was dissolved in dimethyl sulfoxide (6 ml), and 5-amino-6,7-difluoro-1-[2-(S)-fluoro-1-(R)-cyclopropyl]-1,4-dihydro-8-methyl-4-oxoquinoline-3-carboxylic acid (1.26 g, 4.04 mmol) and triethylamine (14 ml) were added thereto. Then the mixture was stirred in a nitrogen atmosphere in an oil bath at 150° C. for 8 days. After allowing to cool, dimethyl sulfoxide was evaporated under reduced pressure and the residue was dissolved in chloroform (80 ml) and washed with a 10% aqueous solution of citric acid (80 ml). The organic layer was dried over anhydrous sodium sulfate. After filtering, the filtrate was concentrated under reduced pressure. Under ice cooling, concentrated hydrochloric acid (10 ml) was added dropwise into the residue followed by stirring at room temperature for 30 minutes. After adding 1 N hydrochloric acid (30 ml), the liquid reaction mixture was washed with chloroform (50 ml×2) and its pH value was adjusted to 12.0 with an aqueous solution of sodium hydroxide. The pH value of this aqueous solution was adjusted to 7.4 with 1 N hydrochloric acid followed by extraction with chloroform (500 ml×3). The combined organic layer was dried over anhydrous sodium sulfate and filtered. The filtrate was concentrated under reduced pressure and 1 N hydrochloric acid (5.0 ml) was added dropwise into the residue under ice cooling. After stirring at the same temperature for 5 minutes, the liquid reaction mixture was concentrated under reduced pressure (azeotropic distillation with ethanol, three times). The residue was recrystallized from ethanol and dried under reduced pressure to obtain 561 mg (28.8%) of the title compound as a pale yellow powder.

$^1$H-NMR (400 MHz, 0.1 N-NaOD) δ: 0.55–0.71 (4H, m), 1.10–1.21 (1H, m), 1.46–1.58 (1H, m), 2.30 (3H, s), 2.21–2.35 (1H, m), 3.32 (1H, t, J=8.79 Hz), 3.49 (1H, dd, J=25.88, 12.21 Hz), 3.85–3.97 (2H, m), 4.11 (1H, ddm, J=40.77, 12.45 Hz), 4.97 (1H, dm, J=70.31 Hz), 5.49 (1H, brd, J=55.18 Hz), 8.27 (1H, d, J=3.42 Hz).

Elemental analysis data: as $C_{21}H_{23}F_3N_4O_3 \cdot HCl \cdot 0.5H_2O$ calcd.: C, 52.34; H, 5.23; N, 11.63 found: C, 52.32; H, 5.36; N, 11.76.

Example 21

8-Amino-10-[4-(R)-(1-aminocyclopropyl)-3-(S)-fluoro-1-pyrrolidinyl]-9-fluoro-2,3-dihydro-3-(S)-methyl-7-oxo-7H-pyrido[1,2,3-de][1,4]benzoxazine-6-carboxylic acid 4-(R)-(1-tert-Butoxycarbonylaminocyclopropyl)-3-(S)-fluoro-1-[1-(S)-phenylethyl]pyrrolidine (900 mg, 2.58 mmol) was dissolved in ethanol (20 ml). After adding a 10% palladium-carbon catalyst (moisture content: 50.2%, 900 mg), the mixture was stirred under a hydrogen atmosphere for 4 hours. After filtering off the catalyst through celite (washed with ethanol), the filtrate was concentrated under reduced pressure. The residue thus obtained was dissolved in dimethyl sulfoxide (20 ml) and 8-amino-9,10-difluoro-2,3-dihydro-3-(S)-methyl-7-oxo-7H-pyrido[1,2,3-de][1,4]benzoxazine-6-carboxylic acid (593 mg, 2.00 mmol) and triethylamine (3 ml) were added thereto. Then the mixture was stirred in a nitrogen atmosphere in an oil bath at 100° C. for 25 hours. After allowing it to cool, dimethyl sulfoxide was evaporated under reduced pressure and the residue was dissolved in chloroform (100 ml.) and washed with a 10% aqueous solution of citric acid (80 ml). The organic layer was dried over anhydrous sodium sulfate. After filtering, the filtrate was concentrated under reduced pressure. Under ice cooling, concentrated hydrochloric acid (10 ml) was dropped into the residue followed by stirring at room temperature for 30 minutes. After adding 1 N hydrochloric acid (30 ml), the liquid reaction mixture was washed with chloroform (50 ml×4) and its pH value was adjusted to 12.0 with an aqueous solution of sodium hydroxide. The pH value of this aqueous solution was adjusted to 7.4 with 1 N hydrochloric acid followed by extraction with chloroform (500 ml×3). The combined organic layer was dried over anhydrous sodium sulfate and filtered. The filtrate was concentrated under reduced pressure and the residue was recrystallized from ethanol and dried under reduced pressure to obtain 640 mg (76.0%) of the title compound as a yellow powder.

$^1$H-NMR (400 MHz, 0.1 N-NaOD) δ: 0.53–0.68 (4H<m), 1.45 (3H, d, J=6.98 Hz), 2.18 (1H, dt, J=36.14, 7.81 Hz), 3.38 (1H, t, J=7.81 Hz), 3.66 (1H, dd, J=25.63, 12.94 Hz), 3.82 (1H, t, J=10.0 Hz), 3.99–4.12 (3H, m), 4.32 (1H, d, J=11.24 Hz), 4.44 (1H, d, J=6.98 Hz), 5.43 (1H, d, J=54.69 Hz), 8.13 (1H, s).

Elemental analysis data: as $C_{20}H_{22}F_2N_4O_4$ calcd.: C, 57.14; H, 5.27; N, 13.33 found: C, 56.86; H, 5.26; N, 13.39.

Referential Example 12-1

Ethyl 12-acetylcyclobutanecarboxylate

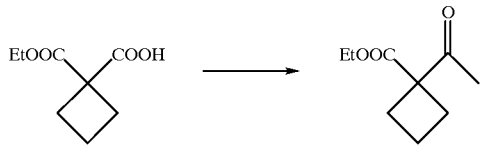

Ethyl hydrogen 1,1-cyclobutanecarboxylate (64.43 g, 374 mmol) was dissolved in methylene chloride (500 ml). Under ice cooling, oxalyl chloride (65.29 ml, 748 mmol) was added thereto followed by the addition of a catalytic amount of N,N-dimethylformamide. Then the resultant mixture was stirred at room temperature for 1.5 hours. After evaporating the solvent, the residue was twice subjected to azeotropic distillation together with toluene to provide an acid chloride.

On the other hand, copper (I) iodide (85.52 g, 449 mmol) was suspended in tetrahydrofuran (1 l) under a nitrogen gas stream. At −20° C., a 1.4 M solution (294 ml) of methyllithium in diethyl ether was added dropwise thereinto and the mixture was stirred at the same temperature for 1 hour. Subsequently, the above-mentioned acid chloride was dissolved in tetrahydrofuran (300 ml) and added dropwise thereinto at the same temperature followed by stirring for 1.5 hours. After completing the reaction, the reaction temperature was brought back to room temperature and a 10% aqueous solution of citric acid (500 ml) was added to the mixture. After evaporating tetrahydrofuran, ethyl acetate (1 l) was added to the residue. Then, insoluble matter was filtered off and the residue was washed successively with a 5% aqueous solution of sodium thiosulfate (300 ml) and a saturated aqueous solution of sodium chloride (300 ml) and dried over anhydrous sodium sulfate. After evaporating the solvent, the thus obtained residue was subjected to silica gel column chromatography (eluent:n-hexane:ethyl acetate= 4:1) to obtain 56.70 g (89%) of the title compound as an oily substance.

$^1$H-NMR (400 MHz, CDCl$_3$) δ: 1.27 (3H, t, J=7.33 Hz), 1.82–2.01 (2H, m), 2.12 (3H, s), 2.45–2.55 (4H, m), 4.20–4.24 (2H, m).

Referential Example 12-2

Ethyl 1-ethoxycarbonyl-β-hydroxy-β-methyl-cyclobutylpropanoate

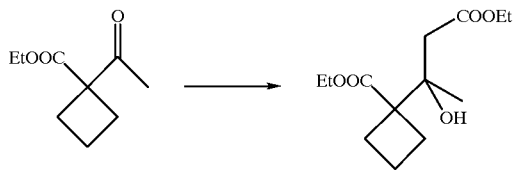

Ethyl 1-acetylcyclobutanecarboxylate (13.79 g, 81 mmol) was dissolved in tetrahydrofuran (50 ml) and zinc powder (10.59 g) and a catalytic amount of iodine were added thereto. While heating under reflux, a solution (100 ml) of ethyl bromoacetate (13.48 ml, 121 mmol) in tetrahydrofuran was added dropwise thereinto. Then, the liquid reaction mixture was heated under reflux for an additional 1 hour and allowed to cool. After adding 1 N hydrochloric acid (100 ml), the solvent was evaporated and ethyl acetate (500 ml) was added. The insoluble matter was filtered off, washed with a saturated aqueous solution of sodium chloride (300 ml) and dried over anhydrous sodium sulfate. After evaporating the solvent, the title compound was obtained in a quantitative amount as an oily substance.

$^1$H-NMR (400 MHz, CDCl$_3$) δ: 1.24–1.32 (9H, m), 1.73–1.87 (2H, m), 2,21–2.34 (2H, m), 2.41–2.57 (5H, m), 4.16–4.21 (4H, m).

Referential Example 12-3

(E)-Ethyl 3-(1-ethoxycarbonylcyclobutyl)-2-butenoate

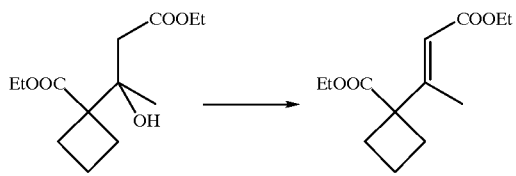

Ethyl 1-ethoxycarbonyl-β-hydroxy-β-methyl-cyclobutylpropanoate (22.27 g, 86 mmol) was dissolved in pyridine (42 ml) and thionyl chloride (8.18 ml, 112 mmol) was added dropwise thereinto at −10° C. After completing the reaction, the liquid reaction mixture was poured into ice water (250 ml) and extracted with ethyl acetate (100 ml×3). The combined organic layer was-washed with 1 N hydrochloric acid (100 ml) and a saturated aqueous solution of sodium chloride (100 ml) and dried over anhydrous sodium sulfate. After evaporating the solvent, the residue thus obtained was dissolved in methylene chloride (250 ml). Then 1,8-diazabicyclo [5,4,0]-7-undecene (12.89 ml) was added dropwise thereinto at 0° C. and the thus obtained mixture was stirred at room temperature for 18 hours. After completing the reaction, the solvent was evaporated. Ice water (100 ml) was added to the residue followed by extraction with ethyl acetate (200 ml×3). The combined organic layer was washed with 1 N hydrochloric acid (100 ml) and a saturated aqueous solution of sodium chloride (100 ml) and dried over anhydrous sodium sulfate. After evaporating the solvent, the residue was subjected to silica gel column chromatography (eluent:n-hexane:ethyl acetate= 4:1) to obtain 16.91 g (82%) of the title compound as an oily substance.

$^1$H-NMR (400 MHz, CDCl$_3$) δ: 1.24 (3H, t, J=6.83 Hz), 1.29 (3H, t, J=7.32 Hz), 1.74–1.80 (2H, m), 1.94–2.04 (1H, m), 2.07 (3H, d, J=1.47 Hz), 2.12–2.30 (2H, m), 2.12–2.30 (2H, m), 2.50–2.57 (2H, m), 4.13–4.20 (4H, m).

Referential Example 12-4

4-(1-Ethoxycarbonylcyclobutyl)-1-[1-(S)-phenylethyl]-3-pyrrolin-2-one

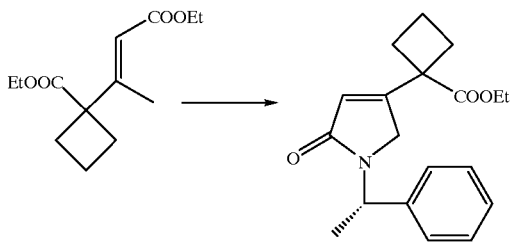

(E)-Ethyl 3-(1-ethoxycarbonylcyclobutyl)-2-butenoate (16.91 g, 70 mmol) was dissolved in chloroform (180 ml) and N-bromosucciniinide (12.53 g, 70 mmol) and a catalytic amount of azobisisobutyronitrile were added thereto. The thus obtained mixture was heated under reflux for 18 hours. After completing of the reaction, the solvent was evaporated and carbon tetrachloride (100 ml) was added to the residue. Then, insoluble matter was filtered off and the filtrate was concentrated. The residue was dissolved in ethanol (100 ml) and sodium hydrogencarbonate (11.82 g, 140 mmol) was added thereto. Next, (S)-phenylethylamine (9.87 ml, 77 mmol) was added dropwise thereinto at room temperature. After completing the addition, the resultant mixture was heated under reflux for 3 hours. After completing the reaction, the solvent was evaporated and methylene chloride (300 ml) was added to the residue. The insoluble matter was filtered off and the solvent was evaporated. The residue thus obtained was subjected to silica gel column chromatography (eluent:n-hexane:ethyl acetate=1:1) to obtain 19.57 g (43%) of the title compound as an oily substance.

$^1$H-NMR (400 MHz, CDCl$_3$) δ: 1.17 (3H, t, J=7.33 Hz), 1.74–1.80 (2H, m), 1.59 (3H, d,J=6.84 Hz), 1.84–2.01 (2H, m), 2.15–2.28 (2H, m), 2.60–2.69 (2H, m), 3.56 (2H, d, J=9.04 Hz), 3.88 (2H, d, J=9.04 Hz), 4.13 (2H, q, J=7.32 Hz), 5.50–5.59 (1H, m), 6.03 (2H, s), 7.26–7.35 (5H, m).

Referential Example 12-5

4-(1-Ethoxycarbonylcyclobutyl)-1-[(S)-phenylethyl]-2-pyrrolidone

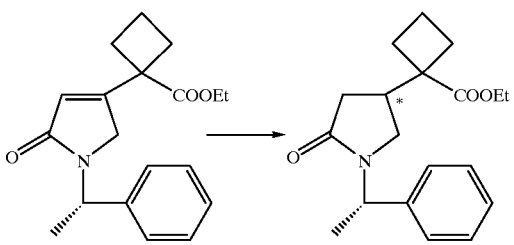

4-(1-Ethoxycarbonylcyclobutyl)-1-[(S)-phenylethyl]-3-pyrrolin-2-one (9.57 g, 31 mmol) was dissolved in ethanol (150 ml) and platinum oxide (230 mg) was added thereto. The thus obtained mixture was stirred in a hydrogen atmosphere for 18 hours. After completing the reaction, the liquid reaction mixture was filtered and concentrated. The residue thus obtained was thrice subjected to silica gel column chromatography (eluent:n-hexane:ethyl acetate=1:1) to obtain 2.3 g (24%) of an optical isomer A of the title compound and 7.1 g (74%) of another optical isomer B thereof each as an oily substance.

Optical isomer A $^1$H-NMR (400 MHz, CDCl$_3$) δ: 1.26 (3H, t, J=6.83 Hz), 1.49 (2H, d, J=7.32 Hz), 1.83–1.95 (4H, m), 2.38–2.54 (4H, m), 2.66–2.74 (1H, m), 3.01 (1H, t, 8.30 Hz), 3.14 (1H, d, J=5.86, 9.77 Hz), 4.09–4.18 (2H, m), 5.48 (1H, dd, J=7.32, 14.16 Hz), 7.27–7.35 (5H, m).

Optical isomer B $^1$H-NMR (400 MHz, CDCl$_3$) δ: 1.17 (3H, t, J=7.32 Hz), 1.52 (2H, d, J=7.33 Hz), 1.68–1.92 (4H, m), 2.23–2.43 (3H, m), 2.50–2.57 (1H, m), 2.73–2.86 (2H, m), 3.37 (1H, t, J=8.30 Hz), 4.05 (2H, q, J=7.32 Hz), 5.50 (1H, dd, J=7.32, 14.16 Hz), 7.24–7.35 (5H, m).

Referential Example 12-6 trans 4-(1-Ethoxycarbonylcyclobutyl)-3-fluoro-1-[1-(S)-phenylethyl]-2-pyrrolidone (optical isomer B)

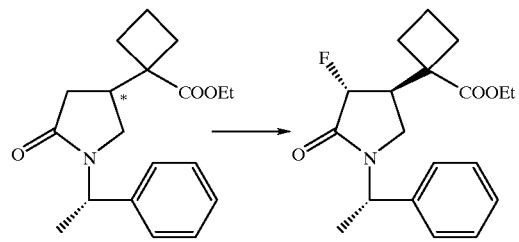

Under a nitrogen atmosphere, diisopropylamine (2.55 ml, 18.2 mmol) was dissolved in dry tetrahydrofuran (120 ml). After cooling the solution to −78° C., a 1.63 M solution of n-butyllithium in n-hexane (11.2 ml, 18.2 mmol) was added dropwise thereinto over a period of 10 minutes. Then, the liquid reaction mixture was stirred at 0° C. for 15 minutes and cooled to −78° C. Next, a solution (30 ml) of 4-(1-ethoxycarbonylcyclopropyl)-1-[1-(S)-phenylethyl]-2-pyrrolidone (optical isomer B; 4.42 g, 14.01 mmol) in dry tetrahydrofuran was added dropwise thereinto over a period of 15 minutes. The liquid reaction mixture was stirred at −78° C. for 1 hour. Then, a solution (25 ml) of N-fluorobenzenedisulfonimide (7.07 g, 22,42 mmol) in dry tetrahydrofuran was added dropwise thereinto over a period of 5 minutes. The liquid reaction mixture was stirred at −78° C. for 30 minutes and then heated to room temperature followed by stirring for an additional 20 minutes. Under ice cooling, a saturated aqueous solution of ammonium chloride (200 ml) was added to the liquid reaction mixture. After evaporating tetrahydrofuran, the aqueous layer was extracted with ethyl acetate (200 ml×2). The combined organic layer was washed with water (200 ml×3), dried over anhydrous sodium sulfate and filtered. The filtrate was concentrated under reduced pressure and the residue was subjected to silica gel column chromatography (eluent:n-hexane:ethyl acetate=1:1) to obtain 3.88 g (83%) of the title compound as an oily substance.

$^1$H-NMR (400 MHz, CDCl$_3$) δ: 1.14 (3H, t, J=6.83 Hz), 1.57 (2H, d, J=6.83 Hz), 1.88–2.08 (4H, m), 2.33–2.58 (3H, m), 2.81–2.92 (1H, m), 3.42 (1H, t, J=9.77 Hz), 3.93–4.07 (2H, m), 5.18 (1H, dd, J=6.83, 53.22 Hz), 5.51 (1H, dd, J=7.32, 14.16 Hz), 7.25–7.34 (5H, m).

Referential Example 12-7 cis 4-(1-Ethoxycarbonylcyclobutyl)-3-fluoro-1-[1-(S)-phenylethyl]-2-pyrrolidone (optical isomer B)

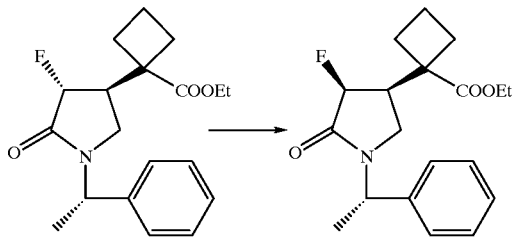

Under a nitrogen atmosphere, diisopropylamine (2.97 ml, 21.19 mmol) was dissolved in dry tetrahydrofuran (30 ml). After cooling the solution to −78° C., a 1.63 M solution of n-butyllithium in n-hexane (10.8 ml, 17.60 mmol) was added dropwise thereinto over a period of 5 minutes. Then, the liquid reaction mixture was stirred at 0° C. for 15 minutes and cooled to −78° C. Next, a solution (30 ml) of trans 4-(1-ethoxycarbonyl-cyclopropyl)-3-fluoro-1-[1-(S)-phenylethyl]-2-pyrrolidone (optical isomer B; 4.71 g, 14.13 mmol) in dry tetrahydrofuran was added dropwise thereinto over a period of 5 minutes. The liquid reaction mixture was stirred at −78° C. for 3 minutes. Then, it was added dropwise into a solution (40 ml) of 2,6-di-tert-butylphenol (4.37 g, 21.18 mmol) in dry tetrahydrofuran over a period of 5 minutes. The liquid reaction mixture was stirred at −78° C. for 10 minutes and a saturated aqueous solution of ammonium chloride (200 ml) was added thereto. Next, the liquid reaction mixture was brought back to room temperature and the organic layer was taken up. The aqueous layer was extracted with chloroform (100 ml×2). The combined organic layer was washed with water (100 ml×2), dried over anhydrous sodium sulfate and filtered. The filtrate was concentrated under reduced pressure and the residue was subjected to silica gel column chromatography to obtain 1.96 g (42%) of the starting compound (eluent:n-hexane:ethyl acetate=2:1) and 1.79 g (38%) of the title compound (eluent:n-hexane:ethyl acetate=3:2) each as an oily substance.

$^1$H-NMR (400 MHz, CDCl$_3$) δ: 1.22 (3H, t, J=6.83 Hz), 1.56–1.58 (3H, d, J=6.83 Hz), 1.84–2.42 (6H, m), 2.83–2.97 (1H, m), 3.15–3.24 (1H, m), 3.36–3.43 (1H, m) 4.11–4.17 (2H, m), 5.07 (1H, dd, J=6.83, 52.24 Hz), 5.56 (1H, q, J=7.33 Hz), 7.26–7.36 (5H, m).

Referential Example 12-8 cis 4-(1-Carboxycyclobutyl)-3-fluoro-1-[1-(S)-phenylethyl]-2-pyrrolidone (optical isomer B)

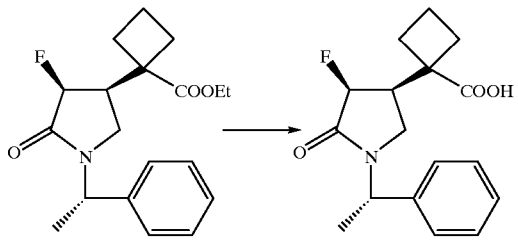

cis 4-(1-Ethoxycarbonylcyclobutyl)-3-fluoro-1-[1-(S)-phenylethyl]-2-pyrrolidone (optical isomer B; 1.79 g, 5.37 mmol) was dissolved in methanol (10 ml) and a 1 N aqueous solution of sodium hydroxide was added dropwise thereinto. The liquid reaction mixture was stirred at 40° C. for 18 hours and then methanol was evaporated under reduced pressure. Water (50 ml) was added to the residue followed by washing with chloroform (100 ml). The aqueous layer thus separated was acidified by dropping 1 N hydrochloric acid thereinto and then extracted with chloroform (100 ml×2). The combined organic layer was dried over anhydrous sodium sulfate and filtered. The filtrate was concentrated under reduced pressure to obtain the title compound in a quantitative amount as a crude product.

Referential Example 12-9 cis 4-(1-tert-Butoxycarbonylaminocyclobutyl)-3-fluoro-1-[1-(S)-phenylethyl]-2-pyrrolidone (optical isomer B)

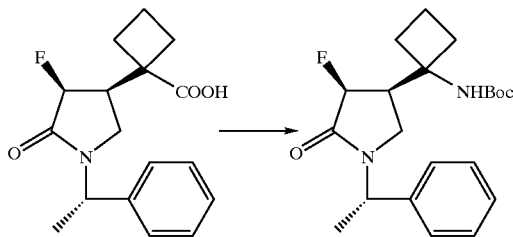

cis 4-(1-Carboxycyclobutyl)-3-fluoro-1-[1-(S)-phenylethyl]-2-pyrrolidone (optical isomer B; 1.92 g, 6.29 mmol) was dissolved in dry acetonitrile (30 ml) and N,N'-carbonyldiimidazole (1.33 g, 8.20 mmol) was added thereto. The liquid reaction mixture was stirred at 60° C. for 1 hour. Then ammonia was bubbled thereinto at room temperature for 10 minutes. After concentrating the liquid reaction mixture under reduced pressure, water (100 ml) was added to the residue followed by washing with chloroform (100 ml×2). The combined organic layer was dried over anhydrous sodium sulfate and filtered. The filtrate was concentrated under reduced pressure and the residue thus obtained was dissolved in tert-butyl alcohol (50 ml). After adding lead tetraacetate (6.32 g, 14.25 mmol), the mixture was heated under reflux for 1 hour. The liquid reaction mixture was then allowed to cool followed by the addition of diethyl ether (50 ml) and sodium hydrogencarbonate (6 g). Next, it was stirred at room temperature for 10 minutes and filtered. The filtrate was concentrated under reduced pressure and ethyl acetate (100 ml) was added to the residue. The thus obtained mixture was washed with a saturated aqueous solution of sodium bicarbonate, dried over anhydrous sodium sulfate and filtered. The filtrate was concentrated under reduced pressure to obtain 1.74 g (65%) of the title compound as an oily substance.

$^1$H-NMR (400 MHz, CDCl$_3$) δ: 1.40 (9H, s), 1.92–2.21 (6H, m), 3.04–3.12 (1H, m), 3.31–3.38 (1H, m), 4.87 (1H, brs), 5.01 (1H, dd, J=5.86, 52.73 Hz), 5.52 (1H, dd, J=7.32, 14.16 Hz), 7.30–7.38 (5H, m).

Referential Example 12-10 cis 1-[1-(S)-phenylethyl]-4-(1-tert-butoxycarbonylaminocyclobutyl)-3-fluoropyrrolidone (optical isomer B)

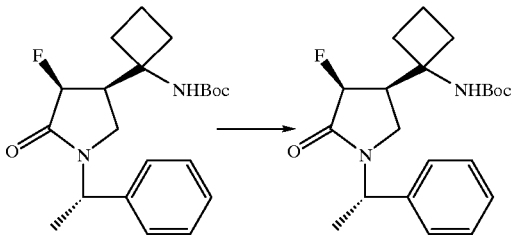

cis 4-(1-tert-Butoxycarbonylaminocyclobutyl)-3-fluoro-1-[1-(S)-phenylethyl]-2-pyrrolidone (optical isomer B; 1.74 g, 4.62)mol) was dissolved in tetrahydrofuran (30 ml). At 0° C., a borane-tetrahydrofuran complex salt (13.86 ml) was added thereto and the resultant mixture was stirred at room temperature for 2 days. After completing the reaction, the solvent was evaporated and water (50 ml) was added to the residue followed by extraction with chloroform (100 ml×2). The combined organic layer was dried over anhydrous sodium sulfate and filtered. The filtrate was concentrated under reduced pressure and the residue thus obtained was dissolved in 80% moisture-containing methanol (40 ml). After adding triethylamine (10 ml), the mixture was heated under reflux for 2 hours. After removing the solvent by evaporation, the thus obtained residue was subjected to silica gel column chromatography (eluent:n-hexane:ethyl acetate=2:1) to obtain 1.13 g (67%) of the title compound as an oily substance.

$^1$H-NMR (400 MHz, CDCl$_3$) δ: 1.37 (3H, d, J=6.35 Hz), 1.44 (9H, s), 1.65–2.58 (7 H, m), 2.70–2.92 (4H, m), 3.27–3.32 (1H, m), 5.14 (1H, brd), 5.53 (1H, brs), 7.22–7.33 (5H, m).

Example 22

5-Amino-7-[cis 4-(1-aminocyclobutyl)-3-fluoro-1-pyrrolidinyl]-6-fluoro-1-[2-(S)-fluoro-1-(R)-cyclopropyl]-1,4-dihydro-8-methyl-4-oxoquinoline-3-carboxylic acid (optical isomer B)

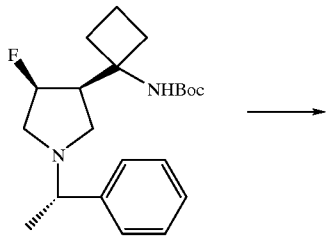

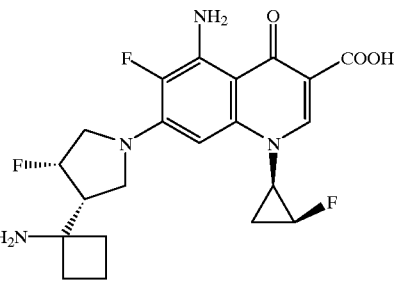

cis 1-[1-(S)-phenylethyl]-4-(1-tert-butoxycarbonylaminocyclobutyl)-3-fluoropyrrolidine (optical isomer B; 1.13 g, 3.12 mmol) was dissolved in ethanol (20 ml). After adding a 10% palladium-carbon catalyst (moisture content: 55.6%, 1.0 g), the mixture was stirred under a hydrogen atmosphere at 50° C. for 18 hours. After filtering off the catalyst through celite (washed with methanol), the filtrate was concentrated under reduced pressure. The residue thus obtained was dissolved in dimethyl sulfoxide (10 ml), and 5-amino-6,7-difluoro-1-[2-(S)-fluoro-1-(R)-cyclopropyl]-1,4-dihydro-8-methyl-4-oxoquinoline-3-carboxylic acid (1.18 g, 3.78 mmol) and triethylamine (5 ml) were added thereto. Then, the mixture was stirred in a nitrogen atmosphere at 140° C. for 4 days. After allowing it to cool, dimethyl sulfoxide was evaporated under reduced pressure and the residue was dissolved in chloroform (50 ml) and washed successively with a 10% aqueous solution of citric acid (50 ml) and a saturated aqueous solution of sodium chloride (100 ml). The organic layer was dried over anhydrous sodium sulfate. After filtering, the-filtrate was concentrated under reduced pressure. The residue was then subjected to flash silica gel column chromatography (eluent:chloroform methanol=9:1) and the eluate was concentrated under reduced pressure. Under ice cooling, concentrated hydrochloric acid (5 ml) was dropped into the residue followed by stirring at room temperature for 30 minutes. After adding 1 N hydrochloric acid (30 ml), the liquid reaction mixture was washed with chloroform (50 ml×2) and its pH value was adjusted to 12.0 with an aqueous solution of sodium hydroxide. The liquid reaction mixture was washed with chloroform (100 ml) and then its pH value was adjusted to 7.4 with 1 N hydrochloric acid followed by extraction with chloroform (150 ml×3). The combined organic layer was dried over anhydrous sodium sulfate and filtered. The filtrate was concentrated under reduced pressure and the residue was purified by preparative TLC (developed at the bottom layer of chloroform:methanol:water=7:3:1) to obtain the title compound as a crude product. After recrystallizing from ethanol/ether, 157 mg (17%) of the title compound was obtained.

M.p.: 177–184° C.

$^1$H-NMR (400 MHz, CDCl$_3$) δ: 1.16–2.34 (13H, m), 2.47–2.60 (1H, m), 3.35 (1H, t, J=8.79 Hz), 3.53 (1H, q, J=12.21 Hz), 3.78–3.83 (1H, m), 4.09–4.21 (2H, m), 4.76–4.95 (1H, m), 5.42 (1H, dt, J=3.41, 55.18 Hz), 6.53 (2H, brs), 8.60 (1H, d, J=3.41 Hz).

Elemental analysis data: as C$_{22}$H$_{25}$F$_3$N$_4$O$_3$.0.5H$_2$O calcd.: C, 57.51; H, 5.70; N, 12.19 found: C, 57.59; H, 5.52; N, 11.89.

Acute Toxicity

A solution of 5-amino-7-[4-(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methyl-4-oxoquinoline-3- carboxylic acid (abbreviated as cis) hydrochloride of Example 15 or 5-amino-7-[4-(R)-(1-aminocyclopropyl)-3-(R)-fluoro-1-pyrrolidinyl]-6-fluoro-1-[2-(S)-fluoro-1-(R)-cyclopropyl]-1,4-dihydro-8-methyl-4-oxoquinoline-3-carboxylic acid (abbreviated as trans) hydrochloride in distilled water for injection was administered intravenously to Slc:ddy five week male mice (five mice per group) and the symptoms are observed. The results are as follows.

Results

| Compound | Dose | Number of death |
|---|---|---|
| cis | 150 mg/kg | 0/5 |
| trans | 150 mg/kg | 2/2* |
| trans | 100 mg/kg | 2/2* |
| trans | 50 mg/kg | 0/5 |

"*": The mouse died immediately after the administration is finished. The test was stopped at the second mouse died.

The same result was obtained for the compounds of Inventive Examples 14, 16, 17, 18, 21 and 22 at a dose of 150 mg/kg in the test illustrated above.

The antimicrobial activity expressed as a minimum inhibitory concentration (MIC, μg/ml) of the compounds of Example Nos. 15, 16, 18, 19 and 21 with respect to various microbial strains is set forth in Tables 4 and 5 below.

TABLE 4

| | Example No. | | |
|---|---|---|---|
| Strain/Compound | 15 | 16 | 18 |
| E. coli, NIHJ | ≦0.003 | 0.006 | ≦0.003 |
| S. flexneli, 2A 5503 | ≦0.003 | 0.006 | 0.006 |
| Pr. vulgaris, 08601 | 0.013 | 0.05 | 0.006 |
| Pr. mirabilis, IFO-3849 | 0.025 | 0.10 | 0.05 |
| Ser. marcescens, 10100 | 0.05 | 0.20 | 0.10 |
| Ps. aeruginosa, 32104 | 0.10 | 0.39 | 0.20 |
| Ps. aeruginosa, 32121 | 0.05 | 0.20 | 0.10 |
| X. maltophilia, 11D-1275 | 0.05 | 0.20 | 0.20 |
| S. aureus, 209P | ≦0.003 | ≦0.003 | ≦0.003 |
| S. epidermidis, 56500 | ≦0.003 | 0.006 | 0.013 |
| Str. pyogenes, G-36 | ≦0.003 | 0.013 | 0.006 |
| Str. faecalis, ATCC-19433 | 0.025 | 0.05 | 0.025 |
| S. aureus, 870307 | 0.025 | 0.025 | 0.025 |

TABLE 5

| | Example No. | |
|---|---|---|
| Strain/Compound | 19 | 21 |
| E. coli, NIHJ | 0.010 | 0.006 |
| S. flexneli, 2A 5503 | 0.010 | 0.013 |
| Pr. vulgaris, 08601 | 0.025 | 0.10 |
| Pr. mirabilis, IFO-3849 | 0.10 | 0.10 |
| Ser. marcescens, 10100 | 0.10 | 0.20 |
| Ps. aeruginosa, 32104 | 0.39 | 0.39 |
| Ps. aeruginosa, 32121 | 0.10 | 0.20 |
| X. maltophilia, 11D-1275 | 0.39 | 0.39 |
| S. aureus, 209P | 0.006 | 0.006 |
| S. epidermidis, 56500 | 0.025 | 0.013 |
| Str. pyogenes, G-36 | 0.010 | 0.025 |
| Str. faecalis, ATCC-19433 | 0.05 | 0.05 |
| S. aureus, 870307 | 0.20 | 0.20 |

While the invention has been described in detail and with reference to specific embodiments thereof, it will be apparent to one skilled in the art that various changes and modifications can be made therein without departing from the spirit and scope thereof.

What is claimed is:

1. A compound represented by formula (I), a free acid thereof, a salt of the free acid, a hydrate of the free acid, or a hydrate of a salt of the free acid:

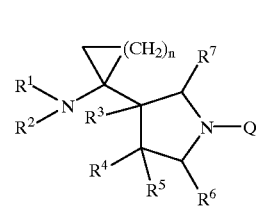

(I)

wherein $R^1$ represents a hydrogen atom or an alkyl group having 1 to 6 carbon atoms;

$R^2$ represents a hydrogen atom or an alkyl group having 1 to 6 carbon atoms, wherein the alkyl group represented by $R^2$ may have at least one substituent selected from the group consisting of a hydroxyl group, a halogen atom, an alkylthio group having 1 to 6 carbon atoms and an alkoxyl group having 1 to 6 carbon atoms;

$R^3$ represents a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, wherein the alkyl group represented by $R^3$ may have at least one substituent selected from the group consisting of a hydroxyl group, a halogen atom and an alkoxyl group having 1 to 6 carbon atoms;

one of $R^4$ and $R^5$ represents a hydrogen atom, and the other represents a hydroxymethyl group, a methyl group, a methoxyl group or a fluorine atom, or $R^4$ and $R^5$ may be combined to form a hydroxyimino group, a poly-methylene chain having 3 to 6 carbon atoms so as to form a spiro cyclic structure together with the pyrrolidine ring or an alkyloxyimino group having 1 to 6 carbon atoms;

$R^6$ and $R^7$ each independently represents a hydrogen atom or an alkyl group having 1 to 6 carbon atoms;

n is an integer of 1 to 3; and

Q is a partial structure represented by the following formula (II):

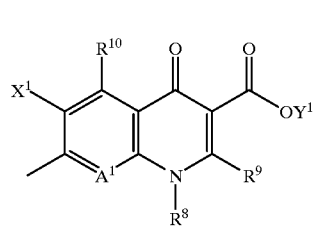

(II)

wherein $R^8$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have one or more substituents, an aryl group which may have one or more substituents, a heteroaryl group which may have one or more substituents, an alkoxyl group having 1 to 6 carbon atoms or an alkylamino group having 1 to 6 carbon atoms;

$R^9$ represents a hydrogen atom or an alkylthio group having 1 to 6 carbon atoms, wherein $R^8$ and $R^9$ may be combined to form a cyclic structure including a part of the mother nucleus, and the ring may contain a sulfur atom as a ring constituting atom and may further have an alkyl group having 1 to 6 carbon atoms as a substituent;

$X^1$ represents a halogen atom or a hydrogen atom;

$R^{10}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, wherein the amino group represented by $R^{10}$ may have at least one substituent selected from the group consisting of a formyl group, an alkyl group having 1 to 6 carbon atoms and an acyl group having 2 to 5 carbon atoms;

$A^1$ represents a nitrogen atom, or a partial structure represented by the following formula (III):

(III)

wherein $X^2$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, wherein the amino group represented by $R^2$ may have at least one substituent selected from the group consisting of a formyl group, an alkyl group having 1 to 6 carbon atoms and an acyl group having 2 to 5 carbon atoms, and $X^2$ and $R^8$ may be combined to form a cyclic structure including a part of the mother nucleus, and the ring may contain an oxygen atom, a nitrogen atom or a sulfur atom as a ring constituting atom and may further have an alkyl group having 1 to 6 carbon atoms as a substituent; and $Y^1$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group, or Q is a partial structure represented by the following formula (IV):

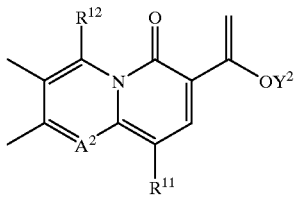

(IV)

wherein $R^{11}$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have one or more substituents, an aryl group which may have one or more substituents, a heteroaryl group which may have one or more substituents, an alkoxyl group having 1 to 6 carbon atoms or an alkylamino group having 1 to 6 carbon atoms;

$R^{12}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, wherein the amino group represented by $R^{12}$ may have at least one substituent selected from the group consisting of a formyl group, an alkyl group having 1 to 6 carbon atoms and an acyl group having 2 to 5 carbon atoms;

$X^3$ represents a halogen atom or a hydrogen atom;

$A^2$ represents a nitrogen atom or a partial structure represented by the following formula

(V)

wherein $X^4$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, wherein the amino group represented $X^4$ may have at least one substituent selected from the group consisting of a formyl group, an alkyl group having 1 to 6 carbon atoms and an acyl group having 2 to 5 carbon atoms, and $X^4$ and $R^{11}$ may be combined to form a cyclic structure including a part of the mother nucleus, and the ring may contain an oxygen atom, a nitrogen atom or a sulfur atom as a ring constituting atom and may further have an alkyl group having 1 to 6 carbon atoms as a substituent); and $Y^2$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1, 3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group.

2. The compound represented by formula (I), a free acid thereof, a salt of the free acid, a hydrate of the free acid, or a hydrate of a salt of the free acid according to claim 1, wherein Q in formula (I) is represented by formula (II).

3. The compound represented by formula (I), a free acid thereof, a salt of the free acid, a hydrate of the free acid, or a hydrate of a salt of the free acid according to claim 2, wherein $R^8$ is a halogenocyclopropyl group.

4. The compound represented by formula (I), a free acid thereof, a salt of the free acid, a hydrate of the free acid, or a hydrate of a salt of the free acid according to claim 3, wherein the halogenocyclopropyl group represented by $R^8$ is a 1,2-cis-2-halogenocyclopropyl group.

5. The compound represented by formula (I), a free acid thereof, a salt of the free acid, a hydrate of the free acid, or a hydrate of a salt of the free acid according to claim 3 or 4, wherein the halogenocyclopropyl group represented by $R^8$ is a stereochemically pure substituent.

6. The compound represented by formula (I), a free acid thereof, a salt of the free acid, a hydrate of the free acid, or a hydrate of a salt of the free acid according to claim 5, wherein the halogenocyclopropyl group represented by $R^8$ is a (1R,2S)-2-halogenocyclopropyl group.

7. The compound represented by formula (I), a free acid thereof, a salt of the free acid, a hydrate of the free acid, or a hydrate of a salt of the free acid according to claim 6, wherein the halogen atom of the halogenocyclopropyl group represented by $R^8$ is a fluorine atom.

8. The compound represented by formula (I), a free acid thereof, a salt of the free acid, a hydrate of the free acid, or a hydrate of a salt of the free acid according to claim 7, wherein the compound of formula (I) is a stereochemically pure compound.

9. A pharmaceutical preparation which comprises the compound of formula (I), its salt or a hydrate thereof according to claim 1 as an active ingredient.

10. An antibacterial drug which comprises the compound of formula (I), its salt or a hydrate thereof according to claim 1 as an active ingredient.

11. A compound represented by formula (XI), a free acid thereof, a salt of the free acid, a hydrate of the free acid, or a hydrate of a salt of the free acid:

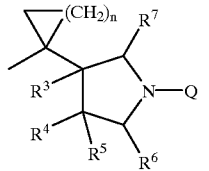

(XI)

wherein $R^1$ represents a hydrogen atom or an alkyl group having 1 to 6 carbon atoms;

$R^2$ represents a hydrogen atom or an alkyl group having 1 to 6 carbon atoms, provided that the alkyl group represented by $R^2$ may have one or more substituents selected from the group consisting of a hydroxyl group, a halogen atom and an alkoxyl group having 1 to 6 carbon atoms;

$R^3$ and $R^5$ each represents a hydrogen atom;

$R^4$ represents a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, provided that the alkyl group represented by $R^4$ may have one or more substituents selected from the group consisting of a hydroxyl group, a halogen atom and an alkoxyl group having 1 to 6 carbon atoms, and $R^4$ and the substituent on the pyrrolidine ring of the following formula:

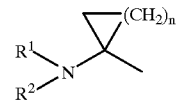

are located in the cis-configuration;

$R^6$ and $R^7$ each independently represents a hydrogen atom or an alkyl group having 1 to 6 carbon atoms;

n is an integer of from 1 to 3; and

Q represents a partial structure represented by the following formula:

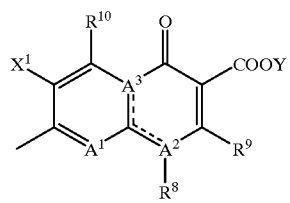

wherein $R^8$ represents an alkyl group having 1 to 6 carbon atoms, an alkenyl group having 2 to 6 carbon atoms, a halogenoalkyl group having 1 to 6 carbon atoms, a substituted or unsubstituted cyclic alkyl group having 3 to 6 carbon atoms, a substituted or unsubstituted aryl group, a substituted or unsubstituted heteroaryl group, an alkoxyl group having 1 to 6 carbon atoms or an alkylamino group having 1 to 6 carbon atoms;

$R^9$ represents a hydrogen atom or an alkylthio group having 1 to 6 carbon atoms;

$R^9$ and $R^8$ may form together with a part of the mother nucleus a cyclic structure optionally containing a sulfur atom as a constituent atom thereof and optionally having an alkyl group having 1 to 6 carbon atoms as a substituent;

$R^{10}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, provided that said amino group may have one or more substituents selected from the group consisting of a formyl group, an alkyl group having 1 to 6 carbon atoms and an acyl group having 2 to 5 carbon atoms;

$X^1$ represents a halogen atom or a hydrogen atom;

$A^1$ represents a nitrogen atom or a partial structure represented by the following formula (XII):

(XII)

wherein $X^2$ represents a hydrogen atom, an amino group, a halogen atom, a cyano group, a halogenomethyl group, a halogenomethoxy group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, provided that the amino group represented by $X^2$ may have one or more substituents selected from the group consisting of a formyl group, an alkyl group having 1 to 6 carbon atoms and an acyl group having 2 to 5 carbon atoms, and $X^2$ and $R^8$ may form together with a part of the mother nucleus a cyclic structure optionally containing an oxygen atom, a nitrogen atom or a sulfur atom as a constituent atom thereof and optionally having an alkyl group having 1 to 6 carbon atoms as a substituent;

$R^2$ and $A^3$ each represents a nitrogen atom or a carbon atom, provided that $A^2$ and $A^3$ may form together with the carbon atom to which they are bonded a partial structure represented by the following formula:

>C=C(A¹=)—N(R⁸)— or a partial structure represented by the following formula:

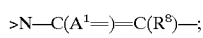

>N—C(A¹=)=C(R⁸)—;

and

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkyl group having 1 to 6 carbon atoms and a phenyl group.

12. The compound represented by formula (XI), a free acid thereof, a salt of the free acid, a hydrate of the free acid, or a hydrate of a salt of the free acid according to claim 1, wherein Q is represented by the following formula:

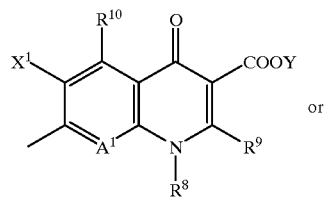

or

-continued

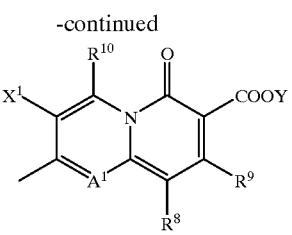

wherein $R^8$ represents an alkyl group having 1 to 6 carbon atoms, an alkenyl group having 2 to 6 carbon atoms, a halogenoalkyl group having 1 to 6 carbon atoms, a substituted or unsubstituted cyclic alkyl group having 3 to 6 carbon atoms, a substituted or unsubstituted aryl group, a substituted or unsubstituted heteroaryl group, an alkoxyl group having 1 to 6 carbon atoms or an alkylamino group having 1 to 6 carbon atoms;

$R^9$ represents a hydrogen atom or an alkylthio group having 1 to 6 carbon atoms, $R^9$ and $R^8$ may form together with a part of the mother nucleus a cyclic structure optionally containing a sulfur atom as a constituent atom thereof and optionally having an alkyl group having 1 to 6 carbon atoms as a substituent;

$R^{10}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, provided that said amino group may have one or more substituents selected from the group consisting of a formyl group, an alkyl group having 1 to 6 carbon atoms and an acyl group having 2 to 5 carbon atoms, $X^1$ represents a halogen atom or a hydrogen atom;

$A^1$ represents a nitrogen atom or a partial structure represented by the following formula (XII):

(XII)

wherein $X^2$ represents a hydrogen atom, an amino group, a halogen atom, a cyano group, a halogenomethyl group, a halogenomethoxy group, an alkyl group having 1 to 6 carbon atoms, an alkenyl group having 2 to 6 carbon atoms, an alkenyl group having 2 to 6 carbon atoms or an alkoxyl group having 1 to 6 carbon atoms, provided that the amino group represented by $X^2$ may have one or more substituents selected from the group consisting of a formyl group, an alkyl group having 1 to 6 carbon atoms and an acyl group having 2 to 5 carbon atoms, and $X^2$ and $R^8$ may form together with a part of the mother nucleus a cyclic structure optionally containing an oxygen atom, a nitrogen atom or a sulfur atom as a constituent atom thereof and optionally having an alkyl group having 1 to 6 carbon atoms as a substituent;

$R^2$ and $A^3$ each represents a nitrogen atom or a carbon atom, provided that $A^2$ and $A^3$ may form together with the carbon atom to which they are bonded a partial structure represented by the following formula:

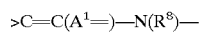

>C=C(A¹=)—N(R⁸)— or a partial structure represented by the following formula:

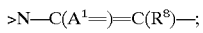

and

Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkyl group having 1 to 6 carbon atoms and a phenyl group.

13. A compound represented by formula (XI), a free acid thereof, a salt of the free acid, a hydrate of the free acid, or a hydrate of a salt of the free acid:

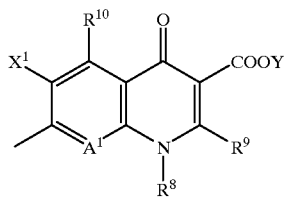

(XI)

wherein $R^1$ represents a hydrogen atom or an alkyl group having 1 to 6 carbon atoms;

$R^2$ represents a hydrogen atom or an alkyl group having 1 to 6 carbon atoms, provided that the alkyl group represented by $R^2$ may have one or more substituents selected from the group consisting of a hydroxyl group, a halogen atom and an alkoxyl group having 1 to 6 carbon atoms;

$R^3$ and $R^5$ each represents a hydrogen atom;

$R^4$ represents a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, provided that the alkyl group represented by $R^4$ may have one or more substituents selected from the group consisting of a hydroxyl group, a halogen atom and an alkoxyl group having 1 to 6 carbon atoms, and $R^4$ and the substituent on the pyrrolidine ring of the following formula:

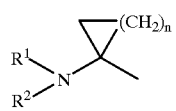

are located in the cis-configuration;

$R^6$ and $R^7$ each independently represents a hydrogen atom or an alkyl group having 1 to 6 carbon atoms;

n is an integer of from 1 to 3; and

Q represents a partial structure represented by the following formula:

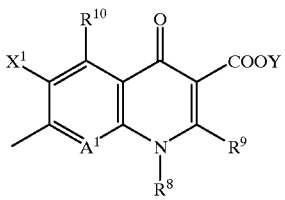

wherein $R^8$, $R^9$, $R^{10}$, $X^1$ and Y are each as defined in claim 12.

14. The compound represented by formula (XI), a free acid thereof, a salt of the free acid, a hydrate of the free acid, or a hydrate of a salt of the free acid according to claim 11, 12 or 13, wherein $R^4$ is a halogen atom.

15. The compound represented by formula (XI), a free acid thereof, a salt of the free acid, a hydrate of the free acid, or a hydrate of a salt of the free acid according to claim 11, 12 or 13, wherein $R^4$ is a fluorine atom.

16. The compound represented by formula (XI), a free acid thereof, a salt of the free acid, a hydrate of the free acid, or a hydrate of a salt of the free acid according to claim 11, 12 or 13, wherein n is 1 or 2.

17. The compound represented by formula (XI), a free acid thereof, a salt of the free acid, a hydrate of the free acid, or a hydrate of a salt of the free acid according to claim 11, 12, or 13 wherein n is 1.

18. The compound represented by formula (XI), a free acid thereof, a salt of the free acid, a hydrate of the free acid, or a hydrate of a salt of the free acid according to claim 11, 12 or 13, wherein $R^4$ is a fluorine atom and n is 1 or 2.

19. The compound represented by formula (XI), a free acid thereof, a salt of the free acid, a hydrate of the free acid, or a hydrate of a salt of the free acid according to claim 11, 12 or 13, wherein $R^4$ is a fluorine atom and n is 1.

20. The compound represented by formula (XI), a free acid thereof, a salt of the free acid, a hydrate of the free acid, or a hydrate of a salt of the free acid according to claim 11, 12 or 13, wherein $R^8$ is a halogenocyclopropyl group.

21. The compound represented by formula (XI), a free acid thereof, a salt of the free acid, a hydrate of the free acid, or a hydrate of a salt of the free acid according to claim 11, 12 or 13, wherein $R^8$ is a 1,2-cis-2-halogenocyclopropyl group.

22. The compound represented by formula (XI), a free acid thereof, a salt of the free acid, a hydrate of the free acid, or a hydrate of a salt of the free acid according to claim 11, 12 or 13, wherein $R^8$ is a stereochemically pure substituent.

23. The compound represented by formula (XI), a free acid thereof, a salt of the free acid, a hydrate of the free acid, or a hydrate of a salt of the free acid according to claim 11, 12 or 13, wherein $R^8$ is a (1R,2S)-2-halogenocyclopropyl group.

24. The compound represented by formula (XI), a free acid thereof, a salt of the free acid, a hydrate of the free acid, or a hydrate of a salt of the free acid according to claim 11, 12 or 13, wherein $R^3$ is a (1R,2S)-2-fluorocyclopropyl group.

25. The compound represented by formula (XI), a free acid thereof, a salt of the free acid, a hydrate of the free acid, or a hydrate of a salt of the free acid according to claim 11, 12 or 13, wherein $X^1$ is a halogen atom.

26. The compound represented by formula (XI), a free acid thereof, a salt of the free acid, a hydrate of the free acid or a hydrate of a salt of the free acid according to claim 25, wherein said halogen atom represented by $X^1$ is a fluorine atom.

27. The compound represented by formula (XI), a free acid thereof, a salt of the free acid, a hydrate of the free acid, or a hydrate of a salt of the free acid according to claim 11, 12 or 13, which is stereochemically pure compound.

28. A drug containing as an active ingredient the compound represented by formula (XI) according to claim 11, 12 or 13, a free acid thereof, a salt of the free acid, a hydrate of the free acid, or a hydrate of a salt of the free acid.

29. The drug of claim 28, wherein the drug is an antimicrobial agent containing as an active ingredient, an antimicrobial effective amount of the compound represented by formula (XI) according to claim 28, a free acid thereof, a salt of the free acid, a hydrate of the free acid, or a hydrate of a salt of the free acid.

30. A compound represented by the following formula (XVI), a free acid thereof, a salt of the free acid, a hydrate of the free acid, or a hydrate of a salt of the free acid:

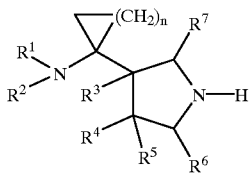

(XVI)

wherein $R^1$ represents a hydrogen atom or an alkyl group having 1 to 6 carbon atoms;

$R^2$ represents a hydrogen atom or an alkyl group having 1 to 6 carbon atoms, provided that the alkyl group represented by $R^2$ may have one or more substituents selected from the group consisting of a hydroxyl group, a halogen atom and an alkoxyl group having 1 to 6 carbon atoms;

$R^3$ and $R^5$ each represents a hydrogen atom;

$R^4$ represents a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, provided that said alkyl group may have one or more substituents selected from the group consisting of a hydroxyl group, a halogen atom and an alkoxyl group having 1 to 6 carbon atoms, and $R^4$ and the substituent on the pyrrolidine ring of the following formula:

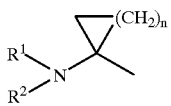

are located in the cis-configuration;

$R^6$ and $R^7$ each independently represents a hydrogen atom or an alkyl group having 1 to 6 carbon atoms; and n is an integer of from 1 to 3.

31. The compound represented by formula (XI), a free acid thereof, a salt of the free acid, a hydrate of the free acid, or a hydrate of a salt of the free acid according to claim 30, wherein $R^4$ is a halogen atom.

32. The compound represented by formula (XVI), a free acid thereof, a salt of the free acid, a hydrate of the free acid, or a hydrate of a salt of the free acid according to claim 30, wherein $R^4$ is a fluorine atom.

33. The compound represented by formula (XVI), a free acid thereof, a salt of the free acid, a hydrate of the free acid, or a hydrate of a salt of the free acid according to claim 30, 31, 32, wherein n is 1 or 2.

34. The compound represented by formula (XVI), a free acid thereof, a salt of the free acid, a hydrate of the free acid, or a hydrate of a salt of the free acid according to claim 30, 31, 32, wherein n is 1.

35. The compound represented by formula (XVI), a free acid thereof, a salt of the free acid, a hydrate of the free acid, or a hydrate of a salt of the free acid according to claim 30, wherein $R^4$ is a fluorine atom and n is 1 or 2.

36. The compound represented by formula (XVI), a free acid thereof, a salt of the free acid, a hydrate of the free acid, or a hydrate of a salt of the free acid according to claim 30, wherein $R^4$ is a fluorine atom and n is 1.

37. 4-(R)-(1-Aminocyclopropyl)-3-(S)-fluoro-1-pyrrolidine, a free acid thereof, a salt of the free acid, a hydrate of the free acid, or a hydrate of a salt of the free acid.

38. The compound represented by formula (XI), a free acid thereof, a salt of the free acid, a hydrate of the free acid, or a hydrate of a salt of the free acid according to claim 11, 12 or 13, wherein Q is a 6-carboxy-9-fluoro-2, 3-dihydro-3-(S)-methyl-7-oxo-7H-pyrido(1,2,3-de) b 1,4]-benzoxazin-10-yl group.

39. The compound represented by formula (XI), a free acid thereof a salt of the free acid, a hydrate of the free acid, or a hydrate of a salt of the free acid according to claim 11, 12 or 13, wherein Q is an 8-amino-6-carboxy-9-fluoro-2,3-dihydro-3-(S)-methyl-7-oxo-7H-pyrido[1,2,3-de][1,4]benzoxazin-10-yl group.

40. The compound represented by formula (XI), a free acid thereof, a salt of the free acid, a hydrate of the free acid, or a hydrate of a salt of the free acid according to claim 11, 12 or 13 wherein Q is a 5-amino-3-carboxy-6-fluoro-1-[2-(S)-fluoro-1-(R)-cyclopropyl]-1, 4-dihydro-8-methoxy-4-oxoquinolin-7-yl group.

41. The compound represented by formula (XI), a free acid thereof, a salt of the free acid, a hydrate of the free acid, or a hydrate of a salt of the free acid according to claim 11, 12 or 13, wherein Q is a 5-amino-3-carboxy-6-fluoro-1-[2-(S)-fluoro-1-(R)-cyclopropyl]-1,4-dihydro-8-methyl-4-oxoquinolin-7-yl group.

42. The compound represented by formula (XI), a free acid thereof, a salt of the free acid, a hydrate of the free acid, or a hydrate of a salt of the free acid according to claim 11, 12 or 13, wherein Q is a 3-carboxy-6-fluoro-1-[2-(S)-fluoro-1-(R)-cyclopropyl]-1, 4-dihydro-8-methoxy-4-oxoquinolin-7-yl group.

43. 10-[4-(R)-(1-Aninocyclopropyl)-3-(S)-fluoro-1-pyrrolidinyl]-9-fluoro-2, 3-dihydro-3-(S)-methyl-7-oxo-7H-pyrido [1,2,3-de][1,4]benzoxazine-6-carboxylic acid, a free acid thereof, a salt of the free acid, a hydrate of the free acid, or a hydrate of a salt of the free acid.

44. 8-Amino-10-[4-(R)-(1-aminocyclopropyl)-3-(S)-fluoro-1-pyrrolidinyl]-9-fluoro-2, 3-dihydro-3-(S)-methyl-7-oxo-7H-pyrido[1,2,3-de][1,4]benzoxazine-6-carboxylic acid, a free acid thereof, a salt of the free acid, a hydrate of the free acid, or a hydrate of a salt of the free acid.

45. 5-Amino-7-[4(R)-(1-aminocyclopropyl)-3-(S)-fluoro-1-pyrrolidinyl]-6-fluoro-1-[2-(S)-fluoro-1-(R)-cyclopropyl]-1,4-dihydro-8-methyl-4-oxoquinoline-3-carboxylic acid, a free acid thereof, a salt of the free acid, a hydrate of the free acid, or a hydrate of a salt of the free acid.

46. 5-Amino-7-[4-(R)-(1-aminocyclopropyl-3-(S)-fluoro-1-pyrrolidinyl]-6-fluoro-1-[2-(S)-fluoro-1-(R)-cyclopropyl]-1,4-dihydro-8-methoxy-4-oxoquinoline-3-carboxylic acid, a free acid thereof, a salt of the free acid, a hydrate of the free acid, or a hydrate of a salt of the free acid.

47. 7-[4-(R)-(1-Aminocyclopropyl)-3-(S)-fluoro-1-pyrrolidinyl]-6-fluoro-1-[2-(S)-fluoro-1-(R)-cyclopropyl]-1, 4-dihydro-8-methoxy-4-oxoquinoline-3-carboxylic acid, a free acid thereof, a salt of the free acid, a hydrate of the free acid, or a hydrate of a salt of the free acid.

* * * * *

UNITED STATES PATENT AND TRADEMARK OFFICE
CERTIFICATE OF CORRECTION

PATENT NO. : 6,121,285  
DATED : September 19, 2000  
INVENTOR(S) : Makoto Takemura, Youichi Kimura, Hisashi Takahashi, Kenichi Kimura, Satoru Miyauchi, Hitoshi Ohki It is certified that error appears in the above-identified patent and that said Letters Patent is hereby corrected as shown below:

Column 123:
Lines 46-55 Delete the following chemical structure:

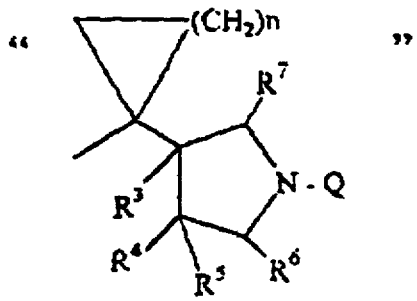

And insert the correct formula XI as follows:

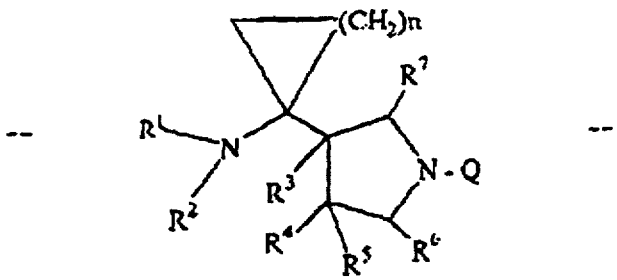

UNITED STATES PATENT AND TRADEMARK OFFICE
CERTIFICATE OF CORRECTION

PATENT NO.   : 6,121,285
DATED         : September 19, 2000
INVENTOR(S)  : Makoto Takemura, Youichi Kimura, Hisashi Takahashi, Kenichi Kimura, Satoru Miyauchi, Hitoshi Ohki It is certified that error appears in the above-identified patent and that said Letters Patent is hereby corrected as shown below:

Column 125:
Line 26, delete "$R^2$" and insert --$A^2$--;
Line 56, delete "1" and insert --11--;

Column 126:
Lines 62 through Column 127, line 5, delete in its entirety;

Column 127:
Line 18, delete "A compound" and insert --The compound--.
Lines 24-32 delete the following chemical structure:

"  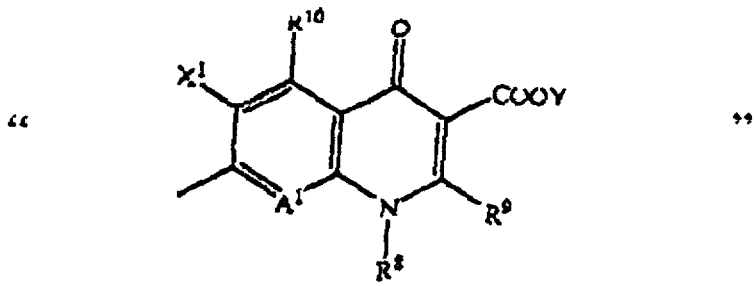  "

UNITED STATES PATENT AND TRADEMARK OFFICE
CERTIFICATE OF CORRECTION

PATENT NO. : 6,121,285
DATED : September 19, 2000
INVENTOR(S) : Makoto Takemura, Youichi Kimura, Hisashi Takahashi, Kenichi Kimura, Satoru Miyauchi, Hitoshi Ohki It is certified that error appears in the above-identified patent and that said Letters Patent is hereby corrected as shown below:

(127 continued)
And insert the correct formula XI as follows:

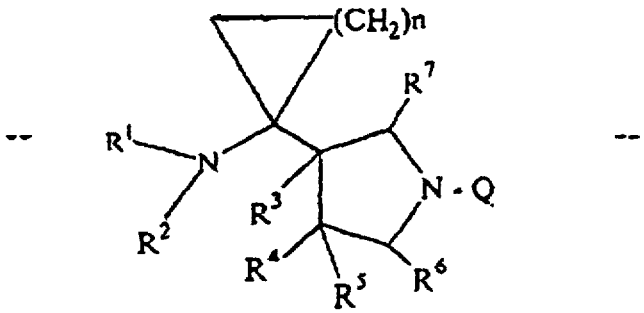

Column 130:
Line 42 delete "(1-aninocyclopropyl)"
and insert --(1-aminocyclopropyl)--

Signed and Sealed this

Seventh Day of August, 2001

*Attest:*

NICHOLAS P. GODICI
*Attesting Officer*   *Acting Director of the United States Patent and Trademark Office*